United States Patent
Noda et al.

(10) Patent No.: US 7,344,246 B2
(45) Date of Patent: Mar. 18, 2008

(54) OBSERVATION APPARATUS

(75) Inventors: Toru Noda, Kanagawa (JP); Kazuhiko Onuma, Chiba (JP); Yasufumi Fukuma, Tokyo (JP); Koji Nishio, Tokyo (JP); Hidetaka Aeba, Tokyo (JP); Yoshio Okazaki, Tokyo (JP); Masaru Sato, Tokyo (JP); Yasuo Kato, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 620 days.

(21) Appl. No.: 10/862,462

(22) Filed: Jun. 8, 2004

(65) Prior Publication Data

US 2005/0018134 A1    Jan. 27, 2005

(30) Foreign Application Priority Data

Jun. 9, 2003    (JP) .............................. 2003-163466

(51) Int. Cl.
   A61B 3/10   (2006.01)
   A61B 3/00   (2006.01)
(52) U.S. Cl. ..................... 351/205; 351/216; 351/219
(58) Field of Classification Search ........ 351/205–206, 351/216, 217, 219
   See application file for complete search history.

(56) References Cited

U.S. PATENT DOCUMENTS

| 4,518,231 | A | 5/1985 | Muchel et al. | 350/516 |
|---|---|---|---|---|
| 4,927,250 | A | 5/1990 | Suda | 350/500 |
| 5,615,278 | A | 3/1997 | Matsumoto | 382/128 |
| 5,625,499 | A | 4/1997 | Chen | 359/831 |
| 5,684,595 | A | 11/1997 | Kato et al. | 356/401 |
| 5,713,047 | A | 1/1998 | Kohayakawa | 396/18 |
| 5,865,829 | A | 2/1999 | Kitajima | 606/3 |
| 6,283,596 | B1 | 9/2001 | Yoshimura et al. | 351/214 |
| 6,304,723 | B1 | 10/2001 | Kohayakawa | 396/18 |
| 6,726,326 | B2 * | 4/2004 | Fukuma et al. | 351/216 |
| 2001/0028441 | A1 | 10/2001 | Okamoto et al. | 351/214 |
| 2002/0051639 | A1 | 5/2002 | Enomoto | 396/311 |

(Continued)

FOREIGN PATENT DOCUMENTS

DE        35 46 915 C2    8/1999

(Continued)

OTHER PUBLICATIONS

European Search Report dated Jan. 24, 2005, 3 pages.

*Primary Examiner*—Alicia M Harrington
(74) *Attorney, Agent, or Firm*—Edwards Angell Palmer & Dodge LLP

(57) ABSTRACT

An observation apparatus is provided. An apex angle of a contact prism is inputted by operating an apex angle setting knob of a control panel. A fining angle of the contact prism is inputted by operating a fitting angle setting knob. A control unit determines the amount of correction for astigmatism of a left observation optical system and the amount of correction for astigmatism of a right observation optical system based on a recognized observation magnification and the inputted apex angle. An axial angle for the astigmatism of the left observation optical system and an axial angle for the astigmatism of the right observation optical system are determined based on the inputted fitting angle. Variable cross cylinder lens rotating drive units are controlled to rotate cylinder lenses of each of the right and left observation optical systems, thereby obtaining the determined axial angle and the determined amount of correction.

20 Claims, 39 Drawing Sheets

U.S. PATENT DOCUMENTS

2002/0191280 A1  12/2002  Horiguchi et al. .......... 359/383
2002/0196472 A1  12/2002  Enomoto .................. 358/3.26

FOREIGN PATENT DOCUMENTS

| | | |
|---|---|---|
| EP | 1 321 095 A2 | 6/2003 |
| JP | 05-023304 | 2/1993 |
| JP | 05-023304 A | 2/1993 |
| JP | 2001-037726 | 2/2001 |
| JP | 2003-062003 | 3/2003 |
| WO | WO 01/60241 A1 | 8/2001 |

* cited by examiner

OBSERVATION APPARATUS

BACKGROUND OF THE INVENTION

1. Field of the Invention

The present invention relates to an improvement of an observation apparatus such as an operation microscope apparatus or a slit lamp microscope apparatus, and more particularly to an observation apparatus capable of removing astigmatism and chromatic aberration which occur when a state of an eye is observed.

2. Description of the Related Art

Up to now, there has been widely known an observation apparatus such as an operation microscope apparatus used for observing an eye which undergoes an operation (hereinafter referred to as "an eye to be operated") (see JP 2003-062003A, specification paragraphs [0029] to [0032], FIGS. 4, 5, and 9) or a slit lamp microscope apparatus used for observing the anterior ocular segment and fundus portion of an eye to be examined (see JP 2001-037726 A, specification paragraphs [0017] to [0020], FIG. 1).

Hereinafter, such an observation apparatus, in particular, an operation microscope apparatus will be described. An operation microscope apparatus having an external structure as shown in FIG. 1 has been known as an example. The operation microscope apparatus shown in FIG. 1 includes a support post 1 for supporting the apparatus onto a floor surface, a support arm 2 for supporting an operation microscope main body, and bracket 3 for operation microscope main body attachment, which is bonded to a tip portion of the support arm 2.

The support arm 2 is composed of an L-shaped arm 4 and a pivot arm 5. The L-shaped arm 4 is bonded to an upper end of the support post 1 to be pivotable in the lateral direction. The pivot arm 5 is urged upward by elastic action of a spring stored in the arm.

An arm 6 supported to be pivotable in the lateral direction is provided to a tip portion of the pivot arm 5 to face downward. The bracket 3 is bonded to a lower end portion of the arm 6. An operation microscope 10 composing a main body of the operation microscope apparatus is attached to the bracket 3.

The operation microscope 10 is mainly composed of a lens barrel 11 that stores various optical systems. The lens barrel 11 is provided with an eyepiece lens barrel 11' for observation of the eye to be operated as an observation object by an operator.

For example, an illumination optical system 12 and an observation optical system 13 as shown in FIG. 2 are placed in the lens barrel 11 of the operation microscope 10. The illumination optical system 12 used for illuminating an eye to be operated E includes an illumination light source 14, a condensing lens 15, an illumination field stop 16, a collimator lens 17, a prism 18, and an objective lens 19, which are disposed in this order. Note that reference numeral 18b denotes a reflective surface of the prism 18. Illumination light emitted from the illumination light source 14 is reflected on the reflective surface 18b of the prism 18 through the condensing lens 15, the illumination field stop 16, and the collimator lens 17. The reflected illumination light is guided to the eye to be operated E by the objective lens 19 to illuminate a pupil Ea, an iris Eb, and a cornea Ec.

The observation optical system 13 is an optical system for receiving observation light for observing the eye to be operated E, which is illuminated by the illumination optical system 12. As shown in FIG. 3, the observation optical system 13 is composed of a left observation optical system 13a and a right observation optical system 13b.

The left observation optical system 13a includes the objective lens 19, a variable lens system (zoom lens system) 20 composed of lenses 20a, 20b, and 20c, a beam splitter 21, an imaging lens 22, an image erecting prism 23, an interpupillary adjustment prism 24, a field stop 25, and an eyepiece 26, which are disposed in this order. Note that reference numeral 2a1 denotes an entrance pupil and 26a denotes an eye point.

Similarly, the right observation optical system 13b includes the objective lens 19, a variable lens system (zoom lens system) 30 composed of lenses 30a, 30b, and 30c, a beam splitter 31, an imaging lens 32, an image erecting prism 33, an interpupillary adjustment prism 34, a field stop 35, and an eyepiece 36, which are disposed in this order. Note that reference numeral 2b1 denotes an entrance pupil and 36a denotes an eye point.

Reflection light (observation light) on the eye to be operated E, which is illuminated by the illumination optical system 12, passes through the objective lens 19. Then, the observation light is guided to the right and left eyes of the operator through respective optical elements of the left and right observation optical systems 13a and 13b. A part of the observation light is reflected by the beam splitters 21 and 31 to be guided to an auxiliary observation optical system 40 and a TV image pickup system 50.

The auxiliary observation optical system 40 is an optical system used for observation of the eye to be operated E by an operator's assistant and includes an imaging lens 41, a reflecting mirror 42, and an eyepiece 43. The TV image pickup system 50 is an optical system for taking an image of the eye to be operated E and includes an imaging lens 51, a reflecting mirror 52, and a TV camera 53. The TV camera 53 is provided with a CCD image pickup element 53a serving as an image receiving unit.

FIG. 4 is a schematic view in the case where the observation optical system 13 shown in FIG. 3 is viewed from the above. In FIG. 4, an optical axis of the objective lens 19 is indicated as "O" and optical axes (observation optical axes) of the left and right observation optical systems 13a and 13b are indicated as O1 and O2. A surface 18a of the prism 18 becomes an exit pupil of the illumination optical system 12 and is disposed near observation optical paths 2a2 and 2b2 of the left and right observation optical systems 13a and 13b.

According to such an operation microscope apparatus, it is possible to observe the anterior ocular segment of the eye to be operated E. However, it is impossible to observe the surroundings of a fundus Er (fundus surroundings) of the eye to be operated E without changing the structure of the apparatus. In order to facilitate the observation of the fundus surroundings, utilized in many situations is a method of illuminating fundus surroundings Er' with a state in which an optical member 60 such as a prism having a predetermined apex angle (for example, 45 degrees) as shown in FIG. 5 is put to the cornea Ec of the eye to be operated E so as to reduce refracting power of the cornea Ec and to refract illumination light. An intraocular observation contact lens as disclosed in JP 05-023304 A (specification paragraphs [0016] to [0027], FIG. 1) is also used.

When the optical member 60 is put to the cornea Ec, light beams parallel to the optical axis "O" of the objective lens 19 and an illumination optical axis O' of the illumination optical system 12 (see FIGS. 2 and 4) are refracted and, in addition, light beams parallel to the observation optical axes O1 and O2 of the left and right observation optical systems 13a and 13b are refracted. Therefore, it is possible to observe the fundus surroundings Er'. When, for example, a prism having one of various apex angles θ is used as the optical member 60 as appropriate, an observation region of the fundus surroundings Er' can be changed as appropriate.

The number of types of the recent operation microscope apparatus as described in JP 2003-062003 A has been increasing, each of which includes an optical member (which is called a front lens) provided so as to be insertable between the eye to be operated and the objective lens, thereby allowing an operator to perform an operation with both hands.

When the optical member 60 having deflective action such as the prism or the contact lens is put to the eye to be operated E to observe the fundus surroundings Er', astigmatism and chromatic aberration are caused by optical refractive and dispersive action. That is, with respect to a point image on the fundus surroundings Er', when the optical member 60 is put to the eye to be operated E, the astigmatism occurs in which the point image to be observed is changed from a state of a longitudinal ellipse to a state of a transverse ellipse through a state of a minimum circle with changing a focusing state of the point image from the front side of a focusing position to the rear side thereof, thereby distorting an observation image. Therefore, the sharpness of the observation image deteriorates.

Even with respect to the chromatic aberration, when the optical member 60 is put to the eye to be operated E, the chromatic aberration occurs even at the focusing position in a direction of the apex angle of the optical member 60. When chromatic aberration is occurring, even if the astigmatism is removed, the chromatic aberration remains, so that the observation image appears to separate for each color. Therefore, the sharpness of the observation image deteriorates.

When the apex angle θ of the optical member 60 reduces or when a refraction index of a material composing the optical member 60 increases, the astigmatism and the chromatic aberration become more significant. Therefore, when the fundus surroundings further apart from the fundus Er are observed, the sharpness of the observation image further deteriorates.

The astigmatism and the chromatic aberration occur even in an eyeball optical system of the eye to be operated E. In particular, when an eye to be operated into which an intraocular lens (IOL) used for the treatment of cataract and the like is inserted is observed, the influences of the astigmatism and the chromatic aberration become larger.

The amount of astigmatism and the amount of chromatic aberration which are caused by the optical member 60 and the eyeball optical system of the eye to be operated increase substantially proportional to an exit angle of an observation light flux passing through the optical member 60.

When an operation is performed using the operation microscope apparatus, the operator usually observes the eye to be operated E over the head of a patient (located on a low side in FIG. 4). When the fundus surroundings Er' located in the longitudinal direction viewed from the operator (height direction of the patient) are observed with respect to the fundus Er of the eye to be operated E, exit angles of right and left observation light fluxes passing through the optical member 60 (angles formed between the normal to an oblique surface of the optical member 60 and each of the observation optical axes O1 and O2) are equal to each other. However, when the fundus surroundings Er' located in the lateral direction viewed from the operator are observed, the exit angles of the right and left observation light fluxes are greatly different from each other.

For example, as shown in FIG. 5, assume that the apex angle of the optical member (prism) 60 is given by θ and a convergent angle of the operation microscope (angle formed between the left and right observation optical axes O1 and O2) is given by β. When the fundus surrounding Er' located on the left side viewed from the operator is observed, an exit angle $α_L$ of light parallel to the observation optical axis O1 of the left observation optical system 13a becomes (90°−θ+β/2) and an exit angle $α_R$ of light parallel to the observation optical axis O2 of the right observation optical system 13b becomes (90°−θ−β/2). Therefore, in such a case, the influences of astigmatism and chromatic aberration on an image of the fundus surrounding Er' observed by the left eye of the operator are larger than those on an image of the fundus surrounding Er' observed by the right eye of the operator. Similarly, when the fundus surrounding Er' located on the right side viewed from the operator is observed, the influences of astigmatism and chromatic aberration on an image of the fundus surrounding Er' observed by the right eye of the operator are larger than those on an image of the fundus surrounding Er' observed by the left eye of the operator.

As described above, when the aberration amounts of the images observed by the right and left eyes are different from each other, it is hard for the operator to normally stereoscopically view the image of the fundus surrounding Er'.

The above-mentioned problem related to the astigmatism affects the case where coagulation treatment is performed on the fundus surroundings using laser light with the optical member such as the prism having the deflective action put to the cornea. Even when the above-mentioned front lens is put between the eye to be operated and the objective lens, the problems related to the astigmatism and the chromatic aberration occur.

SUMMARY OF THE INVENTION

The present invention has been made in view of the above circumstances. An object of the present invention is to provide an observation apparatus capable of suitably removing astigmatism that occurs when a state of an eye including a fundus and a vitreous body is observed.

Another object of the present invention is to provide an observation apparatus capable of suitably removing chromatic aberration that occurs when the state of the eye is observed.

In order to achieve the above-mentioned object, according to a first aspect of the present invention, there is provided an observation apparatus, including: a variable lens system for changing an observation magnification for observing an eye to be observed, which is an observation object; and an imaging lens for imaging a light flux passing through the variable lens system, the variable lens system and the imaging lens being disposed on each of right and left observation optical paths between an objective lens opposed to the eye to be observed and eyepieces for right and left eyes, an observation optical path, which is for relaying a reflection light flux on the eye to be observed as a parallel light flux to the variable lens system, being formed between the objective lens and the variable lens system in each of the right and left observation optical paths, an observation optical path, which is for relaying the reflection light flux obtained through the variable lens system as a parallel light flux to the imaging lens, being formed between the variable lens system and the imaging lens in each of the right and left observation optical paths, the apparatus being characterized in that an astigmatism canceling optical element for canceling power of astigmatism that occurs when a predetermined optical member is placed between the eye to be observed and the objective lens, which is right and left independently operable, is provided on each of the right and left observation optical paths.

Also, in order to achieve the above-mentioned object, according to a second aspect of the present invention, there is provided an observation apparatus according to the first aspect, being characterized in that the astigmatism canceling optical element is a variable cross cylinder lens composed of a pair of concave cylinder lens and a convex cylinder lens, which are provided to relatively rotatable about an observation optical axis of the observation optical path.

Also, in order to achieve the above-mentioned object, according to a third aspect of the present invention, there is provided an observation apparatus according to the second aspect, being characterized in that the variable cross cylinder lens includes: aberration direction setting means for setting a direction of the power of the astigmatism; and correction amount setting means for setting an amount of correction with respective right and left variable cross cylinder lens for canceling the power of the astigmatism.

Also, in order to achieve the above-mentioned object, according to a fourth aspect of the present invention, there is provided an observation apparatus according to the second aspect, being characterized in that the predetermined optical member placed between the eye to be observed and the objective lens is a prism fit in contact with a cornea of the eye to be observed, and that the observation apparatus further includes: apex angle input means for inputting an apex angle of the prism; fitting angle input means for inputting a fitting angle of the prism to the cornea; drive means for independently rotating respectively the right and left variable cross cylinder lenses; and control means for independently controlling rotation of the right and left variable cross cylinder lenses by the drive means based on the apex angle inputted by the apex angle input means and the fitting angle inputted by the fitting angle input means.

Also, in order to achieve the above-mentioned object, according to a fifth aspect of the present invention, there is provided an observation apparatus according to the fourth aspect, being characterized in that the control means independently controls rotation of the right and left variable cross cylinder lenses respectively by the drive means based on the observation magnification changed by the variable lens system.

Also, in order to achieve the above-mentioned object, according to a sixth aspect of the present invention, there is provided an observation apparatus according to the fourth or fifth aspect further including: image receiving means for receiving observation images of the eye to be observed from the reflection light fluxes on the eye to be observed, which are guided through the right and left observation optical paths; and first correction amount computing means for computing an amount of correction for canceling the power of the astigmatism by performing predetermined analyzing processing on the observation images received by the image receiving means, the apparatus being characterized in that the control means independently controls rotation of the right and left variable cross cylinder lenses respectively by the drive means based on the amount of correction computed by the first correction amount computing means.

Also, in order to achieve the above-mentioned object, according to a seventh aspect of the present invention, there is provided an observation apparatus according to the fourth or fifth aspect further including: a projection optical system for projecting a pattern image to the eye to be observed; image receiving means for receiving reflection images of the pattern image projected to the eye to be observed by the projection optical system, which are guided through the right and left observation optical paths; and second correction amount computing means for computing an amount of correction for canceling the power of the astigmatism by performing predetermined analyzing processing on the reflection images of the pattern image which are received by the image receiving means, the apparatus being characterized in that the control means independently controls rotation of the right and left variable cross cylinder lenses respectively by the drive means based on the amount of correction computed by the second correction amount computing means.

Also, in order to achieve the above-mentioned object, according to an eighth aspect of the present invention, there is provided an observation apparatus according to any one of the first to fifth aspects further including: image receiving means for receiving an observation image of the eye to be observed from the reflection light flux on the eye to be observed, which is guided through one of the right and left observation optical paths; and third correction amount computing means for computing an amount of correction for canceling the power of the astigmatism that occurs in the one of the right and left observation optical paths by performing predetermined analyzing processing on the observation image received by the image receiving means and then computing an amount of correction for canceling the power of the astigmatism that occurs in the other of the right and left observation optical paths based on the computed correction amount, the apparatus being characterized in that the astigmatism canceling optical elements are independently right and left respectively operated based on the amount of correction for the astigmatism in each of the right and left observation optical paths, which is computed by the third correction amount computing means.

Also, in order to achieve the above-mentioned object, according to a ninth aspect of the present invention, there is provided an observation apparatus according to the fourth or fifth aspect further including: memory means for storing an amount of correction for canceling the power of the astigmatism, corresponding to the apex angle of the prism and the fitting angle of the prism; image receiving means for receiving an observation image of the eye to be observed from the reflection light flux on the eye to be observed, which is guided through one of the right and left observation optical paths; and third correction amount computing means for computing an amount of correction for canceling the power of the astigmatism that occurs in the one of the right and left observation optical paths by performing predetermined analyzing processing on the observation image received by the image receiving means and then computing an amount of correction for canceling the power of the astigmatism that occurs in the other of the right and left observation optical paths based on the computed correction amount and the amount of correction for canceling the power of the astigmatism, corresponding to the apex angle and the fitting angle, which is stored in the memory means, the apparatus being characterized in that the control means independently controls rotation of the right and left variable cross cylinder lenses respectively by the drive means based on the amount of correction for the astigmatism in each of the right and left observation optical paths, which is computed by the third correction amount computing means.

Also, in order to achieve the above-mentioned object, according to a tenth aspect of the present invention, there is provided an observation apparatus according to the fourth or fifth aspect further including: memory means for storing an amount of correction for canceling power of an astigmatism caused by a prism having a predetermined apex angle in association with an observation magnification changed by the variable lens system; and correction amount calculating means for calculating an amount of correction for a prism having an apex angle different from the predetermined apex angle at an observation magnification different from a specific observation magnification based on the amount of correction which is stored in the memory means in association with the observation magnification and the amount of correction for the prism having the apex angle different from the predetermined apex angle at the specific observation magnification, which is obtained in advance, the apparatus being characterized in that the control means independently controls rotation of the right and left variable cross cylinder lenses respectively by the drive means based on the amount of correction for the astigmatism in each of the right and left observation optical paths, which is calculated by the correction amount calculating means.

Also, in order to achieve the above-mentioned object, according to an eleventh aspect of the present invention, there is provided an observation apparatus according to any one of the second to tenth aspects, further including a correction lens for changing a direction of positive or negative power produced by the variable cross cylinder lens to a direction of positive or negative power of the astigmatism.

Also, in order to achieve the above-mentioned object, according to a twelfth aspect of the present invention, there is provided an observation apparatus according to any one of the second to tenth aspects further including focusing position correction means for correcting displacement of a focusing position which occurs when the astigmatism is canceled by the variable cross cylinder lens.

Also, in order to achieve the above-mentioned object, according to a thirteenth aspect of the present invention, there is provided an observation apparatus according to the twelfth aspect, being characterized in that the focusing position correction means is a correction lens group for changing a direction of positive or negative power produced by the variable cross cylinder lens to a direction of positive or negative power of the astigmatism, the group being composed of a plurality of correction lenses different from each other in spherical power.

Also, in order to achieve the above-mentioned object, according to a fourteenth aspect of the present invention, there is provided an observation apparatus according to any one of the first to thirteenth aspects further including a chromatic aberration canceling optical element for canceling chromatic aberration that occurs when the predetermined optical member is placed between the eye to be observed and the objective lens, the chromatic aberration canceling optical element being right and left independently respectively operable and provided between the variable lens system and the imaging lens on each of the right and left observation optical paths.

Also, in order to achieve the above-mentioned object, according to a fifteenth aspect of the present invention, there is provided an observation apparatus including: a variable lens system for changing an observation magnification for observing an eye to be observed, which is an observation object; and an imaging lens for imaging a light flux passing through the variable lens system, the variable lens system and the imaging lens being disposed on each of right and left observation optical paths between an objective lens opposed to the eye to be observed and eyepieces for right and left eyes, an observation optical path, which is for relaying a reflection light flux on the eye to be observed as a parallel light flux to the variable lens system, being formed between the objective lens and the variable lens system in each of the right and left observation optical paths, an observation optical path, which is for relaying the reflection light flux obtained through the variable lens system as a parallel light flux to the imaging lens, being formed between the variable lens system and the imaging lens in each of the right and left observation optical paths, the apparatus being characterized in that a chromatic aberration canceling optical element for canceling chromatic aberration that occurs when a predetermined optical member is placed between the eye to be observed and the objective lens, which is right and left independently operable respectively, is provided on each of the right and left observation optical paths.

Also, in order to achieve the above-mentioned object, according to a sixteenth aspect of the present invention, there is provided an observation apparatus according to the fifteenth aspect, being characterized in that the chromatic aberration canceling optical element includes: aberration direction setting means for setting a direction of the power of the chromatic aberration; and correction amount setting means for setting an amount of correction for canceling the power of the right and left chromatic aberration.

Also, in order to achieve the above-mentioned object, according to a seventeenth aspect of the present invention, there is provided an observation apparatus according to the fifteenth aspect, being characterized in that the predetermined optical member placed between the eye to be observed and the objective lens is a prism fit in contact with a cornea of the eye to be observed, and that the observation apparatus further includes: apex angle input means for inputting an apex angle of the prism; fitting angle input means for inputting a fitting angle of the prism to the cornea; and control means for controlling operation of the chromatic aberration canceling optical element based on the apex angle inputted by the apex angle input means and the fitting angle inputted by the fitting angle input means.

Also, in order to achieve the above-mentioned object, according to an eighteenth aspect of the present invention, there is provided an observation apparatus according to the seventeenth aspect, being characterized in that the control means controls operation of the chromatic aberration canceling optical element based on the observation magnification changed by the variable lens system.

Also, in order to achieve the above-mentioned object, according to a nineteenth aspect of the present invention, there is provided an observation apparatus according to any one of the fifteenth to eighteenth aspects further including: image receiving means for receiving an observation image of the eye to be observed from the reflection light flux on the eye to be observed, which is guided through one of the right and left observation optical paths; and fourth correction amount computing means for computing an amount of correction for canceling the chromatic aberration that occurs in the one of the right and left observation optical paths by performing predetermined analyzing processing on the observation image received by the image receiving means and then computing an amount of correction for canceling the chromatic aberration that occurs in the other of the right and left observation optical paths based on the computed correction amount, the apparatus being characterized in that the chromatic aberration canceling optical elements are right and left independently operated based on the amount of correction for the chromatic aberration in each of the right and left observation optical paths, which is computed by the fourth correction amount computing means.

Also, in order to achieve the above-mentioned object, according to a twentieth aspect of the present invention, there is provided an observation apparatus according to the seventeenth or eighteenth aspect further including: memory means for storing an amount of correction for canceling the chromatic aberration, corresponding to the apex angle of the prism and the fitting angle of the prism; image receiving means for receiving an observation image of the eye to be observed from the reflection light flux on the eye to be observed, which is guided through one of the right and left observation optical paths; and fourth correction amount computing means for computing an amount of correction for canceling the chromatic aberration that occurs in the one of the right and left observation optical paths by performing predetermined analyzing processing on the observation image received by the image receiving means and then computing an amount of correction for canceling the chromatic aberration that occurs in the other of the right and left observation optical paths based on the computed correction amount and the amount of correction for canceling the chromatic aberration, corresponding to the apex angle and the fitting angle, which is stored in the memory means, the apparatus being characterized in that the control means right and left independently controls the chromatic aberration canceling optical elements based on the amount of correction for the chromatic aberration in each of the right and left observation optical paths, which is computed by the fourth correction amount computing means.

Also, in order to achieve the above-mentioned object, according to a twenty first aspect of the present invention, there is provided an observation apparatus including: a variable lens system for changing an observation magnification for observing an eye to be observed, which is an observation object; an imaging lens for imaging a light flux passing through the variable lens system, the variable lens system and the imaging lens being disposed on each of right and left observation optical paths between an objective lens opposed to the eye to be observed and eyepieces for right and left eyes, an observation optical path, which is for relaying a reflection light flux on the eye to be observed as a parallel light flux to the variable lens system, being formed between the objective lens and the variable lens system in each of the right and left observation optical paths, an observation optical path, which is for relaying the reflection light flux obtained through the variable lens system as a parallel light flux to the imaging lens, being formed between the variable lens system and the imaging lens in each of the right and left observation optical paths; image receiving means for receiving right and left observation images of the eye to be observed from the reflection light fluxes on the eye to be observed, which are guided through the right and left observation optical paths; display means for displaying the right and left observation images received by the image receiving means; and chromatic aberration correcting means for correcting chromatic aberration in each of the right and left observation images by performing digital processing in which positions of point images of R, G, and B of each of the right and left observation images received by the image receiving means are aligned with one another on the display means, the point images being separated by the chromatic aberration that occurs when a predetermined optical member is placed between the eye to be observed and the objective lens.

DETAILED DESCRIPTION OF THE PREFERRED EMBODIMENTS

Hereinafter, examples of an observation apparatus according to embodiments of the present invention will be described in details with reference to the drawings. An operation microscope apparatus widely used particularly in an ophthalmologic field will be described below as the observation apparatus. An eye to be observed, which becomes an observation object is called an eye to be operated. Note that a typical structure of the present invention can be applied to a general observation apparatus for observing a state of the eye, such as a slit lamp microscope apparatus for observing an eye to be examined or (structural part for observing the eye to be examined, of) a photocoagulator for irradiating a fundus with laser light to perform treatment with photo-coagulation. The application of the present invention is not limited to the ophthalmologic field. When the same effect is obtained by applying the typical structure of the present invention to an observation apparatus for observing a part of a human body by using a microscope or the like, the present invention can be applied to the observation apparatus. In many situations, the observation apparatus according to the present invention is used with a state in which it is connected with an image processing apparatus for performing various image processings on an observation image or a monitor for displaying the observation image. Here, assume that the called "observation apparatus" includes an observation apparatus itself provided with an optical system for observation, an apparatus structure in which the image processing apparatus is connected with the observation apparatus, or a structure in which the monitor is further connected with the apparatus structure.

First Embodiment

Figure 1:
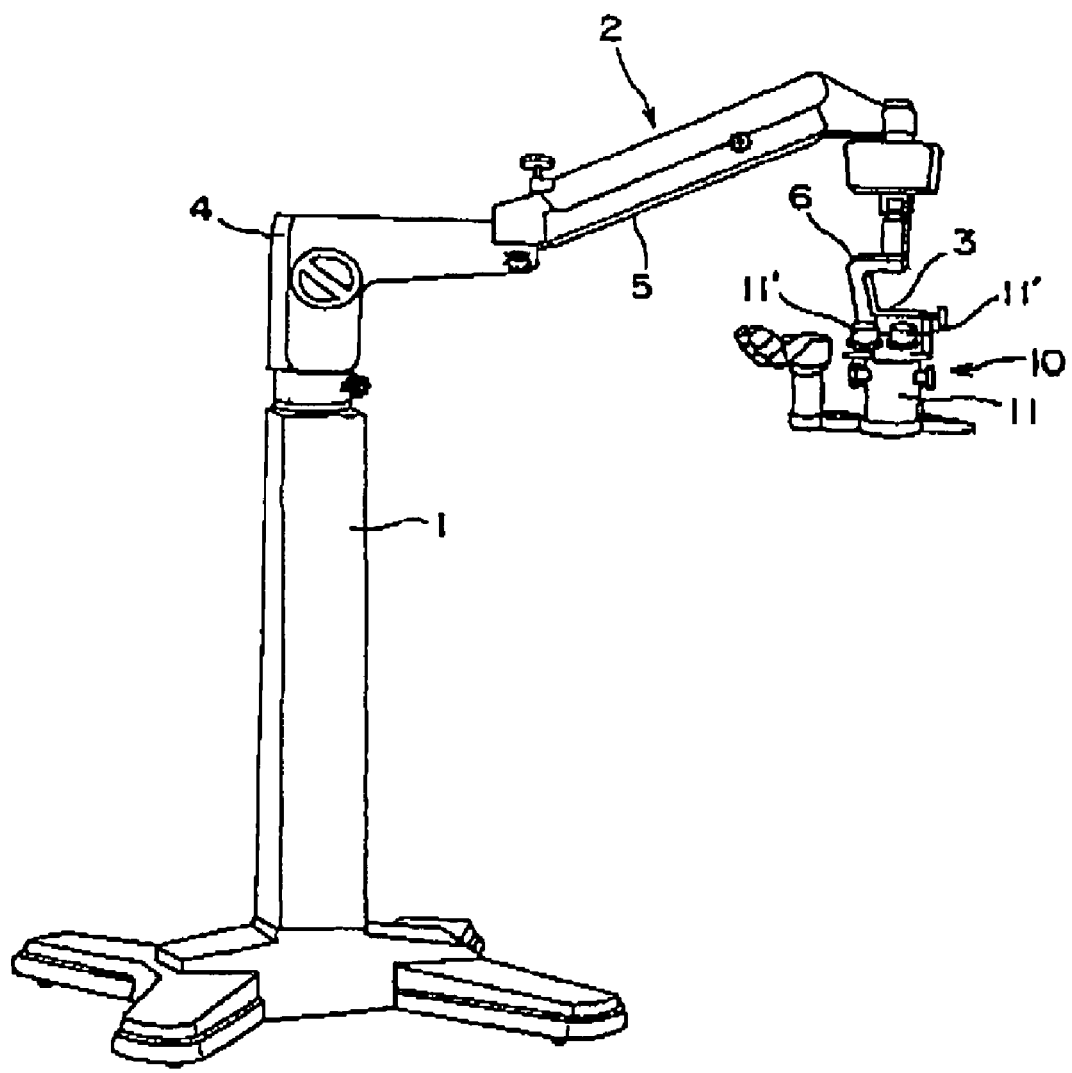
FIG. 1 is an external view showing a schematic structure of an operation microscope apparatus.
Figure 2:
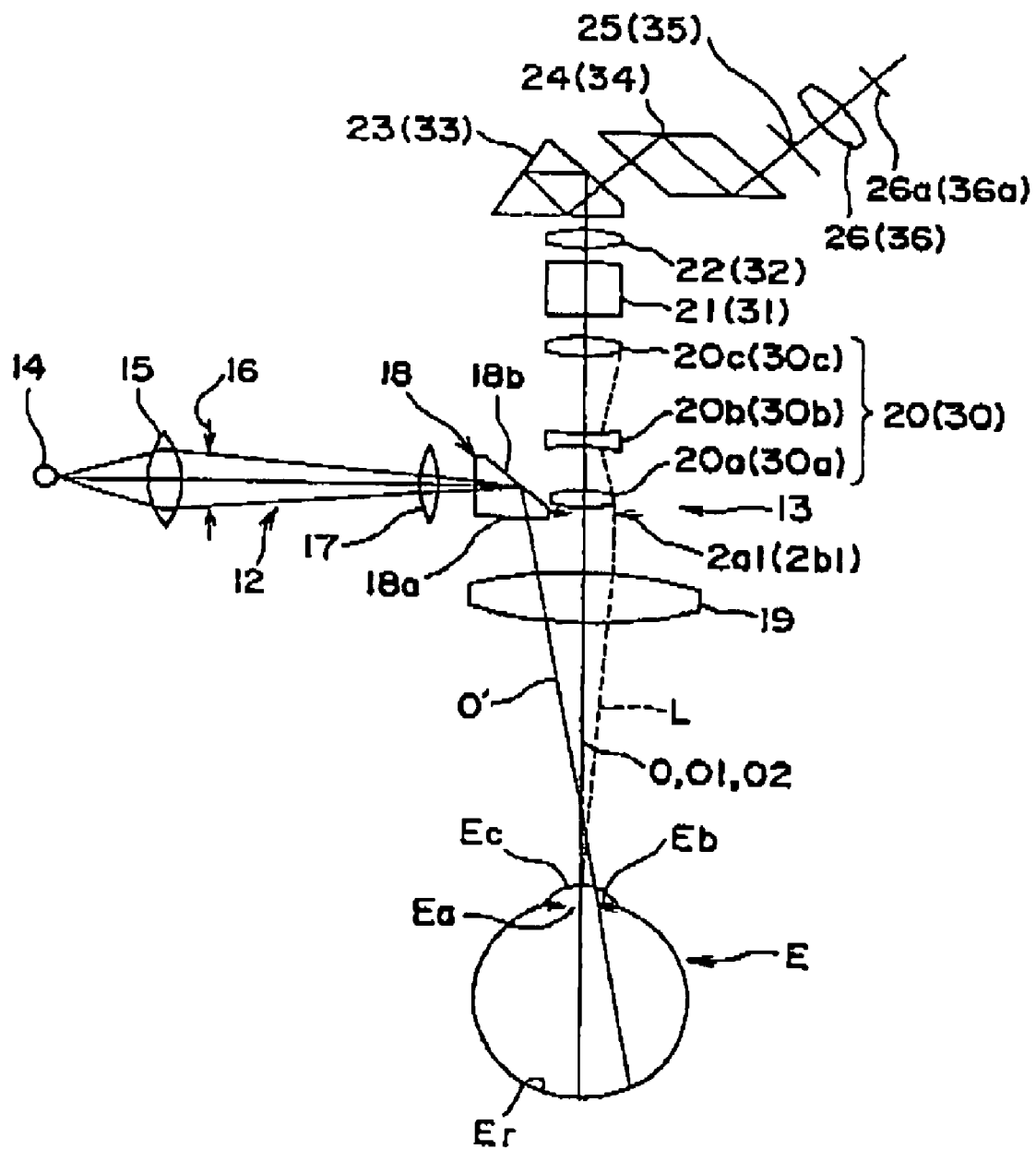
FIG. 2 is a side view showing a schematic structure of a conventional optical system of the operation microscope apparatus.
Figure 6:
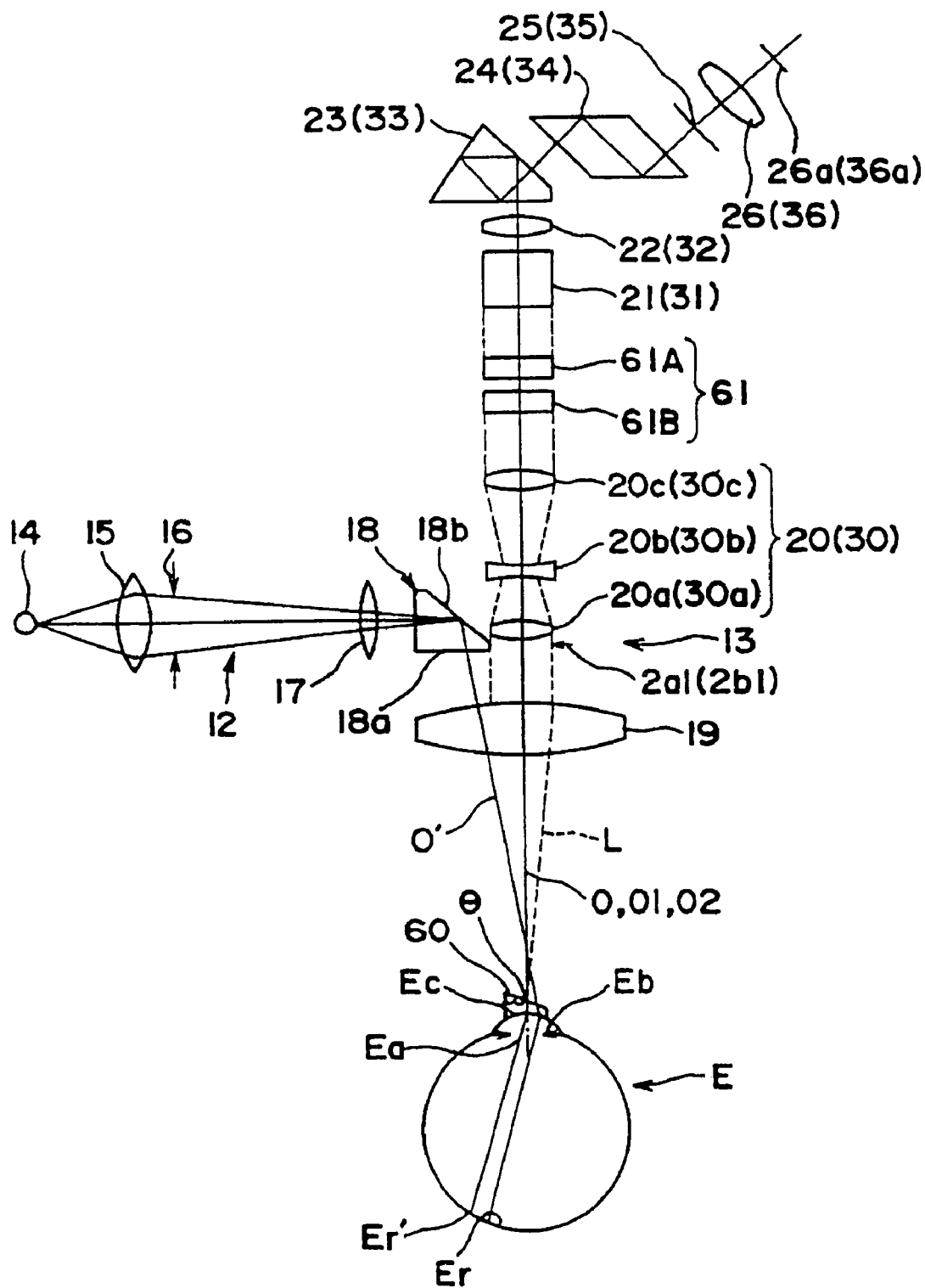
FIG. 6 is a side view showing a structure of an optical system of an observation apparatus according to a first embodiment of the present invention.
Figure 7:
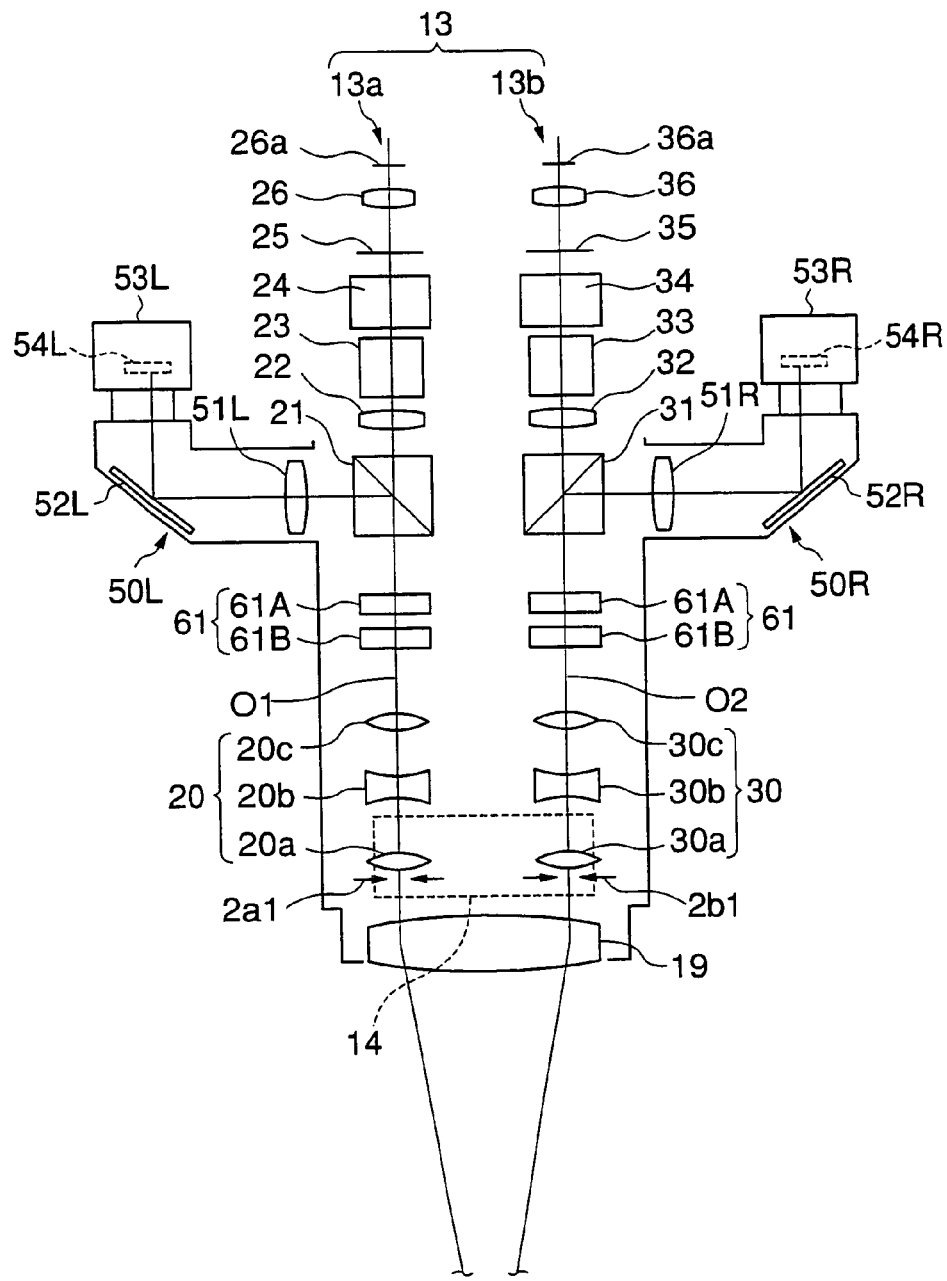
FIG. 7 is a front view showing the structure of the optical system of the observation apparatus according to the first embodiment of the present invention.

An operation microscope apparatus (observation apparatus) according to this embodiment has the external structure as shown in FIG. 1. Optical systems as shown in FIGS. 6 and 7 are disposed inside a lens barrel 11 of an operation microscope 10. In FIGS. 6 and 7, for descriptions the same references are provided to the same structural elements as in FIGS. 2 and 3, unless otherwise pointed out. In FIGS. 6, and 7, an auxiliary observation optical system for an operator's assistant is not shown. However, the auxiliary observation optical system can be provided by changing the structure of an optical system as appropriate. On the other hand, the structural elements different from those in FIGS. 2 and 3 will be intensively described below.

Structure of Optical System

In the left observation optical system 13a, an observation optical path for relaying reflection light on a fundus Eras a parallel light flux to a variable lens system 20 is formed between an objective lens 19 and the variable lens system 20. In addition, an observation optical path for relaying the reflection light obtained through the variable lens system 20 as a parallel light flux to an imaging lens 22 is formed between the variable lens system 20 and the imaging lens 22. In the right observation optical system 13b, an observation optical path for relaying reflection light on the fundus Er as a parallel light flux to a variable lens system 30 is formed between the objective lens 19 and the variable lens system 30. In addition, an observation optical path for relaying the reflection light obtained through the variable lens system 30 as a parallel light flux to an imaging lens 32 is formed between the variable lens system 30 and the imaging lens 32.

Here, an astigmatism canceling optical element 61 for canceling the power of astigmatism caused when a contact prism (prism in the present invention) 60 is put to a cornea Er of an eye to be operated E is provided between the variable lens system 20 (30) and the imaging lens 22 (32). A position of each astigmatism canceling optical element is generally an attachment position of a parallel optical type observation apparatus.

A zoom magnification of the variable lens system 20 is changed by changing relative positions among the lenses 20a, 20b, and 20c in an optical axis O1 direction by a drive mechanism which is not shown. Similarly, a magnification of the variable lens system 30 is changed by changing relative positions among the lenses 30a, 30b, and 30c in an optical axis O2 direction by a drive mechanism which is not shown.

Figure 8:
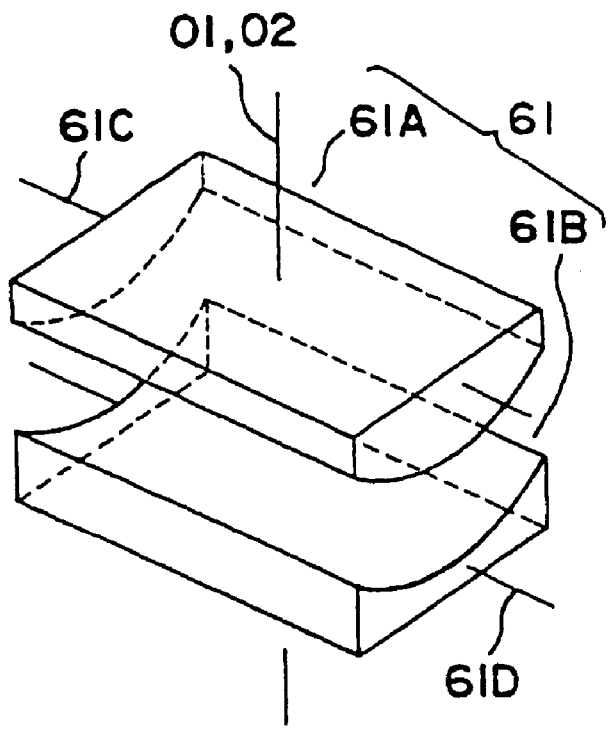
FIG. 8 is a perspective view showing an example of an astigmatism canceling optical element included in the optical system of the observation apparatus according to the first embodiment of the present invention, the element being in a state in which power is zero.
Figure 9:
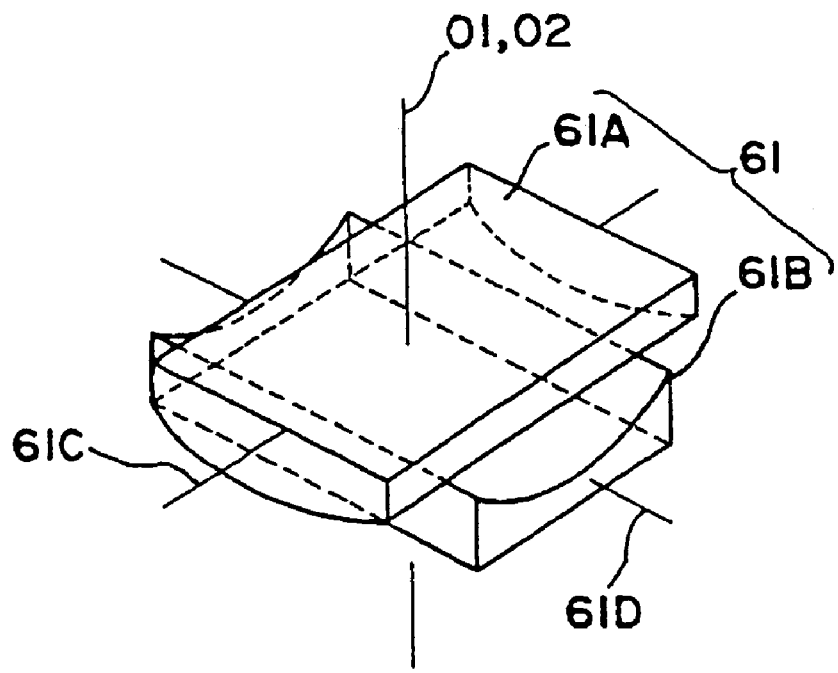
FIG. 9 is a perspective view showing an example of the astigmatism canceling optical element included in the optical system of the observation apparatus according to the first embodiment of the present invention, the element being in a state in which power is maximum.

As shown in FIGS. 8 and 9, the astigmatism canceling optical element 61 is a variable cross cylinder lens composed of a set of cylinder lenses 61A and 61B. The cylinder lens 61A is a convex cylinder lens and the cylinder lens 61B is a concave cylinder lens.

When a generating line axis 61C of the cylinder lens 61A is parallel to a generating line axis 61D of the cylinder lens 61B (the case of arrangement shown in FIG. 8), the power is 0 diopter. When the generating line axis 61C of the cylinder lens 61A is perpendicular to the generating line axis 61D of the cylinder lens 61B (the case of arrangement shown in FIG. 9), the power becomes maximum.

The cylinder lenses 61A and 61B are integrally rotatable and relatively rotatable about the observation axes O1 and O2. When the cylinder lenses 61A and 61B are integrally rotated about the observation axes O1 and O2, the astigmatism canceling optical element 61 can be fit to the orientation of astigmatism changed according to a putting manner of the contact prism 60 to the eye to be operated E. With a state in which the orientation of the astigmatism canceling optical element 61 is hold, when the cylinder lenses 61A and 61B are relatively rotated to change the power of the astigmatism canceling optical element 61 as appropriate, the astigmatism caused when the contact prism 60 is put to the eye to be operated E can be cancelled.

Figure 10:
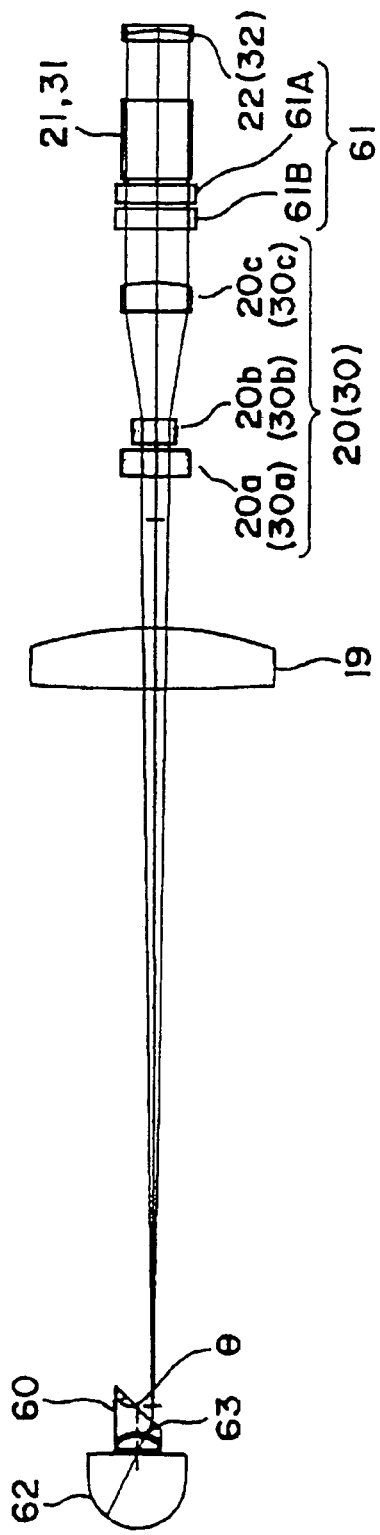
FIG. 10 is a schematic optical view for explaining an operation of the astigmatism canceling optical element included in the optical system of the observation apparatus according to the first embodiment of the present invention.

FIG. 10 is an explanatory view using a model eye, showing an example of such an operation of the astigmatism canceling optical element 61. Reference numeral 62 denotes a fundus corresponding portion of the model eye and 63 denotes a cornea corresponding portion thereof. FIG. 10 shows a state in which the contact prism 60 having an apex angle θ of 45 degrees is put to the cornea corresponding portion 63. In FIG. 10, a focal distance "f" of the objective lens 19 is set to 200 mm and an observation magnification of the imaging lens 22 (32) (based on the variable lens system 20 (30)) is set to 4.2. The power of the astigmatism canceling optical element 61 for canceling the astigmatism caused in the case of such set conditions is −0.017 diopters.

When the astigmatism canceling optical element 61 is not used, an observation image of a point image projected to the fundus corresponding portion 62 is changed from a state of a longitudinal ellipse to a state of a transverse ellipse through a state of a minimum circle with changing a focusing state of the observation image of the point image from the front side of a focusing position to the rear side thereof, thereby distorting the observation image. Therefore, the sharpness of the observation image deteriorates. In order to eliminate such a state, when the above-mentioned power is added by the astigmatism canceling optical element 61, the astigmatism is canceled to correct the distortion of the observation image, so that the sharpness thereof can be improved.

When the observation magnification of the imaging lens 22 (32) is set to 6.3, the power of the astigmatism canceling optical element 61 for canceling the astigmatism is −0.043 diopters. When the observation magnification is set to 10.5, the power of the astigmatism canceling optical element 61 for canceling the astigmatism is −0.11 diopters. When the observation magnification is set to 16, the power of the astigmatism canceling optical element 61 for canceling the astigmatism is −0.284 diopters. When the observation magnification is set to 21, the power of the astigmatism canceling optical element 61 for canceling the astigmatism is −0.445 diopters.

As shown in FIG. 7, a TV image pickup system 50L is provided in the left observation optical system 13a and a TV image pickup system 50R is provided in the right observation optical system 13b. A part of observation light guided by the observation optical systems 13a (13b) is reflected by a beam splitter 21 (31) and incident on the TV image pickup system 50L (50R). Therefore, the image of the eye to be operated E can be taken.

The TV image pickup system 50L of the left observation optical system 13a is an optical system for taking the image of the eye to be operated E, which is viewed by the left eye of the operator. The TV image pickup system 50L is composed of an imaging lens 51L, a reflecting mirror 52L, and a TV camera 53L. The TV camera 53L includes a CCD image pickup element 54L serving as an image receiving unit. The TV image pickup system 50R of the right observation optical system 13b is an optical system for taking the image of the eye to be operated E, which is viewed by the right eye of the operator. The TV image pickup system 50R is composed of an imaging lens 51R, a reflecting mirror 52R, and a TV camera 53R. The TV camera 53R includes a CCD image pickup element 54R serving as an image receiving unit. Although the details are described later, the TV image pickup systems 50L and 50R are connected with an image processing apparatus for performing predetermined digital processing on respective images taken by the TV image pickup systems 50L and 50R.

Structure of Control Panel

Figure 11:
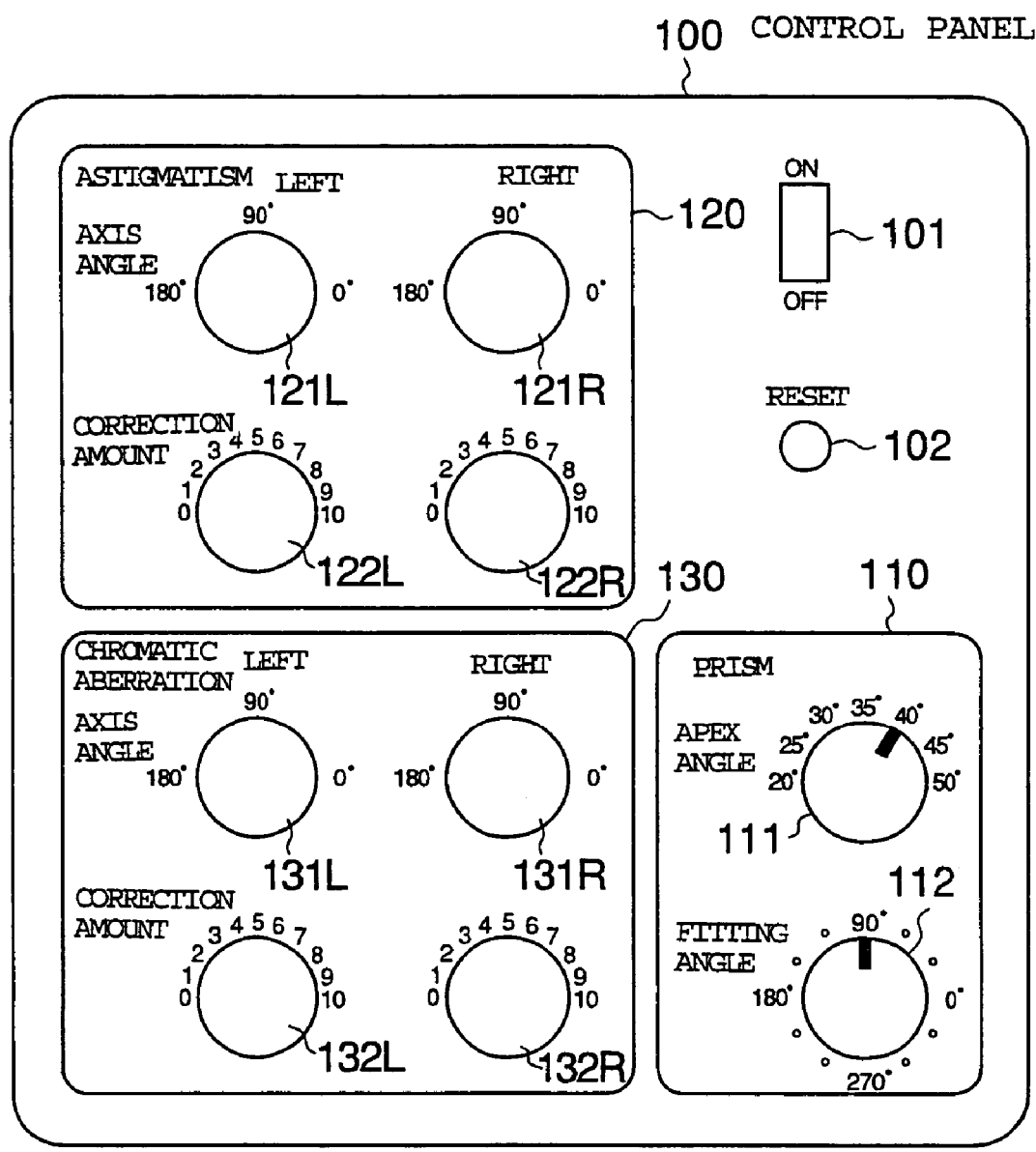
FIG. 11 is a schematic view showing a control panel provided on the observation apparatus according to the first embodiment of the present invention.

FIG. 11 shows a control panel 100 for performing various settings and operations for an astigmatism canceling function described later (and chromatic aberration canceling function which will be described in a third embodiment), of the observation apparatus according to this embodiment. The control panel 100 is provided on, for example, the lens barrel 11 of the operation microscope 10 such that the operator can operate the control panel 100 while observing the eye to be examined.

The control panel 100 includes: an ON/OFF switch 101 for switching between ON/OFF of the astigmatism canceling function (and chromatic aberration canceling function) of the observation apparatus; a reset button 102 for resetting various settings for the functions; a prism setting portion 110 for performing settings related to the contact prism 60 placed in contact with the cornea Ec of the eye to be operated E; an astigmatism setting portion 120 for performing settings for correcting the astigmatism caused by the contact prism 60; and a chromatic aberration setting portion 130 for performing settings for correcting the chromatic aberration caused by the contact prism 60. The chromatic aberration setting portion 130 will be described in detail in the description of an observation apparatus according to the third embodiment of the present invention. Here, a switch for switching between ON/OFF of the astigmatism canceling function and a switch for switching between ON/OFF of the chromatic aberration canceling function may be provided instead of the ON/OFF switch 101. A changing switch for switching between the astigmatism canceling function and the chromatic aberration canceling function may be provided.

The prism setting portion 110 includes: an apex angle setting knob 111 for setting the apex angle θ of the used contact prism 60 (apex angle input unit in the present invention): and a fitting angle setting knob 112 for setting an angle at which the contact prism 60 is fit onto the cornea Er (fitting angle input unit in the present invention). The operator rotates the apex angle setting knob 111 to set the apex angle θ of the used contact prism 60 to, for example, 20° to 50°. In addition, the operator rotates the fitting angle setting knob 112 to set a prism base direction of the fit contact prism 60. Assume that 0° is set as the fitting angle when the prism base direction is located on the right side as viewed from the operator side and the fitting angle increases counter-clockwise.

The astigmatism setting portion 120 includes: knobs for performing setting operation related to the astigmatism canceling optical element 61 of the left observation optical system 13a: and knobs for performing setting operation related to the astigmatism canceling optical element 61 of the right observation optical system 13b. The former knobs are an axial angle setting knob 121L for setting an axial angle of the astigmatism canceling optical element 61 of the left observation optical system 13a (aberration direction setting unit) and a correction amount setting knob 122L for setting the amount of astigmatism to be corrected by the astigmatism canceling optical element 61 of the left observation optical system 13a (correction amount setting unit). The latter knobs are an axial angle setting knob 121R for setting an axial angle of the astigmatism canceling optical element 61 of the right observation optical system 13b (aberration direction setting unit) and a correction amount setting knob 122R for setting the amount of astigmatism to be corrected by the astigmatism canceling optical element 61 of the right observation optical system 13b (correction amount setting unit).

The axial angles set by the axial angle setting knobs 121L and 121R are generally adjusted such that the axial angles are (substantially) equal to the angle related to the prism base direction, which is set by the fitting angle setting knob 112 on the prism setting portion 110. Therefore, it is possible to set the above-mentioned axial angles in conjunction with setting of the fitting angle setting knob 112. A changing switch capable of selectively switching between such automatic axial angle setting and manual axial angle setting using the axial angle setting knobs 121L and 121R may be provided.

Angles can be indicated around the fitting angle setting knob 112 and the axial angle setting knobs 121L and 121R while an arbitrary direction is set as 0°. In this embodiment, the right side in the lateral direction as viewed from the operator side is set as 0° and an angle increases counter-clockwise.

Numerals 0 to 10 indicated around the correction amount setting knobs 122L and 122R are marks indicating the relative degrees of power (correction amount) produced by the astigmatism canceling optical element 61. The power of 0 diopter is set as a mark of 0 and the maximum power is set as a mark of 10.

Structure of Control System

Figure 12:
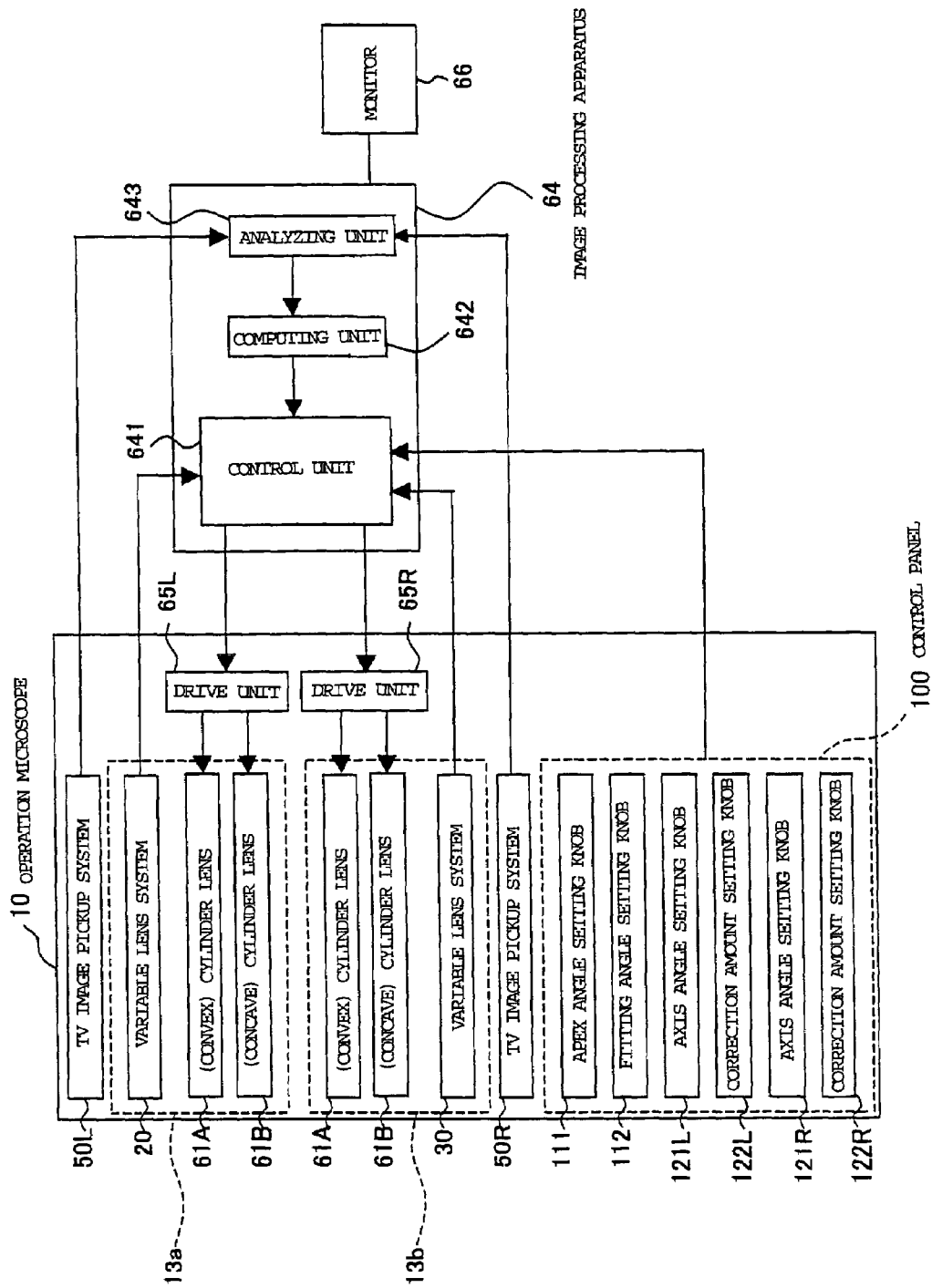
FIG. 12 is a block diagram showing a control system of the observation apparatus according to the first embodiment of the present invention.

FIG. 12 is a block diagram showing a structure of a control system of the observation apparatus according to this embodiment. As shown in FIG. 12, the observation apparatus includes an image processing apparatus 64 that performs various analyzing processing and various computing processing on fundus images of the eye to be operated E, which are received by the CCD image pickup elements 54L and 54R of the TV image pickup systems 50L and 50R, display processing of images on a monitor 66 (display unit in the present invention), and processings such as generation and transmission of control signals for controlling the operation of the observation apparatus. The image processing apparatus 64 includes a computing control device composed of a CPU and the like and a memory device (such as a ROM or a hard disk drive). The computing control device operates according to programs stored in the memory device, thereby performing the above-mentioned processings. A separate image processing apparatus may be provided for each of the TV image pickup systems 50L and 50R.

The image processing apparatus 64 includes a control unit 641, a computing unit 642, and an analyzing unit 643 according to the present invention. Each of these units is composed of the computing control device operated according to the programs stored in the memory device. The control unit 641 performs processings such as generation and transmission of various control signals and recognition of an observation magnification based on each of the variable lens systems 20 and 30. The analyzing unit 643 performs predetermined analyzing processing (described later) on the fundus images of the eye to be operated E which are taken by the TV image pickup systems 50L and 50R. The computing unit 642 calculates the amount of correction (described later) for canceling the power of astigmatism caused by the contact prism 60 based on an analyzed result of the analyzing unit 643. It is also possible to utilize a structure in which the operation microscope apparatus includes the respective units. Here, the analyzing unit 643 and the computing unit 642 compose a first correction amount computing unit in the present invention.

The operation microscope 10 of the observation apparatus includes: a variable cross cylinder lens rotating drive unit 65L for rotating the cylinder lenses 61A and 61B composing the astigmatism canceling optical element 61 of the left observation optical system 13*a* about the observation optical axis O1; and a variable cross cylinder lens rotating drive unit 65R for rotating the cylinder lenses 61A and 61B composing the astigmatism canceling optical element 61 of the right observation optical system 13*b* about the observation optical axis O2. The variable cross cylinder lens rotating drive units 65L and 65R are separately operated by the control unit 641 of the image processing apparatus 64. Each of the variable cross cylinder lens rotating drive units 65L and 65R can be composed of, for example, a stepping motor. The variable cross cylinder lens rotating drive units 65L and 65R compose a drive unit in the present invention and are shown as "drive units" in FIG. 12.

The observation magnification for the eye to be operated E based on each of the variable lens systems 20 and 30 is recognized by the control unit 641 of the image processing apparatus 64. Such recognition is performed in accordance with signals from a drive system (not shown) for operating the variable lens systems 20 and 30. An observation magnification may be recognized based on a signal inputted when the observation magnification is set.

When the control panel 100 is operated, an operating signal is transmitted to the control unit 641.

Use Mode

Use modes of the observation apparatus having the above-mentioned structure according to this embodiment will be described. According to the observation apparatus in this embodiment, various use modes can be performed as described below. Note that it is unnecessary to use a structure in which all the following use modes can be performed. A structure in which at least one of the use modes can be performed may be used. In this time, it is unnecessary to include structural parts used in unemployed use modes. When a structure in which a plurality of use modes can be selectively performed is used, a changing switch for switching between the respective use modes can be provided in, for example, the control panel 100.

USE EXAMPLE 1

Figure 13:
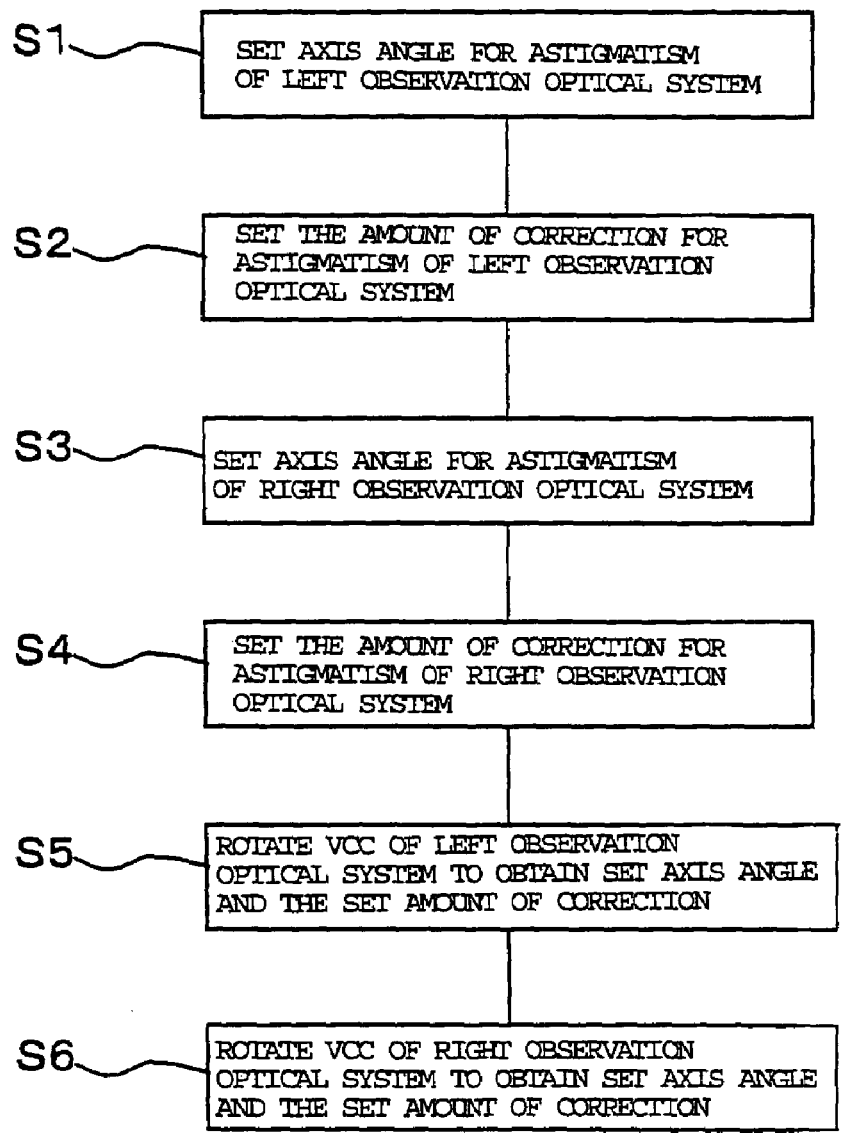
FIG. 13 is a flow chart showing an example of a use mode of the observation apparatus according to the first embodiment of the present invention.

A use mode in the case of manual use will be described with reference to a flow chart shown in FIG. 13. First, setting is performed using the astigmatism setting portion 120 on the control panel 100. More Specifically, the axial angle for the astigmatism of the left observation optical system 13*a*, that is, a direction in which power is added to correct the astigmatism is set by rotating the axial angle setting knob 121L (Step S1). In addition, the amount of correction for the astigmatism of the left observation optical system 13*a* is set by rotating the correction amount setting knob 122L (Step S2). Similarly, the axial angle for the astigmatism of the right observation optical system 13*b* is set by rotating the axial angle setting knob 121R (Step S3). In addition, the amount of correction for the astigmatism of the right observation optical system 13*b* is set by rotating the correction amount setting knob 122R (Step S4). It is needless to say that the setting operation related to the left observation optical system 13*a* or the setting operation related to the right observation optical system 13*b* may be performed first.

After the above-mentioned setting operations are performed using the control panel 100, signals related to the setting operations are sent to the control unit 641 of the image processing apparatus 64. The control unit 641 controls the variable cross cylinder lens rotating drive unit 65L to rotate the cylinder lenses 61A and 61B composing the variable cross cylinder lens 61 (abbreviated to "VCC" in FIG. 13) of the left observation optical system 13*a* so as to obtain the set axial angle and the set amount of correction (Step S5). Simultaneously, the control unit 641 controls the variable cross cylinder lens rotating drive unit 65R to rotate the cylinder lenses 61A and 61B of the right observation optical system 13*b* so as to obtain the set axial angle and the set amount of correction (Step S6).

Thus, the astigmatism caused by the contact prism 60 which is put to the eye to be operated E is corrected, so that the observation image can be preferably viewed. In particular, the amount of correction and the like can be set for each of the right and the left. Therefore, even in the case where the amount of aberrations in the right and the left are different from each other, such as the case where the fundus surroundings Er' is observed, the image can be normally stereoscopically viewed. When the astigmatism is not sufficiently removed by performing correction once, the operator can operate the control panel 100 to perform further correction.

USE EXAMPLE 2

Figure 14:
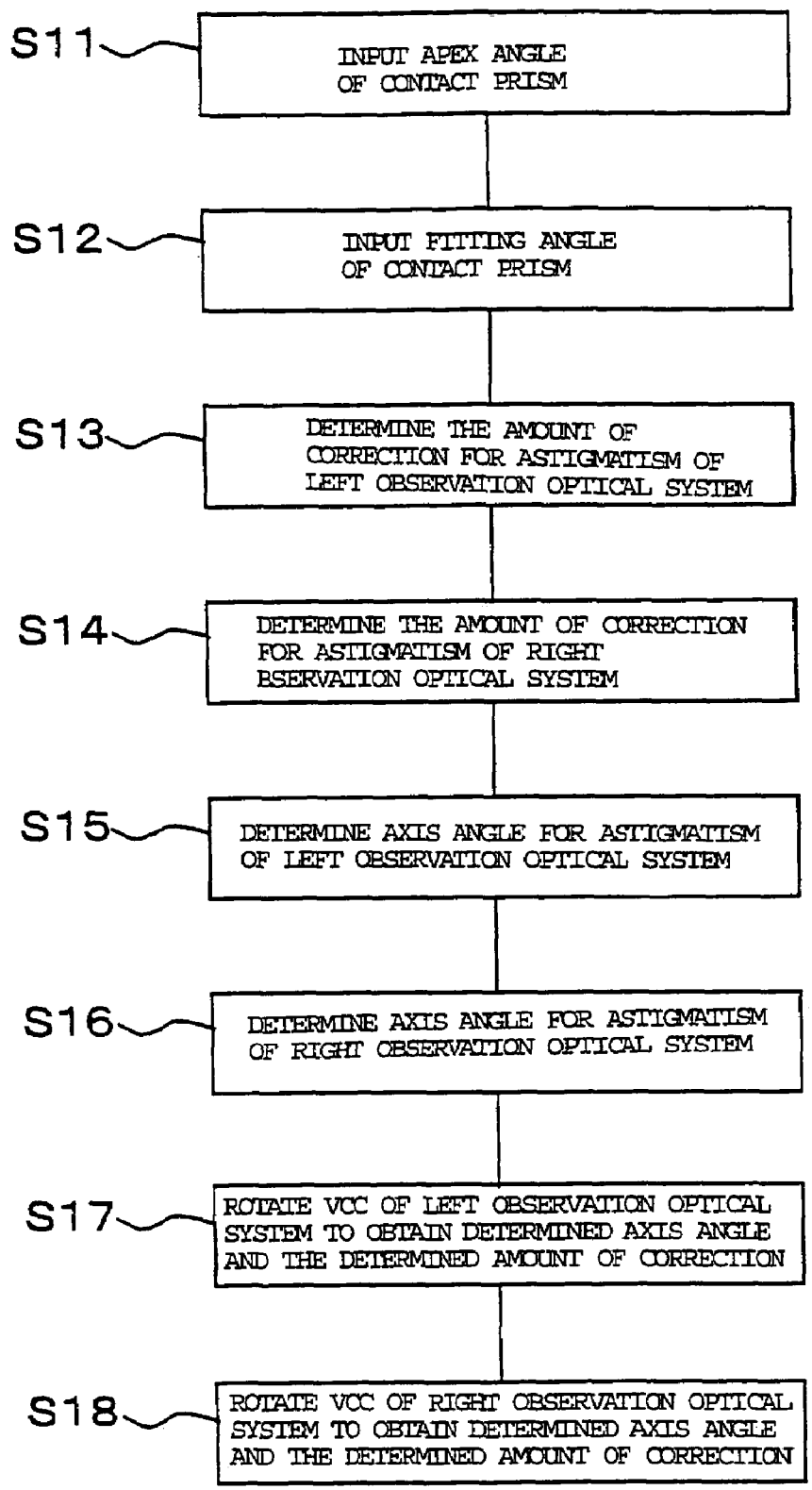
FIG. 14 is a flow chart showing an example of a use mode of the observation apparatus according to the first embodiment of the present invention.

Next, another use mode of the observation apparatus according to this embodiment will be described with reference to a flow chart shown in FIG. 14. In this use mode, only conditions of the contact prism 60 which is put to the eye to be operated E are inputted instead of setting the axial angle for the astigmatism and the amount of correction thereof, so that the operation becomes easier.

First, the apex angle θ of the contact prism 60 which is put to the eye to be operated E is inputted by rotating the apex angle setting knob 111 of the prism setting portion 110 on the control panel 100 (Step S11). The fitting angle of the contact prism 60 is inputted by rotating the fitting angle setting knob 112 (Step S12). The input contents are transmitted as signals to the control unit 641 of the image processing apparatus 64.

Determination data for determining the power of the astigmatism canceling optical element 61 based on the apex angle θ of the contact prism 60 are stored in advance in the memory device of the image processing apparatus 64. For example, data which are obtained by performing a test using the model eye as described above on each of the prepared contact prisms 60 and associated with the observation magnification based on each of the variable lens systems 20 and 30 can be used as the determination data. In this time, a test is performed in each of the case where the position of the observation optical axis to the contact prism 60 is set to the position of the observation optical axis O1 of the left observation optical system 13*a* and the case where the position of the observation optical axis to the contact prism 60 is set to the position of the observation optical axis O2 of the right observation optical system 13*b*, and then results are stored.

The control unit 641 recognizes the observation magnification based on each of the variable lens systems 20 and 30. Then, the control unit 641 determines the amount of correction for the astigmatism of the left observation optical system 13*a* (Step S13) and the amount of correction for the astigmatism of the right observation optical system 13*b* (Step S14) with reference to the above-mentioned determination data based on the recognized observation magnification and the apex angle θ inputted in Step S11. Further, the control unit 641 determines the axial angle for the astigmatism of the left observation optical system 13*a* and the axial angle for the astigmatism of the right observation optical system 13*b* based on the fitting angle of the contact prism 60 which is inputted in Step S12 (Steps S15 and S16). It may be determined that, for example, the fitting angle is equal to the axial angles.

After the determinations of the amount of correction and the axial angle, the control unit 641 controls the variable cross cylinder lens rotating drive unit 65L to rotate the cylinder lenses 61A and 61B of the left observation optical system 13a so as to obtain the determined axial angle and the determined amount of correction (Step S17). In addition, the control unit 641 controls the variable cross cylinder lens rotating drive unit 65R to rotate the cylinder lenses 61A and 61B of the right observation optical system 13b so as to obtain the determined axial angle and the determined amount of correction (Step S18).

USE EXAMPLE 3

Next, another use mode of the observation apparatus according to this embodiment will be described. In this use mode, the astigmatism correction is automatically performed based on the observation images related to the right and the left, which are received by the CCD image pickup elements 54L and 54R of the TV image pickup systems 50L and 50R.

Figure 15:
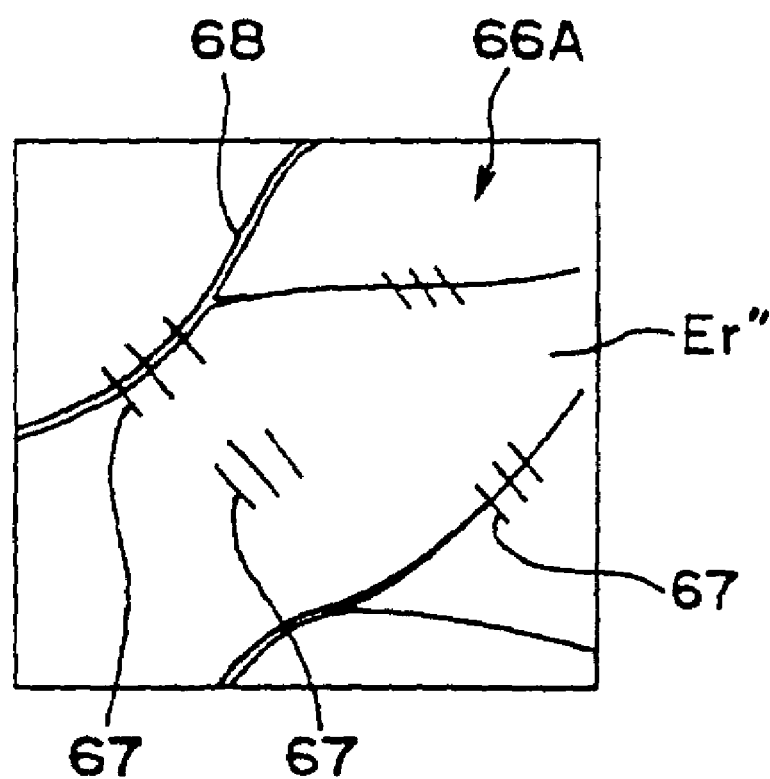
FIG. 15 shows a fundus image before astigmatism correction, which schematically shows a state in which a flow is produced on a screen because of astigmatism caused by a contact prism.

The respective observation images observed through the left observation optical system 13a and the right observation optical system 13b are displayed on a screen 66A of the monitor 66. FIG. 15 is a schematic view showing the fundus image Er" including the fundus surroundings Er', which is displayed on the monitor 66 (in which only the observation image observed through the left observation optical system 13a is shown for the sake of simplification). When the astigmatism is caused by the contact prism 60, a flow of image 67 occurs as schematically shown in FIG. 15. For example, an image of a contour of a blood vessel 68 appears to flow. In this use mode, the flow of image 67 resulting from the astigmatism is corrected by executing the following processing.

Figure 16:
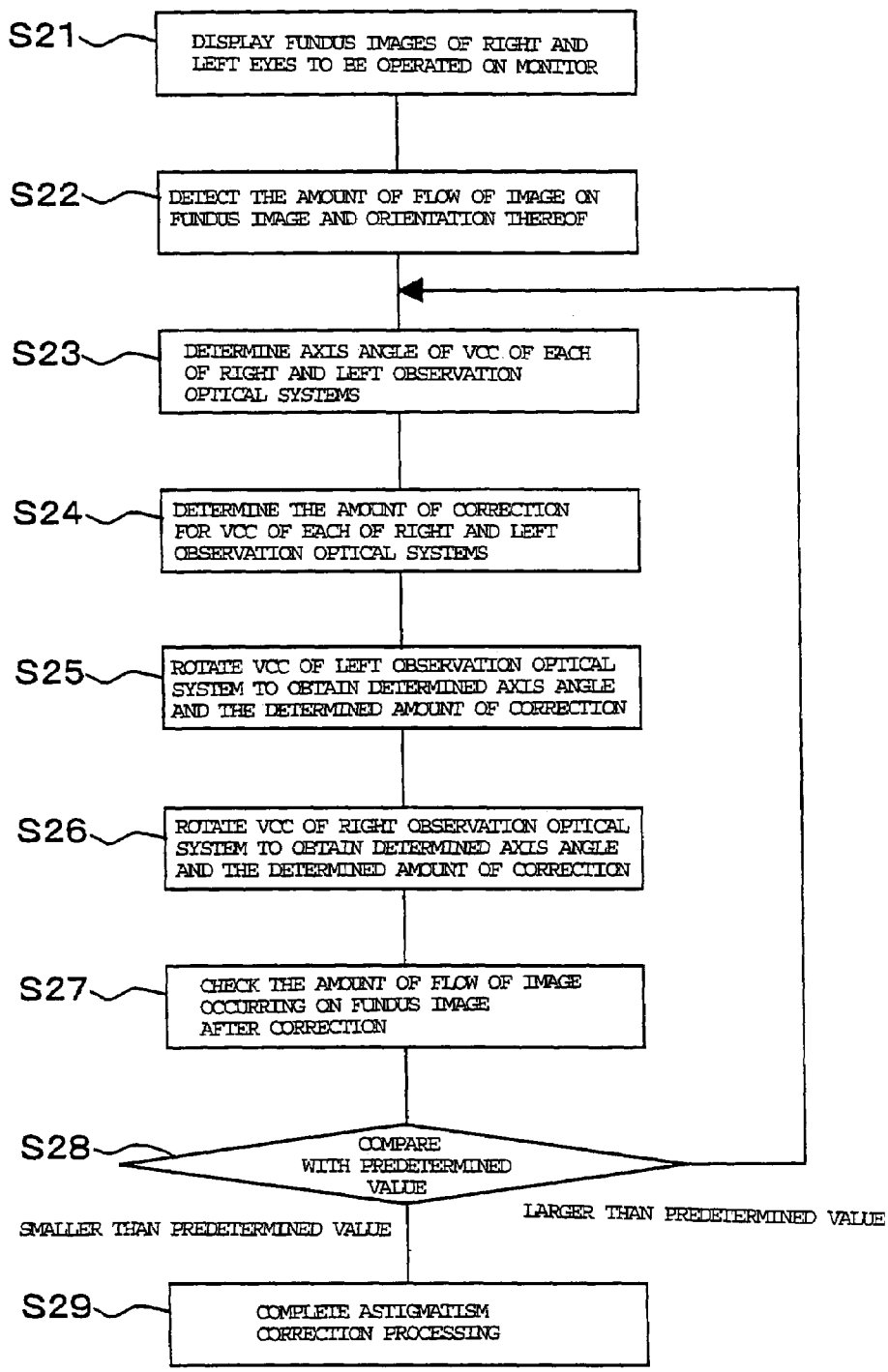
FIG. 16 is a flow chart showing an example of a use mode of the observation apparatus according to the first embodiment of the present invention.

FIG. 16 is a flow chart showing processing in this use mode. First, fundus images Er" obtained through the left and right observation optical systems 13a and 13b are displayed on the monitor 66 (Step S21). The analyzing unit 643 extracts the flow of image 67 of the contour of the blood vessel 68 from each of the fundus images Er" and analyzes the flow of image 67 to detect a direction of the flow and the amount of flow (Step S22).

Next, the computing unit 642 determines the axial angle and the power (the amount of correction) of the cylinder lenses 61A and 61B for each of the left observation optical systems 13a and the right observation optical systems 13b based on the detected direction of the flow of image 67 and the detected amount of flow of image 67 with respect to the contour of the blood vessel 68 (Steps S23 and S24). More specifically, the computing unit 642 performs the following processing. The axial angle is set as an orientation different from the orientation of the flow of image 67 by 45°. The amount of correction is set corresponding to the amount of flow of image 67.

Then, the control unit 641 generates control signals for rotating the cylinder lenses 61A and 61B with respect to the determined axial angle and the determined amount of correction and transmits the control signals to the variable cross cylinder lens rotating drive units 65L and 65R. The variable cross cylinder lens rotating drive units 65L and 65R rotate the cylinder lenses 61A and 61B of each of the left and right observation optical systems 13a and 13b based on the received control signals (Steps S25 and S26). More specifically, the cylinder lenses 61A and 61B are integrally rotated in an orientation different from an orientation corresponding to the flow of image 67 of the contour of the blood vessel 68 by 45°. Each of the generating line axes of the cylinder lenses 61A and 61B is held to the different orientation and then the cylinder lenses 61A and 61B are relatively rotated according to the amount of flow of image 67. Therefore, a diopter having power for canceling the astigmatism is set in the astigmatism canceling optical element 61.

Figure 17:
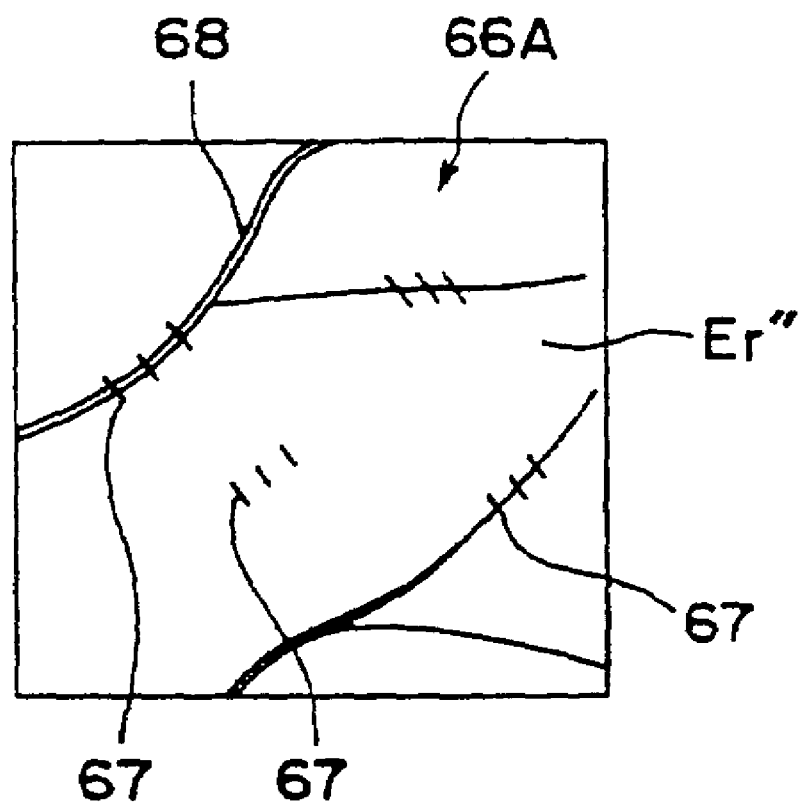
FIG. 17 shows a fundus image obtained by correcting the astigmatism by the use mode shown in FIG. 16, which schematically shows a state in which the amount of flow on the screen becomes smaller.

According to such processings, the flow of image 67 which is caused on each of the observed fundus images is corrected, so that the amount of flow of image 67 of the contour of the blood vessel 68 becomes smaller as shown in FIG. 17.

Next, the remaining amount of flow of image 67 on each of the fundus images after the correction is checked (Step S27). In other words, the analyzing unit 643 again analyzes the remaining amount of flow of image 67 (and the direction thereof). The computing unit 642 calculates the amount of flow of image 67 (and the direction thereof). The control unit 641 compares the calculated amount of flow of image 67 with a predetermined value that is preset. Note that the predetermined value is set as a threshold value for sufficiently clearing the fundus image.

When the remaining amount of flow of image 67 is larger than the predetermined value, the cylinder lenses 61A and 61B of each of the left and right observation optical systems 13a and 13b are controlled based on the amount of flow of image 67 (and the direction thereof) which is calculated in Step S27 (Steps S23 to S26). Then, the remaining amount of flow of image 67 is checked again (Step S27) and the comparison with the predetermined value is performed (Step S28). Such processings are repeated until the remaining amount of flow of image 67 becomes smaller than the predetermined value. When the amount of flow of image 67 becomes smaller than the predetermined value, the astigmatism correction processing is completed (Step S29).

Although not shown in the drawing, a correction lens (group) for correcting a positive or negative spherical power error caused by the cylinder lenses 61A and 61B may be provided in each of the left and right observation optical systems 13a and 13b to generate the power for reducing the remaining amount of flow of image 67.

The positive or negative spherical power error caused by the cylinder lenses 61A and 61B may be corrected by using the control panel 100.

According to this use mode in which the above-mentioned processings are executed, the astigmatism is automatically corrected without performing setting operation and input operation, so that the operability can be improved. In particular, the automatic correction is performed without depending on the apex angle θ and the fitting angle of the contact prism 60, the observation magnification, and the like, so that the convenience becomes higher. When the above-mentioned predetermined value is adequately set, a sharp image can be automatically obtained. Therefore, this use mode can be also applied to the case where eye operation is performed with very high precision. The fundus images observed through the left and right observation optical systems 13a and 13b can be separately corrected for the left and the right, adequate stereoscopic viewing is possible.

MODIFIED EXAMPLE

Figure 18:
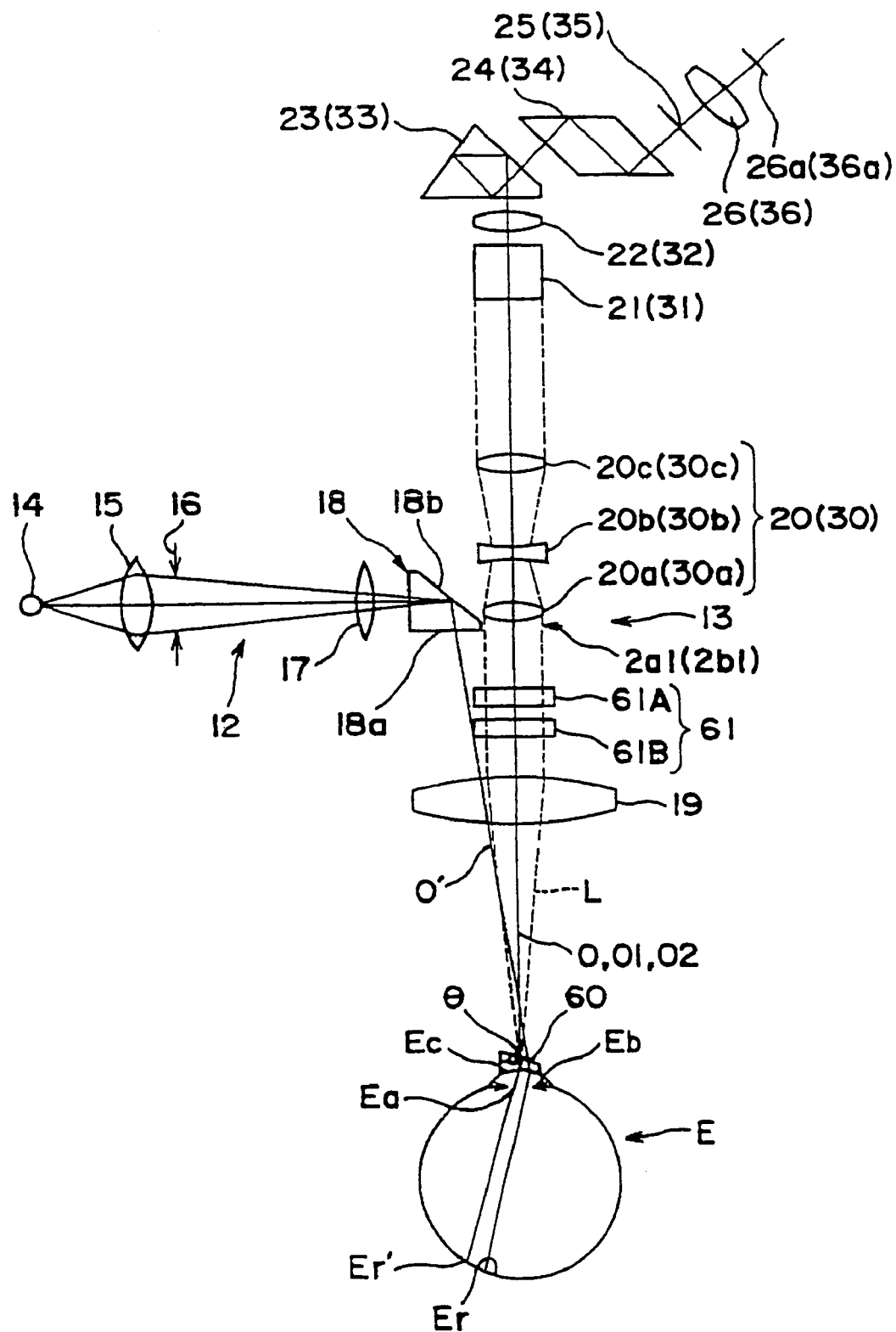
FIG. 18 is a side view showing a structure of an optical system of the observation apparatus as a modified example of the first embodiment of the present invention.

FIG. 18 shows a structure of an optical system included in a modification of the observation apparatus described as the first embodiment. The modified example has a structure in which the astigmatism canceling optical element 61 is disposed between the objective lens 19 and the variable lens system 20 (30).

In this modified example, the astigmatism canceling optical element 61 is provided between the objective lens 19 and the variable lens system 20 (30) on the observation optical path for relaying a reflection light flux on the fundus Er in parallel. Therefore, even if the power of the astigmatism canceling optical element 61 is not changed according to the observation magnification, the astigmatism can be canceled without being affected by a change in magnification, so that it is convenient for handling.

As in the modified example, the astigmatism canceling optical element 61 is disposed between the objective lens 19 and the variable lens system 20 (30) on the observation optical path for relaying the reflection light flux on the fundus Er in parallel. Alternatively, as in the first embodiment, the astigmatism canceling optical element 61 is disposed on the observation optical path for relaying in parallel the reflection light flux on the fundus Er which is obtained through the variable lens system 20 (30) to the imaging lens 22 (32). Therefore, the astigmatism can be canceled without depending on an interval between the cylinder lenses 61A and 61B, so that the astigmatism can be easily canceled. Note that the astigmatism canceling optical element 61 can be disposed at an arbitrary position on the observation path of each of the left and right observation optical systems 13a and 13b from the objective lens 19 to the eyepiece 26 (36).

In this embodiment, the variable cross cylinder lens composed of the convex cylinder lens 61A and the concave cylinder lens 61B is used as the astigmatism canceling optical element 61. In addition, the astigmatism can be canceled by, for example, an Alvarez lens. The Alvarez lens is composed of a pair of lenses, which are relatively movable and can separately generate desirable spherical power and desirable cylindrical power according to relative moving directions of those. When the Alvarez lens is used, it is unnecessary to provide the above-mentioned correction lens (group). Note that, when the moving directions of the pair of lenses composing the Alvarez lens are limited by the limitation of a design of the apparatus, the correction lens may be provided to correct the spherical power error.

Second Embodiment

Hereinafter, an observation apparatus according to a second embodiment of the present invention will be described. Note that the same references are provided to the same structural elements as in the first embodiment for the description.

Structure

The observation apparatus according to this embodiment includes the same optical systems as the observation apparatus according to the first embodiment. The same control panel 100 is provided on the observation apparatus according to this embodiment.

Figure 19:
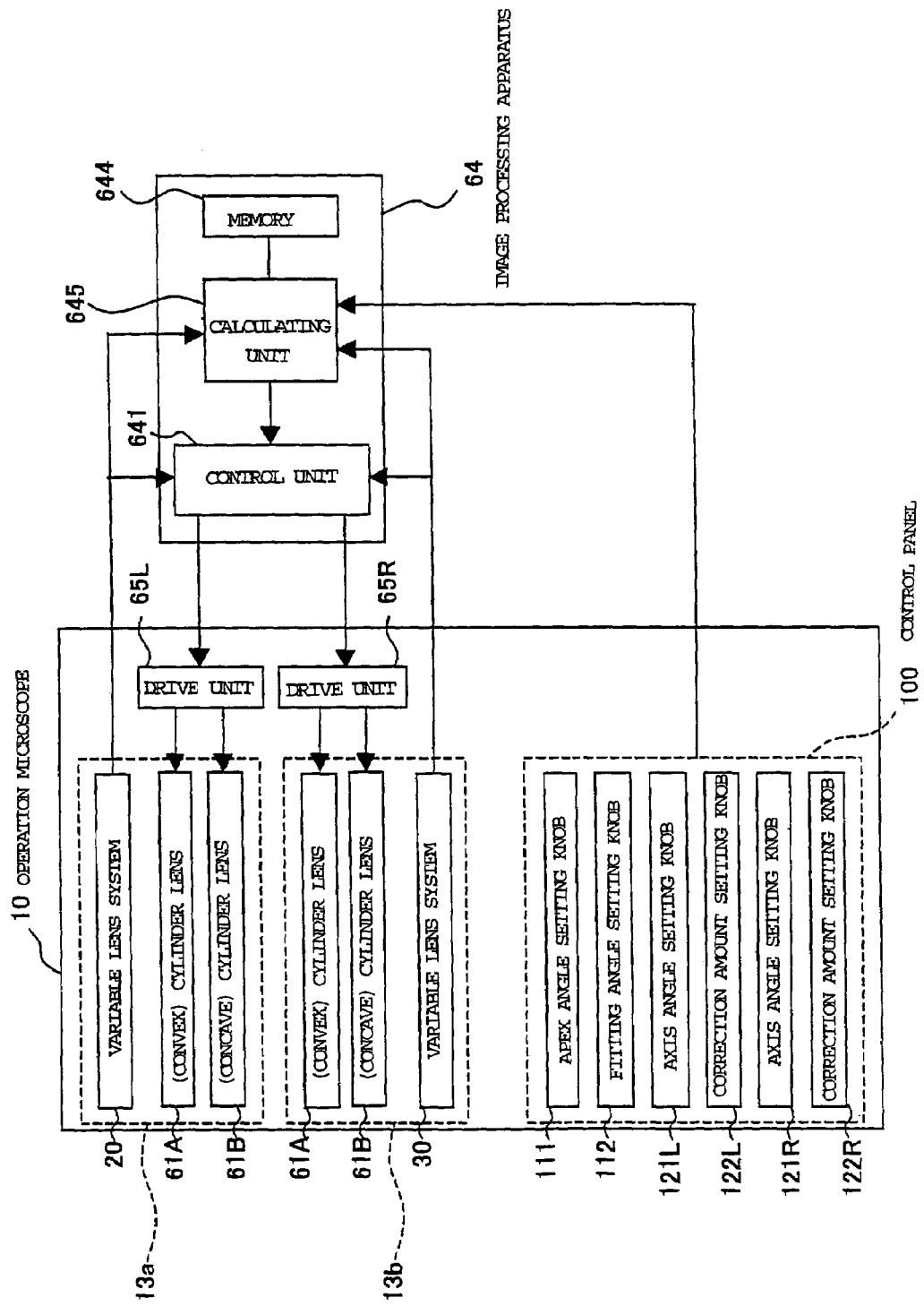
FIG. 19 is a block diagram showing a control system of an observation apparatus according to a second embodiment of the present invention.
Figure 20:
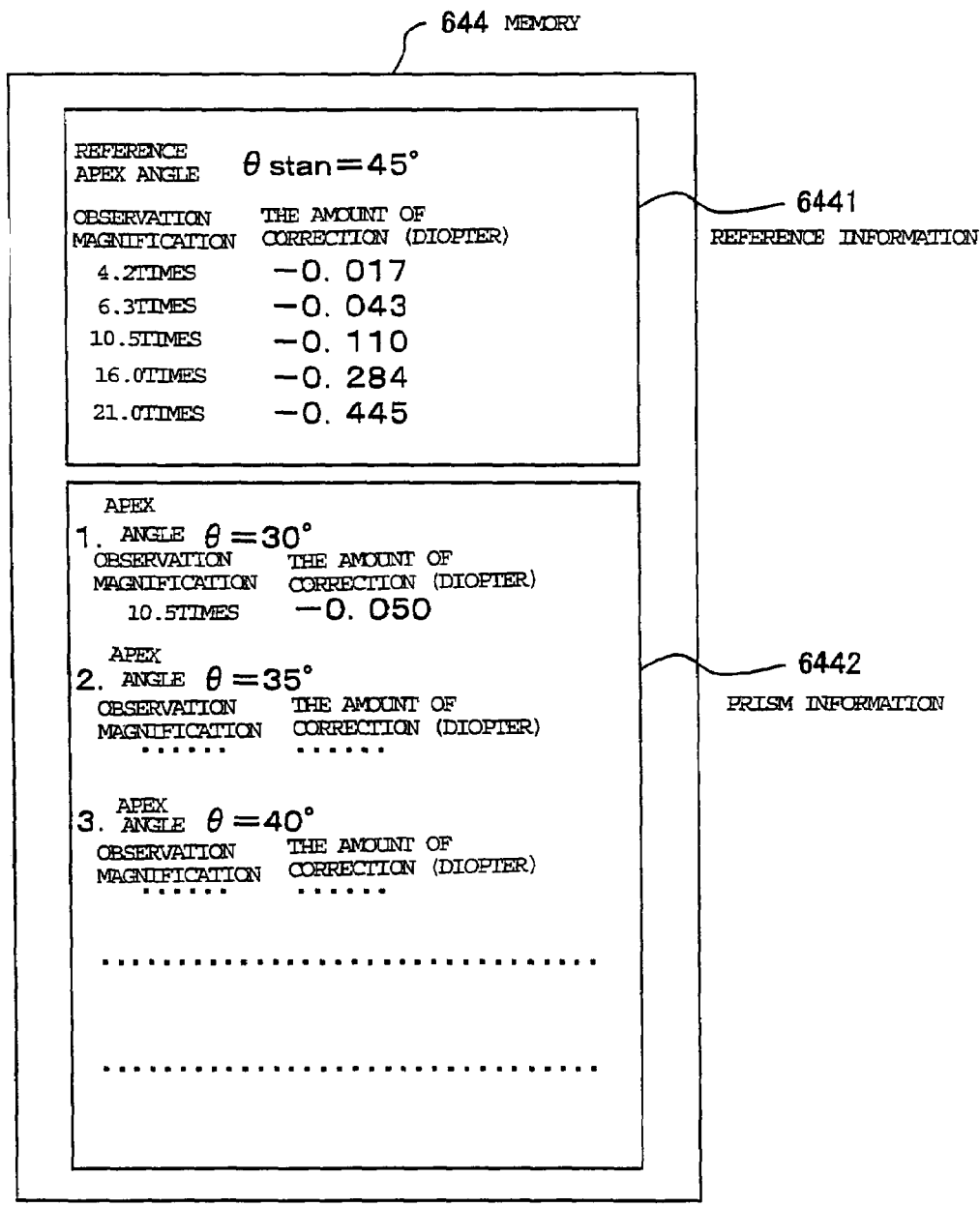
FIG. 20 schematically shows an example of information stored in a memory composing the observation apparatus according to the second embodiment of the present invention.

FIG. 19 is a block diagram showing a structure of a control system of the observation apparatus according to this embodiment. The image processing apparatus 64 shown in FIG. 19 includes the control unit 641, a memory 644, and a calculating unit 645. The control unit 641 has the same function as in the first embodiment. The memory 644 is a memory unit such as a ROM or a hard disk drive in the present invention and stores information as shown in FIG. 20 later. Note that the memory device described in the first embodiment may be commonly used. The calculating unit 645 calculates the amount of correction for astigmatism according to the observation magnification based on each of the variable lens systems 20 and 30, the apex angle θ of the fit contact prism 60, and the information stored in the memory 644. The calculating unit 645 is composed of a CPU executing predetermined operating programs, and the like. The memory 644 is not necessarily included in the image processing apparatus 64 and may be an external memory device. It may be constructed such that reading of an information recording medium such as a CD-ROM or a floppy (registered trademark) disk, in which the same information is recorded is performed using a drive of the image processing apparatus 64.

FIG. 20 is a schematic view showing an example of information stored in the memory 644 in advance. Reference information 6441 and prism information 6442 as described in detail below are stored in the memory 644. The reference information 6441 is composed of data in which power (the amount of correction) for canceling astigmatism caused by a contact prism (hereinafter referred to as a reference prism) having a predetermined apex angle θstan serving as a reference (hereinafter abbreviated to a reference apex angle) is associated with various observation magnifications. The prism information 6442 is composed of the amount of correction for canceling astigmatism caused by a contact prism having one of various apex angles θ at a specific observation magnification (which may be a single magnification). The reference information and the prism information can be obtained through, for example, a test using the model eye described in the first embodiment.

The reference information 6441 shown in FIG. 20 includes correction values for canceling the astigmatism caused by the reference prism having the reference apex angle θstan of 45°. More specifically, the reference information 6441 includes data in which the amount of correction when an observation magnification based on each of the variable lens system 20 and 30 is set to 4.2 is −0.017 diopters, the amount of correction when the observation magnification is set to 6.3 is −0.043 diopters, the amount of correction when the observation magnification is set to 10.5 is −0.11 diopters, the amount of correction when the observation magnification is set to 16 is −0.284 diopters, and the amount of correction when the observation magnification is set to 21 is −0.445 diopters. Note that the reference apex angle θstan of the reference prism is not necessarily 45° and can be set to an arbitrary apex angle. In addition, the above-mentioned observation magnifications are not necessarily set.

The prism information 6442 includes the amount of correction to an observation magnification for each of the apex angles θ of various contact prisms, which are prepared for operation (in 5° increments in FIG. 20). For example, in the case of the contact prism having the apex angle θ of 30°, the amount of correction for canceling the astigmatism caused when the observation magnification is 10.5 is −0.05 diopters.

Use Mode

Figure 21:
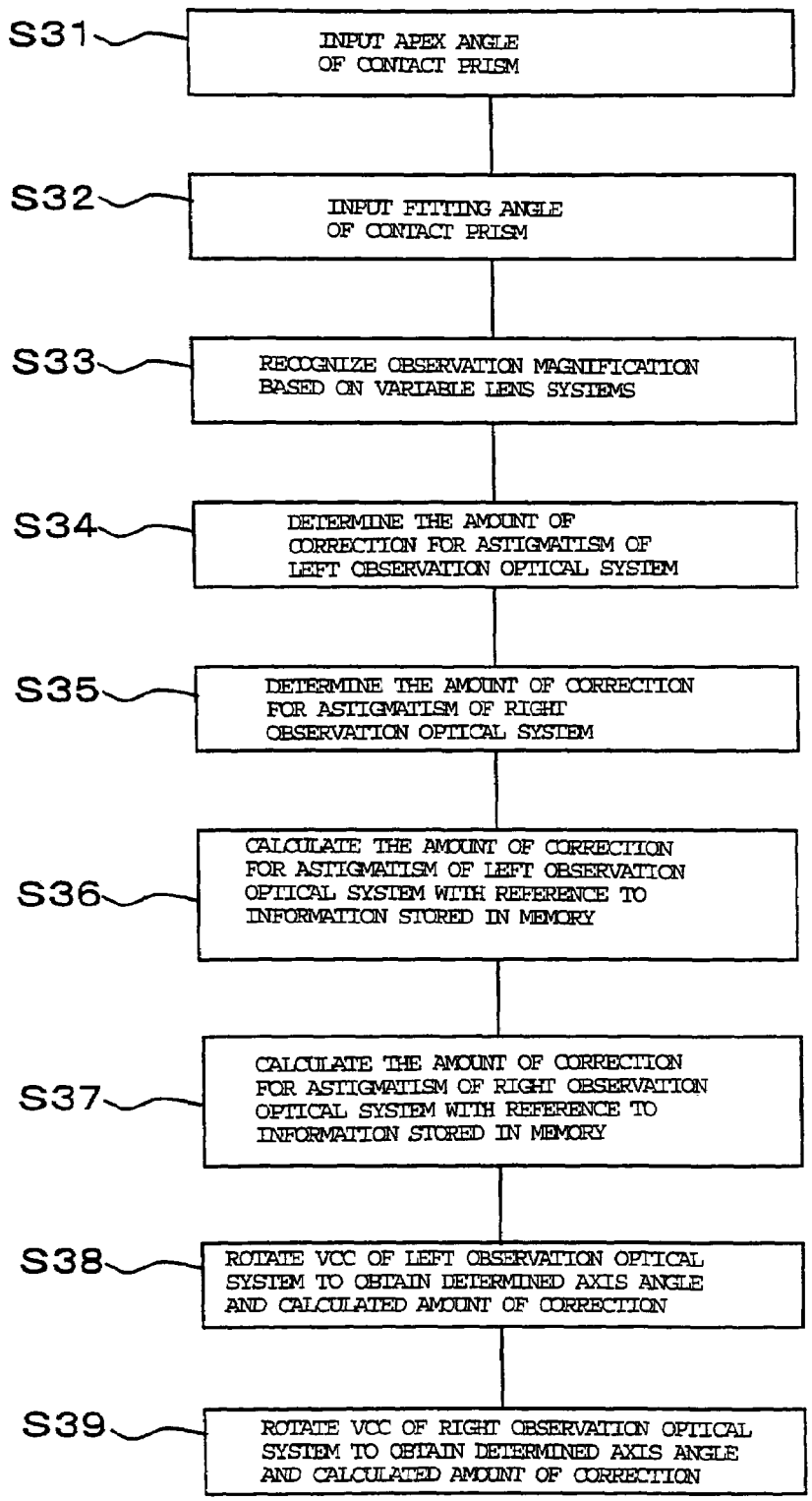
FIG. 21 is a flow chart showing an example of a use mode of the observation apparatus according to the second embodiment of the present invention.
Figure 22:
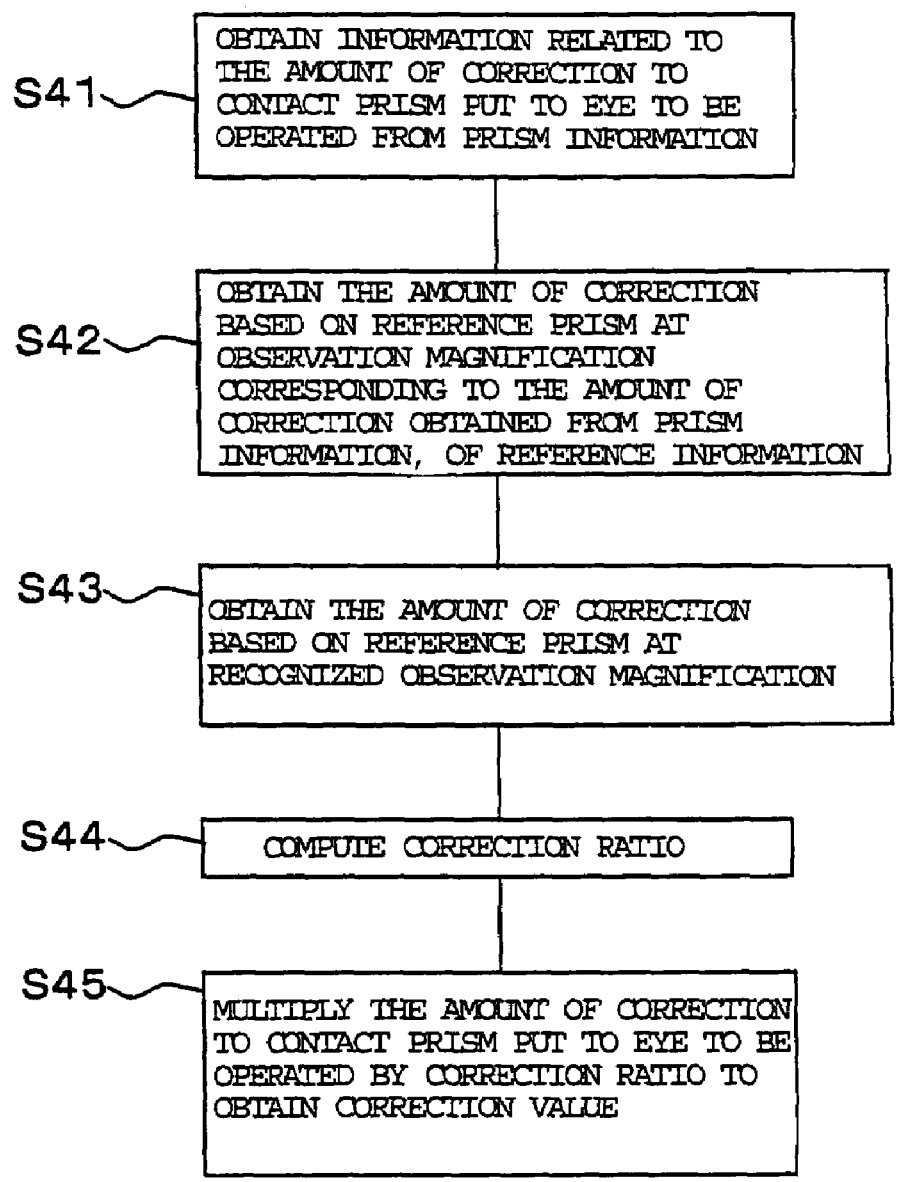
FIG. 22 is a flow chart showing an example of a use mode of the observation apparatus according to the second embodiment of the present invention.

Hereinafter, an example of a use mode of the observation apparatus having the above-mentioned structure according to this embodiment will be described with reference to flow charts shown in FIGS. 21 and 22. The flow chart shown in FIG. 22 is a specific explanatory diagram showing processings, which are performed in Steps S36 and S37 of the flow chart shown in FIG. 21.

First, the apex angle θ of the contact prism 60 which is put to the eye to be operated E is inputted by rotating the apex angle setting knob 111 of the prism setting portion 110 on the control panel 100 (Step S31). The fitting angle of the contact prism 60 is inputted by rotating the fitting angle setting knob 112 (Step S32). The input contents are transmitted as signals to the calculating unit 645 of the image processing apparatus 64.

The control unit 641 recognizes the observation magnification based on each of the variable lens systems 20 and 30 (Step S33). Then, the control unit 641 determines the axial angle for the astigmatism of the left observation optical system 13a and the axial angle for the astigmatism of the right observation optical system 13b based on the fitting angle of the contact prism 60 which is inputted in Step S32 (Steps S34 and S35).

The calculating unit 645 calculates the amount of correction for the astigmatism of the left observation optical system 13a (Step S36) and the amount of correction for the astigmatism of the right observation optical system 13b (Step S37) with reference to the information stored in the memory 644 based on the apex angle θ of the contact prism 60 which is inputted in Step S31 and the observation magnification recognized in Step S33. For example, the calculation of the amount of correction is performed as follows (see FIG. 22). Here, assume that the apex angle of the contact prism 60 which is Put to the eye to be operated E is 30° and the observation magnification recognized in Step S33 is 21.

First, the calculating unit 645 obtains information related to the amount of correction to the contact prism 60 having the apex angle of 30° from the prism information 6442 stored in the memory 644 (Step S41). More specifically, as shown in FIG. 20, the amount of correction when the observation magnification is 10.5 is −0.050 diopters. Next, the calculating unit 645 obtains the amount of correction based on the reference prism at the observation magnification corresponding to the amount of correction obtained from the prism information 6442, of the reference information 6441 stored in the memory 644 (Step S42). In this example, the amount of correction based on the reference prism at the observation magnification of 10.5 is −0.110 diopters. Further, the calculating unit 645 obtains the amount of correction (−0.445 diopters) based on the reference prism at the recognized observation magnification of 21 (Step S43).

Then, the calculating unit 645 compares the amount of correction at the observation magnification of 10.5 with the amount of correction at the observation magnification of 21 and computes a ratio of the amount of correction at the magnification of 21 to the amount of correction at the magnification of 10.5 (hereinafter referred to as a correction ratio) (Step S44). In this example, the correction ratio is −0.445/−0.110=4.04545 . . . , so that the correction ratio becomes about 4.

Following this, the calculating unit 645 multiplies the amount of correction to the contact prism 60 which is obtained in Step S41 by the correction ratio computed in Step S44 to obtain a product correction value and then completes the calculation of the amount of correction (Step S45). In this example, the product correction value is −0.050×4 and thus becomes −0.200 diopters. Therefore, the calculating unit 645 composes a correction amount calculating unit in the present invention. Note that a value obtained by rounding off the product correction value in the first decimal place is used here. Another approximate value can be used as appropriate. Hereinafter, FIG. 21 will be referred to again.

After the determinations of the amount of correction and the axial angle, the control unit 641 controls the variable cross cylinder lens rotating drive unit 65L based on the results in Steps S34 and S36 to rotate the cylinder lenses 61A and 61B of the left observation optical system 13a so as to obtain the determined axial angle and the calculated amount of correction (Step S38). Similarly, the control unit 641 controls the variable cross cylinder lens rotating drive unit 65R based on the results in Steps S35 and S37 to rotate the cylinder lenses 61A and 61B of the right observation optical system 13b so as to obtain the determined axial angle and the calculated amount of correction (Step S39).

According to the observation apparatus according to this embodiment, which is constructed so as to perform the above-mentioned astigmatism correction processing, when the amount of correction to the contact prism having the apex angle different from the reference apex angle of the reference prism at a specific observation magnification is obtained, the amount of correction related to other observation magnifications are calculated. The astigmatism is automatically corrected using the calculated results, so that it is possible to perform speedy correction processing. In addition, when the reference information 6441 and the prism information 6442 which are related to each of the left and right observation optical systems 13a and 13b are stored in advance and the respective right and left astigmatism canceling optical elements 61 are separately controlled, the adequate stereoscopic viewing is possible.

Note that the correction ratio to the each observation magnification may be included in the reference information 6441 stored in the memory 644. Therefore, the computing processing of the correction ratio (Step S44) in the flow chart shown in FIG. 22 is not necessarily performed, so that it is possible to perform more speedy processing.

MODIFIED EXAMPLE

Hereinafter, a modified example of the observation apparatus according to this embodiment will be described. In this modified example, the prism information 6442 is not stored in advance in the memory 644 but the prism information 6442 is set by an operator his/herself or the like during the operation. Such a manner is particularly suitable to an operator or the like skilled in correcting astigmatism. Therefore, it is possible to perform adequate correction processing based on power of an individual eye to be operated. In addition, it is unnecessary to input the apex angle and the fitting angle of the contact prism put to the eye to be operated, so that the control panel 100 may be omitted.

Though not shown, the observation apparatus of this modified example has a structure in which the monitor 66 is added to the structure shown in FIG. 19 (for example, see FIG. 12). Only the reference information 6441 shown in FIG. 20 is stored in advance in the memory 644 of the image processing apparatus 64, although not shown.

In this modified example, when the contact prism 60 having the apex angle different from the reference apex angle θstan is put to the eye to be examined E, an operator or the like operates the image processing apparatus 64 to rotate the astigmatism canceling optical elements 61 of the left and right observation optical systems 13a and 13b about the observation optical axes O1 and O2 to set the power for canceling the astigmatism at a specific observation magnification, while viewing the screen 66A of the monitor 66 (for example, see FIG. 15).

For example, assume that the apex angle θ of the contact prism 60 is 30° and the observation magnification when the power is set is 10.5. The power set at this time is assumed to be −0.05 diopters.

When the observation magnification is changed by the operator (fitting angle is not changed), the control unit 641 recognizes the changed observation magnification. Here, the observation magnification is changed to 21. Hereinafter, the description will be made based on such a numerical example.

Then, the calculating unit 645 obtains, from the reference information 6441 stored in the memory 644, correction values to the reference prism having the reference apex angle θstan of 45°, that is, a correction value of −0.110 diopters at the observation magnification of 10.5 and a correction value of −0.445 diopters at the observation magnification of 21. When the observation magnification is 21, the calculating unit 645 computes a necessary correction ratio indicating a multiple of the correction value at the observation magnification of 10.5. Here, the correction ratio is about 4.

Further, the calculating unit 645 calculates, based on the computed correction ratio, the amount of correction required for the astigmatism canceling optical element 61 when the contact prism 60 having the apex angle of 30° is put to the eye to be operated E and the observation magnification is set to 21. That is, the power of −0.05 diopters which is set when the observation magnification is 10.5 is multiplied by the correction ratio of 4 to obtain the amount of correction of −0.2 diopters.

When the fitting angle is changed together with the observation magnification, for example, the following two use modes can be used. In a first use mode, when the control panel 100 is provided, the fitting angle setting knob 112 may be rotated to set the fitting angle of the contact prism 60 and the axial angle of the cylinder lenses 61A and 61B may be set based on the set fitting angle. In a second use mode, when the control panel 100 is not used (when the control panel is not provided), the axial angle may be manually adjusted.

Third Embodiment

Hereinafter, an observation apparatus according to a third embodiment of the present invention will be described. The observation apparatus described in this embodiment has a structure for canceling a chromatic aberration caused when the contact prism or the like is put to the eye to be operated. Note that the same references are provided to the same structural elements as described above.

Structure

Figure 23:
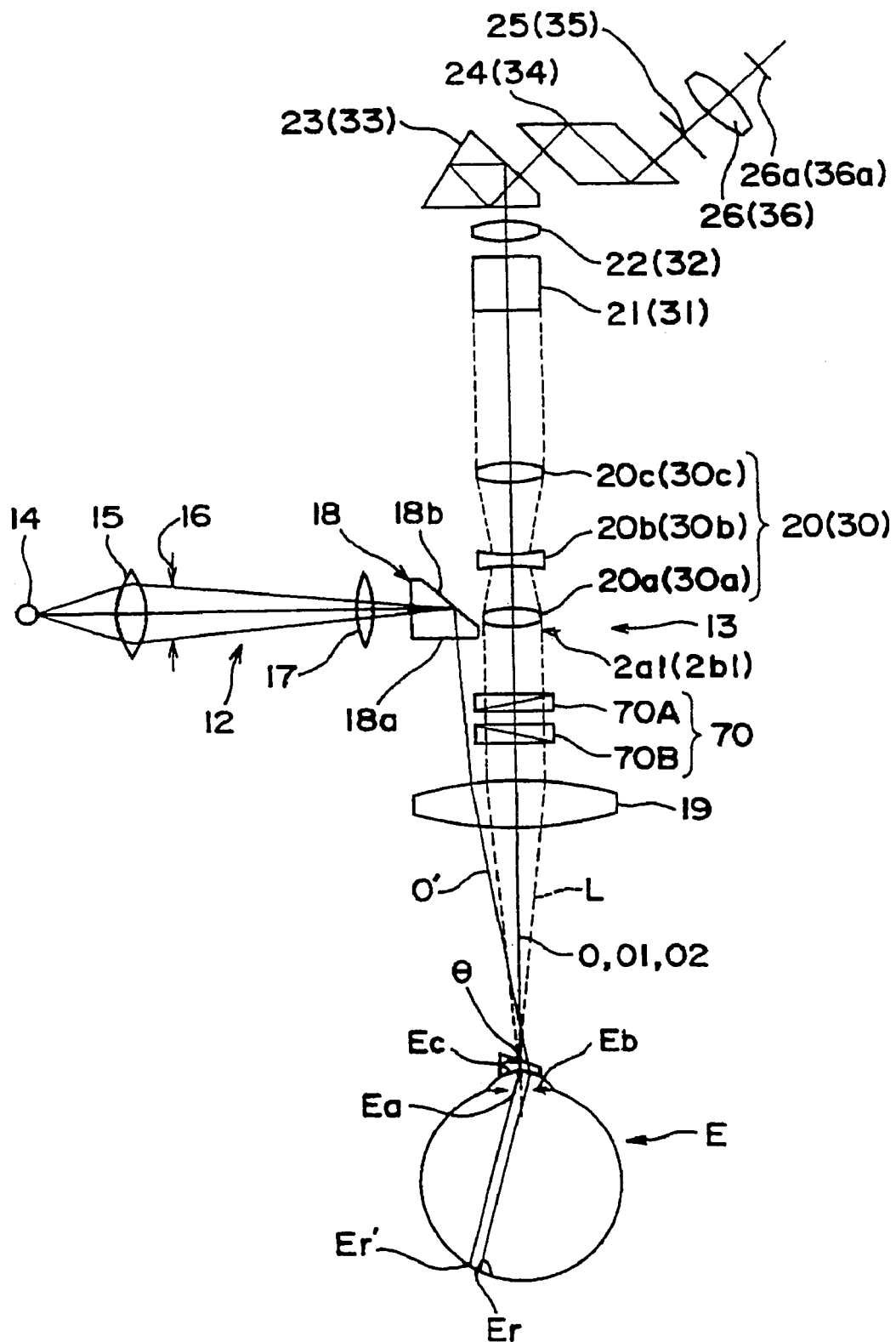
FIG. 23 is a side view showing a structure of an optical system of an observation apparatus according to a third embodiment of the present invention.
Figure 24:
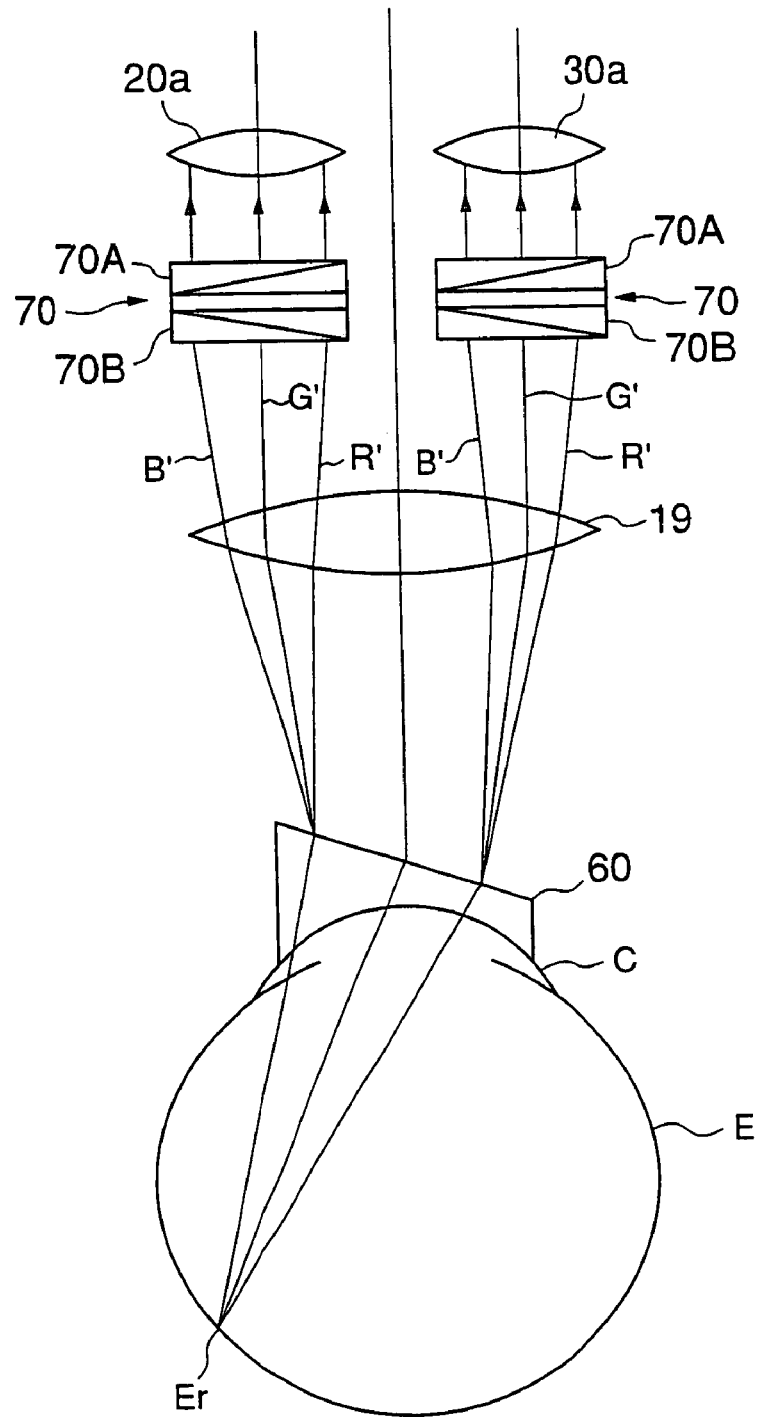
FIG. 24 is an enlarged front view showing a part of the optical system of the observation apparatus according to the third embodiment of the present invention.

FIGS. 23 and 24 show a structure of an optical system of the observation apparatus according to this embodiment, which is substantially the same structure as the observation apparatus of the modified example of the first embodiment as shown in FIG. 18. More specifically, the observation apparatus according to this embodiment includes achromatic aberration canceling optical element 70 which is provided in each of the left and right observation optical systems 13a and 13b, instead of providing the astigmatism canceling optical element 61 shown in FIG. 18.

The chromatic aberration canceling optical element 70 is disposed between the objective lens 19 and the variable lens system 20 (30) on an observation optical path for guiding a reflection light flux on the fundus Er of the eye to be operated E as a parallel light flux to the variable lens system 20 (30) (see FIG. 24). Note that the chromatic aberration canceling optical element 70 may be disposed between the variable lens system 20 (30) and the eyepiece 26 (36).

Figure 25:
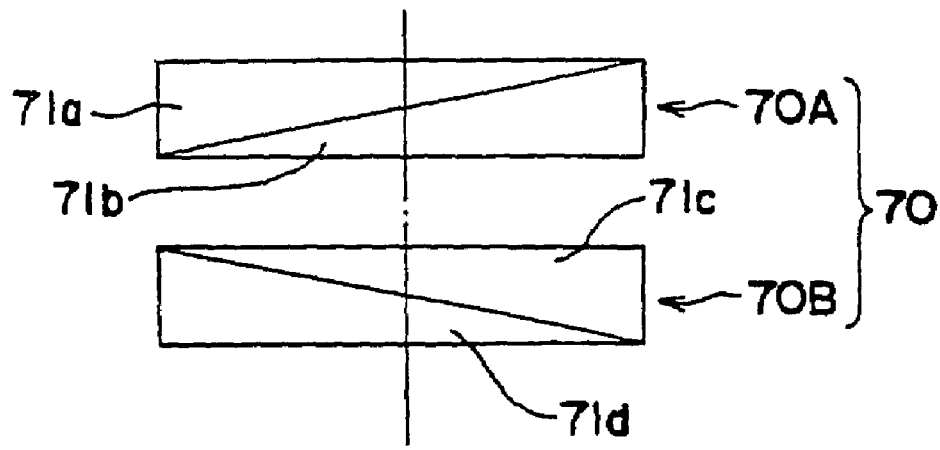
FIG. 25 is a side view showing an example of a chromatic aberration canceling optical element included in the optical system of the observation apparatus according to the third embodiment of the present invention.
Figure 26:
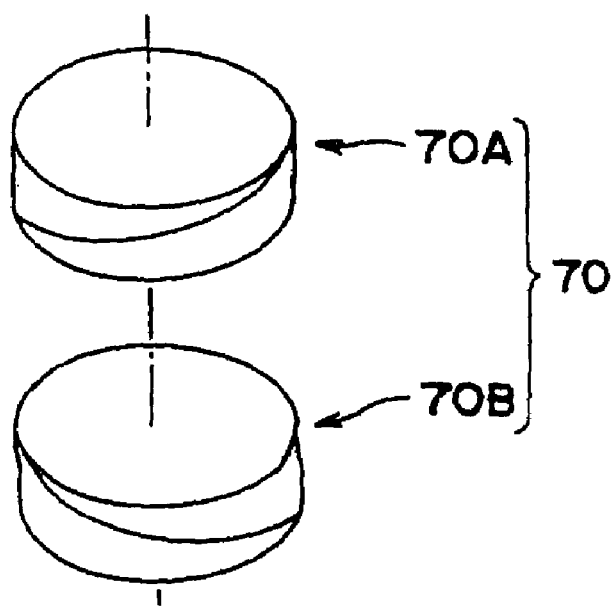
FIG. 26 is a perspective view showing the example of the chromatic aberration canceling optical element included in the optical system of the observation apparatus according to the third embodiment of the present invention.

The chromatic aberration canceling optical element 70 which is provided in each of the left and right observation optical systems 13a and 13b is composed of, for example, variable prisms 70A and 70B as shown in FIGS. 25 and 26.

The variable prism 70A is composed of prisms 71a and 71b, which are bonded to each other. The variable prism 70B is composed of prisms 71c and 71d which are bonded to each other. The prisms 71a and 71d have the same refraction index nd in the fundamental wavelength (d line). The prisms 71b and 71c have the same refraction index nd in the fundamental wavelength (d line). A dispersion ν of the prism 71a becomes smaller than a dispersion ν of the prism 71b. A dispersion ν of the prism 71d becomes smaller than a dispersion ν of the prism 71c. Here, the variable prisms 70A and 70B have the same structure. It is also possible to employ the variable prisms 70A and 70B having different structures.

The TV image pickup systems 50L and 50R for taking the fundus image using the left and right observation optical systems 13a and 13b as shown in FIG. 7 are also provided in the observation apparatus according to this embodiment.

The control panel 100 shown in FIG. 11 is provided on the observation apparatus according to this embodiment. Hereinafter, the chromatic aberration setting portion 130 will be described.

The chromatic aberration setting portion 130 includes: knobs for performing setting operation related to the chromatic aberration canceling optical element 70 of the left observation optical system 13a; and knobs for performing setting operation related to the chromatic aberration canceling optical element 70 of the right observation optical system 13b. The former knobs are an axial angle setting knob 131L for setting an axial angle of the chromatic aberration canceling optical element 70 of the left observation optical system 13a (aberration direction setting unit) and a correction amount setting knob 132L for setting the amount of astigmatism to be corrected by the chromatic aberration canceling optical element 70 of the left observation optical system 13a (correction amount setting unit). The latter knobs are an axial angle setting knob 131R for setting an axial angle of the chromatic aberration canceling optical element 70 of the right observation optical system 13b (aberration direction setting unit) and a correction amount setting knob 132R for setting the amount of astigmatism to be corrected by the chromatic aberration canceling optical element 70 of the right observation optical system 13b (correction amount setting unit).

The axial angles set by the axial angle setting knobs 131L and 131R are generally adjusted such that the axial angles are (substantially) equal to the angle related to the prism base direction, which is set by the fitting angle setting knob 112 on the prism setting portion 110. Therefore, it is possible to set the above-mentioned axial angles in conjunction with setting of the fitting angle setting knob 112. A changing switch capable of selectively switching between such automatic axial angle setting and manual axial angle setting using the axial angle setting knobs 121L and 121R may be provided.

Angles can be indicated around the axial angle setting knobs 131L and 131R while an arbitrary direction is set as 0°. In this embodiment, the right side in the lateral direction as viewed from the operator side is set as 0° and an angle increases counter-clockwise.

Numerals 0 to 10 indicated around the correction amount setting knobs 132L and 132R are marks indicating the relative amount of correction produced by the chromatic aberration canceling optical element 70. The amount of correction of zero is set as a mark of 0 and the maximum amount of correction is set as a mark of 10.

Figure 27:
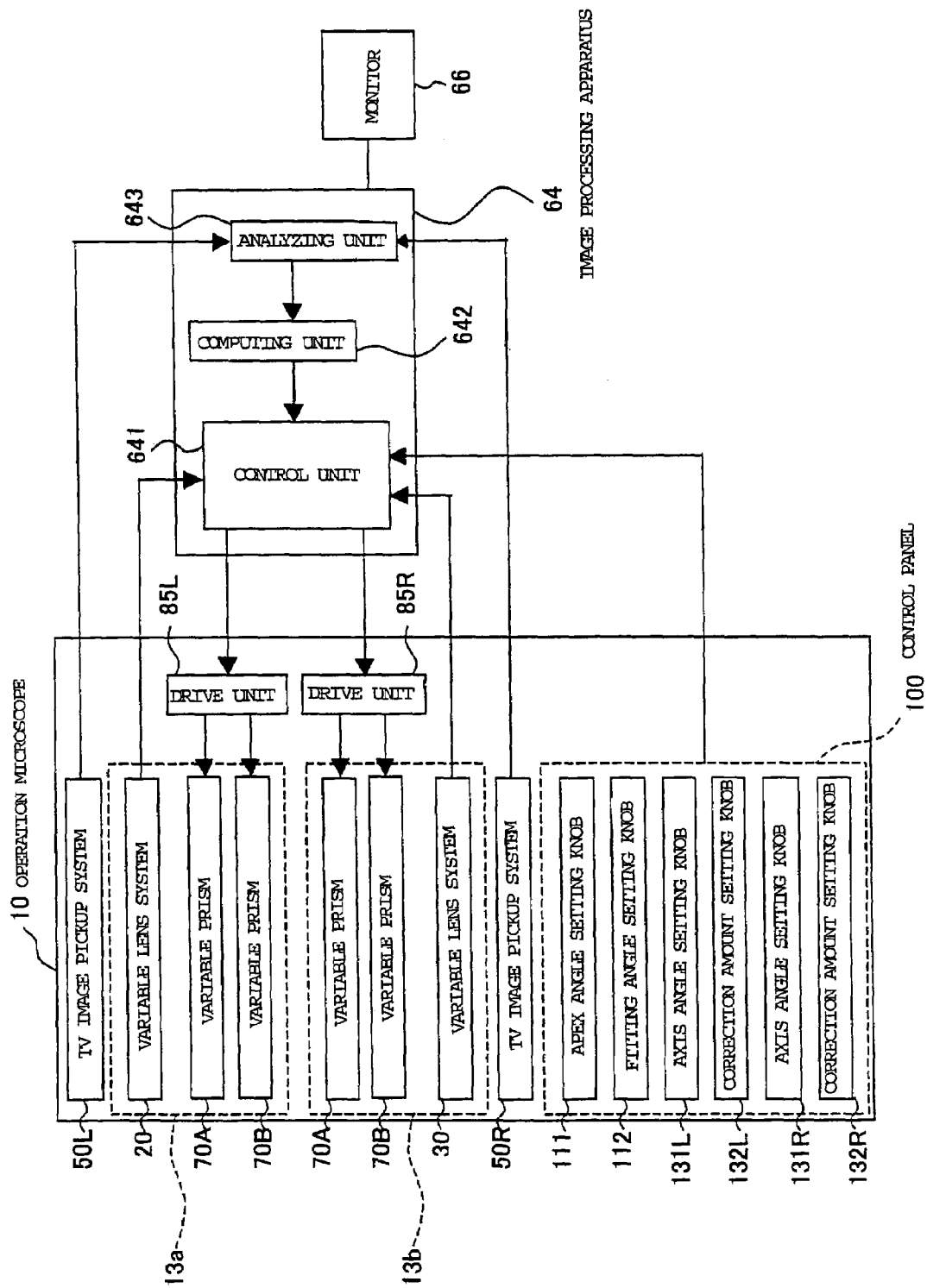
FIG. 27 is a block diagram showing a control system of the observation apparatus according to the third embodiment of the present invention.

Next, a structure of a control system of the observation apparatus according to this embodiment will be described with reference to a block diagram shown in FIG. 27. The control system of the observation apparatus according to this embodiment has substantially the same structure as in the first embodiment shown in FIG. 12. The control system of the observation apparatus according to this embodiment includes: a variable prism rotating drive unit 85L for rotating the variable prisms 70A and 70B composing the chromatic aberration canceling optical element 70 of the left observation optical system 13a about the observation optical axis O1; and a variable prism rotating drive unit 85R for rotating the variable prisms 70A and 70B composing the chromatic aberration canceling optical element 70 of the right observation optical system 13b about the observation optical axis O2.

The image processing apparatus 64 and, the control unit 641, the computing unit 642, and the analyzing unit 643 which are included in the image processing apparatus 64 perform substantially the same processings as in the first embodiment, and thus the same references are provided to those. The control unit 641 performs processings such as generation and transmission of various control signals and recognition of an observation magnification based on each of the variable lens systems 20 and 30. The analyzing unit 643 performs analyzing processing (described later) on the fundus images of the eye to be operated E which are taken by the TV image pickup systems 50L and 50R. The computing unit 642 calculates the amount of correction for canceling the chromatic aberration caused by the contact prism 60 based on an analyzed result of the analyzing unit 643.

Figure 5:
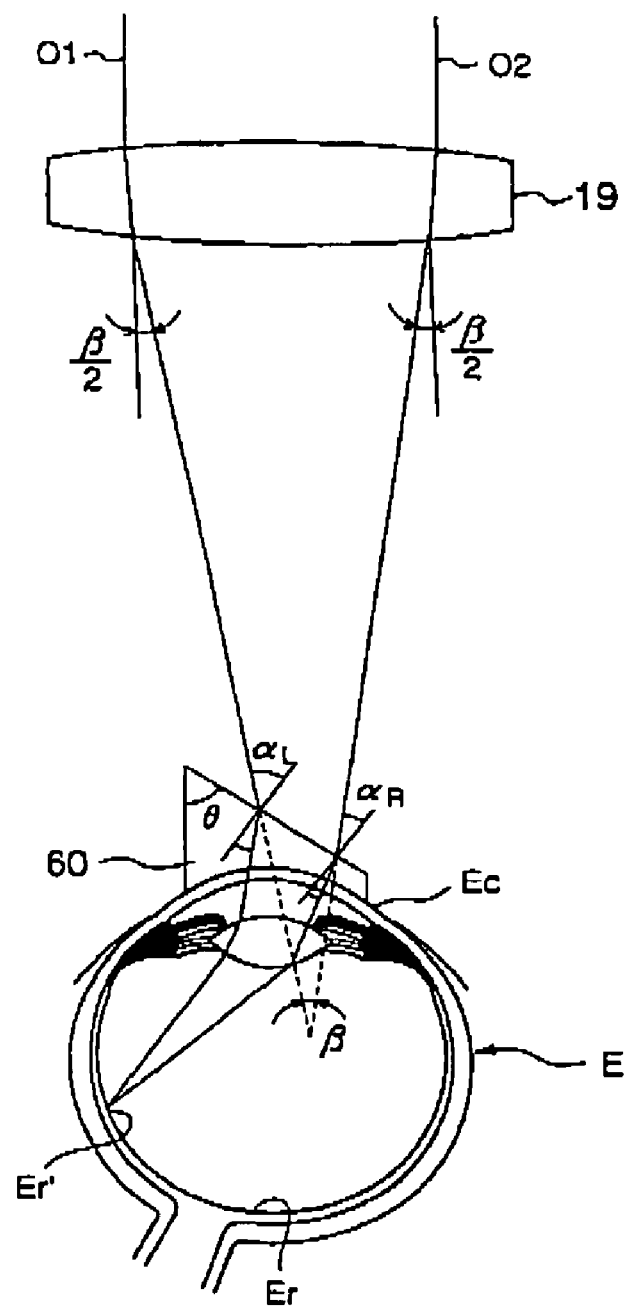
FIG. 5 is an explanatory view showing refractive states of right and left optical axes when a contact prism is put to an eye to be operated.

In general, the chromatic aberration is caused in a direction of the refracting power of a prism. FIG. 24 schematically shows a state of a chromatic aberration caused when the contact prism 60 is put to the eye to be operated E. As shown in FIG. 24, when reflection light on the fundus Er is refracted by the contact prism 60 and guided to the objective lens 19, the reflection light is divided into light beams R', G', and B' of R, G, and B wavelengths by the contact prism 60. When each of the chromatic aberration canceling optical elements 70 is rotated such that the respective light beams R', G', and B' which travel through the chromatic aberration canceling optical elements 70 become parallel light fluxes, the chromatic aberration caused by the refractive action of the contact prism 60 is removed. In the following use modes, the chromatic aberration canceling optical element 70 is adjusted by such control. As shown in FIG. 24, intervals among the light beams R', G', and B' on the left observation optical system 13a side are larger than intervals among the light beams R', G', and B' on the right observation optical system 13b side. This is because an exit angle of light traveling through the contact prism 60 with respect to the observation optical axis of the left observation optical system 13a is larger than an exit angle of light traveling through the contact prism 60 with respect to the observation optical axis of the right observation optical system 13b and thus the left observation optical system 13a is greatly affected by the chromatic aberration (see FIG. 5). Therefore, it is necessary to separately correct the chromatic aberrations caused in the left and right observation optical systems 13a and 13b.

When Z-directional blurring occurs in the observation image by a difference in length between the right and left observation optical paths, predetermined spherical power may be applied so as to cancel the blurring.

Use Mode

Use modes of the observation apparatus having the above-mentioned structure according to this embodiment will be described. According to the observation apparatus in this embodiment, various use modes can be performed as described below. Note that it is unnecessary to use a structure in which all the following use modes can be performed. A structure in which at least one of the use modes can be performed may be used. In this time, it is unnecessary to include structural parts used in the use modes which are not employed. When a structure in which a plurality of use modes can be selectively performed is used, a changing switch for switching among the respective use modes can be provided in, for example, the control panel 100.

USE EXAMPLE 1

Figure 28:
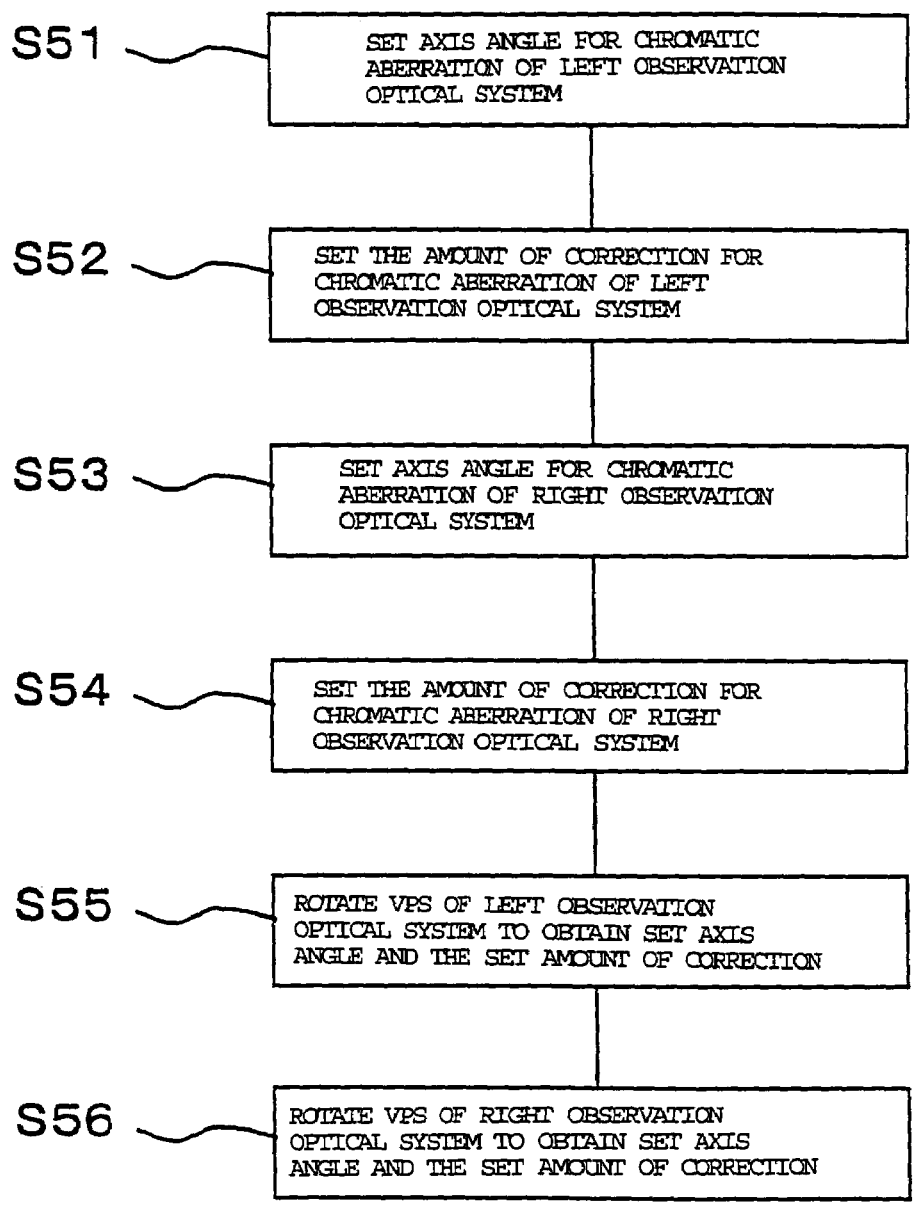
FIG. 28 is a flow chart showing an example of a use mode of the observation apparatus according to the third embodiment of the present invention.

A use mode in the case of manual operation will be described with reference to a flow chart shown in FIG. 28. First, setting is performed using the chromatic aberration setting portion 130 on the control panel 100. More specifically, the axial angle for the chromatic aberration of the left observation optical system 13a, that is, the base direction of the variable prisms 70A and 70B which is to be adjusted to correct the chromatic aberration, is set by rotating the axial angle setting knob 131L (Step S51). In addition, the amount of correction for the chromatic aberration of the left observation optical system 13a is set by rotating the correction amount setting knob 132L (Step S52). Similarly, the axial angle for the chromatic aberration of the right observation optical system 13b is set by rotating the axial angle setting knob 131R (Step S53). In addition, the amount of correction for the chromatic aberration of the right observation optical system 13b is set by rotating the correction amount setting knob 132R (Step S54). It is needless to say that either the setting operation related to the left observation optical system 13a or the setting operation related to the right observation optical system 13b may be performed first.

After the above-mentioned setting operations are performed using the control panel 100, signals related to the setting operations are sent to the control unit 641 of the image processing apparatus 64. The control unit 641 controls the variable prism rotating drive unit 85L to rotate the variable prisms 70A and 70B (abbreviated to "VPs" in FIG. 28) of the left observation optical system 13a so as to obtain the set axial angle and the set amount of correction (Step S55). Simultaneously, the control unit 641 controls the variable prism rotating drive unit 85R to rotate the variable prisms 70A and 70B of the right observation optical system 13b so as to obtain the set axial angle and the set amount of correction (Step S56).

Thus, the chromatic aberration caused by the contact prism 60 which is put to the eye to be operated E is corrected, so that the observation image can be preferably viewed. In particular, the amount of correction and the like can be set for each of the right and the left independently. Therefore, even in the case where the amount of aberrations in the right and the left are different from each other, as in the case where the fundus surroundings Er' is observed, the image can be normally stereoscopically viewed. When the astigmatism is not sufficiently removed by one-time correction, the operator can operate the control panel 100 to perform further correction.

USE EXAMPLE 2

Figure 29:
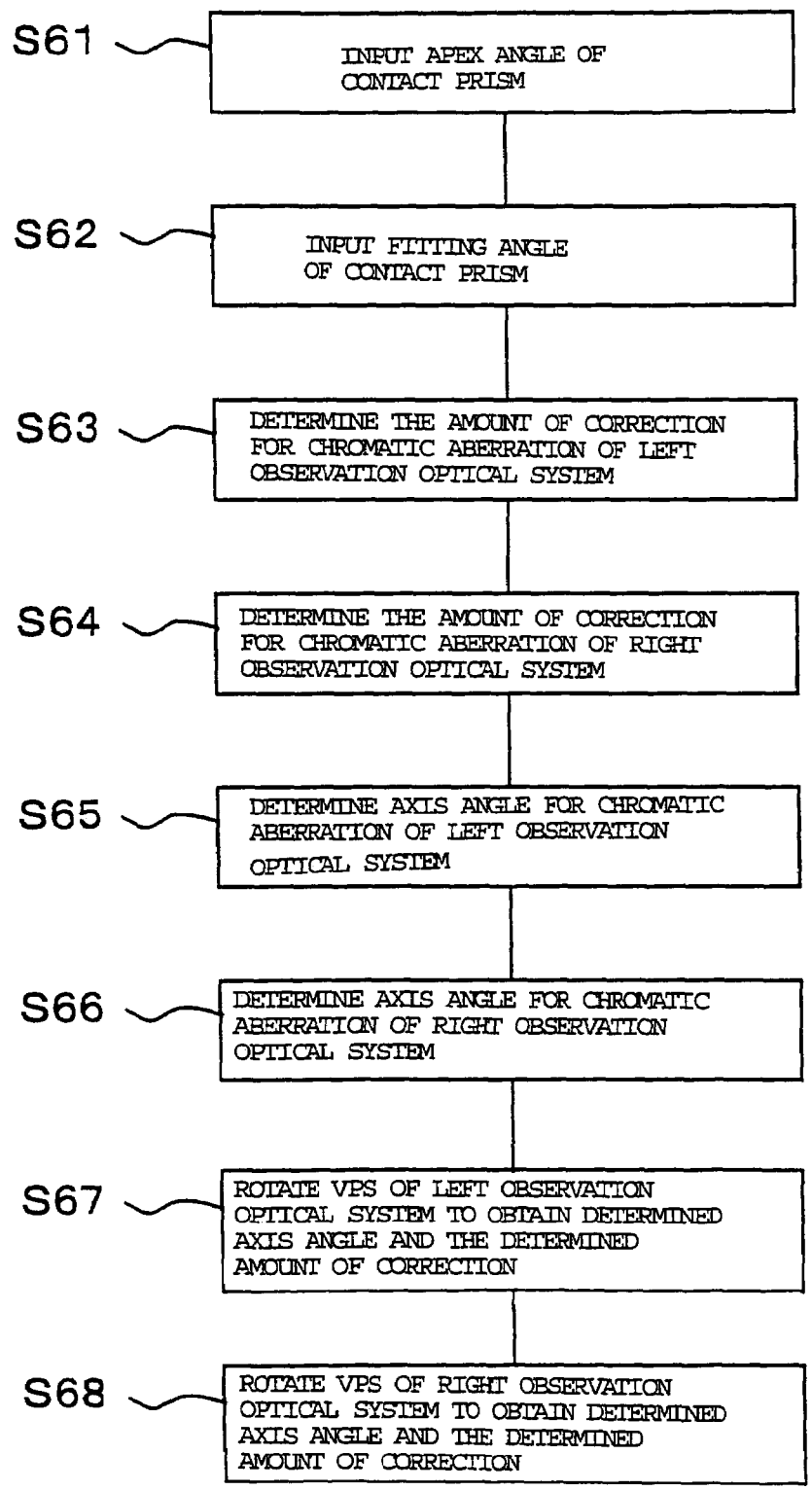
FIG. 29 is a flow chart showing an example of a use mode of the observation apparatus according to the third embodiment of the present invention.

Next, another use mode of the observation apparatus according to this embodiment will be described with reference to a flow chart shown in FIG. 29. In this use mode, only conditions of the contact prism 60 which is put to the eye to be operated E are inputted instead of setting the axial angle for the chromatic aberration and the amount of correction thereof, so that the operation becomes easier.

First, the apex angle θ of the contact prism 60 which is put to the eye to be operated E is inputted by rotating the apex angle setting knob 111 of the prism setting portion 110 on the control panel 100 (Step S61). The fitting angle of the contact prism 60 is inputted by rotating the fitting angle setting knob 112 (Step S62). The input contents are transmitted as signals to the control unit 641 of the image processing apparatus 64.

Determination data for determining the amount of correction produced by the chromatic aberration canceling optical element 70 based on the apex angle θ of the contact prism 60 are stored in advance in the memory device of the image processing apparatus 64. For example, data which are obtained by performing a test using the model eye on each of the prepared contact prisms 60 as described in the first embodiment may be used as the determination data.

The control unit 641 recognizes the observation magnification based on each of the variable lens systems 20 and 30. Then, the control unit 641 determines the amount of correction for the chromatic aberration of the left observation optical system 13a (Step S63) and the amount of correction for the chromatic aberration of the right observation optical system 13b (Step S64) with reference to the above-mentioned determination data based on the recognized observation magnification and the apex angle θ inputted in Step S61. Further, the control unit 641 determines the axial angle for the chromatic aberration of the left observation optical system 13a and the axial angle for the chromatic aberration of the right observation optical system 13b based on the fitting angle of the contact prism 60 which is inputted in Step S62 (Steps S65 and S66). It may be determined that, for example, the fitting angle is equal to the axial angles.

After the determination of the amount of correction and the axial angle, the control unit 641 controls the variable prism rotating drive unit 85L to rotate the variable prisms 70A and 70B of the left observation optical system 13a so as to obtain the determined axial angle and the determined amount of correction (Step S67). In addition, the control unit 641 controls the variable prism rotating drive unit 85R to rotate the variable prisms 70A and 70B of the right observation optical system 13b so as to obtain the determined axial angle and the determined amount of correction (Step S68).

USE EXAMPLE 3

Next, another use mode of the observation apparatus according to this embodiment will be described. In this use mode, the chromatic aberration correction is automatically performed based on the observation images related to the right and the left, which are received by the CCD image pickup elements 54L and 54R of the TV image pickup systems 50L and 50R.

Figure 35:
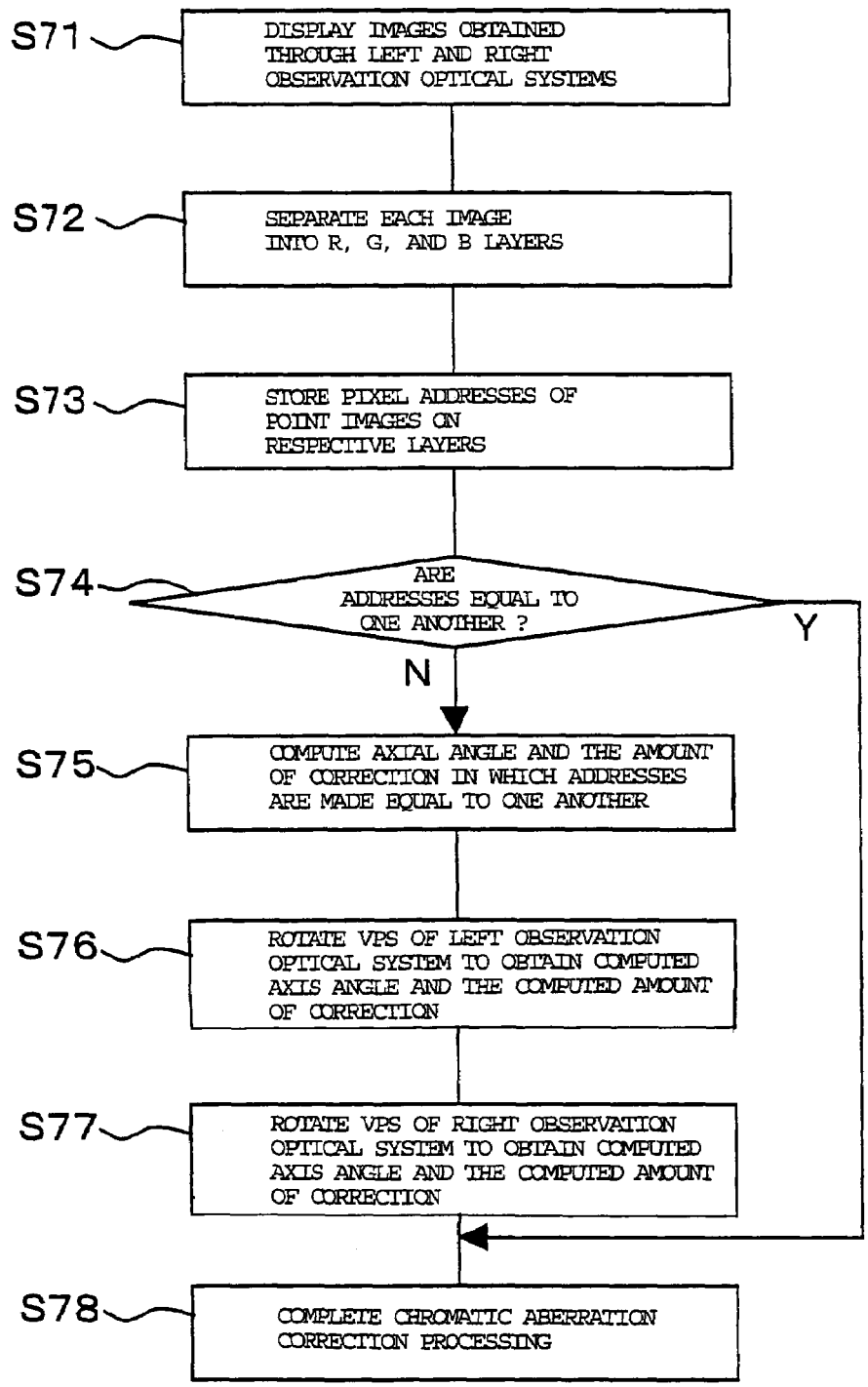
FIG. 35 is a flow chart showing an example of a use mode of the observation apparatus according to the third embodiment of the present invention.

The respective observation images observed through the left observation optical system 13a and the right observation optical system 13b are displayed on the screen 66A of the monitor 66. FIGS. 30 to 34 show examples of a display screen displayed on the monitor 66 (in which only the observation image observed through the left observation optical system 13a is shown for the sake of simplification). FIG. 35 is a flow chart showing chromatic aberration correction processing according to this embodiment.

Figure 30:
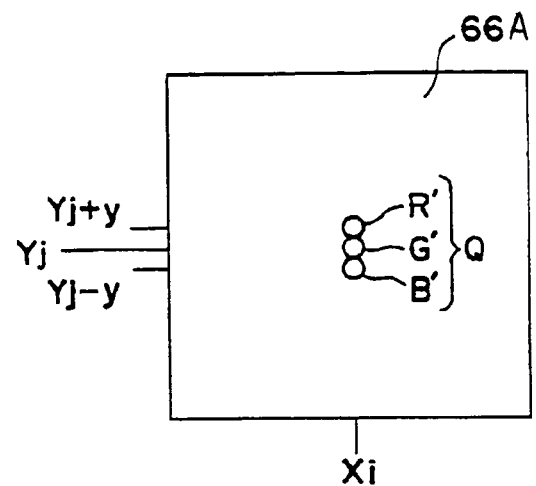
FIG. 30 is an explanatory view schematically showing a phenomenon in which a point image is displayed on a screen with a state in which the point image is separated into three point images of R, G, and B when chromatic aberration occurs.

First, the fundus images Er" obtained through the left and right observation optical systems 13a and 13b are displayed on the monitor 66 (Step S71). When the chromatic aberration is caused by the contact prism 60, as schematically shown in FIG. 30, a white point image Q is separated into three colors of R, G, and B, so that point images R', G', and B' are displayed. When the chromatic aberration is not caused, the white point image Q is displayed without being separated.

Figure 31:
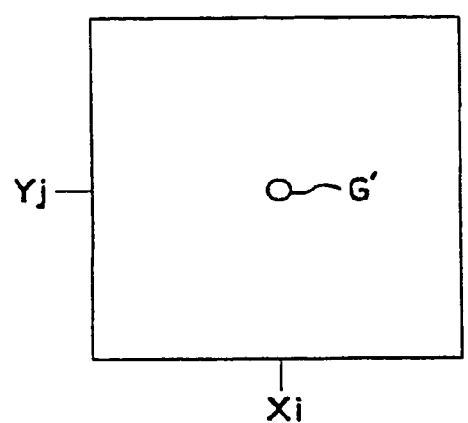
FIG. 31 is an explanatory view schematically showing a state in which only a G-layer is extracted from the image and stored.
Figure 32:
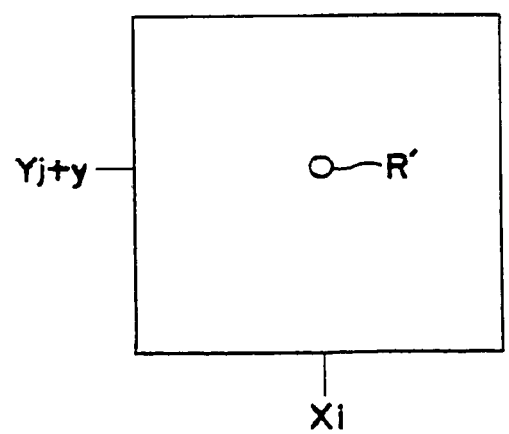
FIG. 32 is an explanatory view schematically showing a state in which only an R-layer is extracted from the image and stored.
Figure 33:
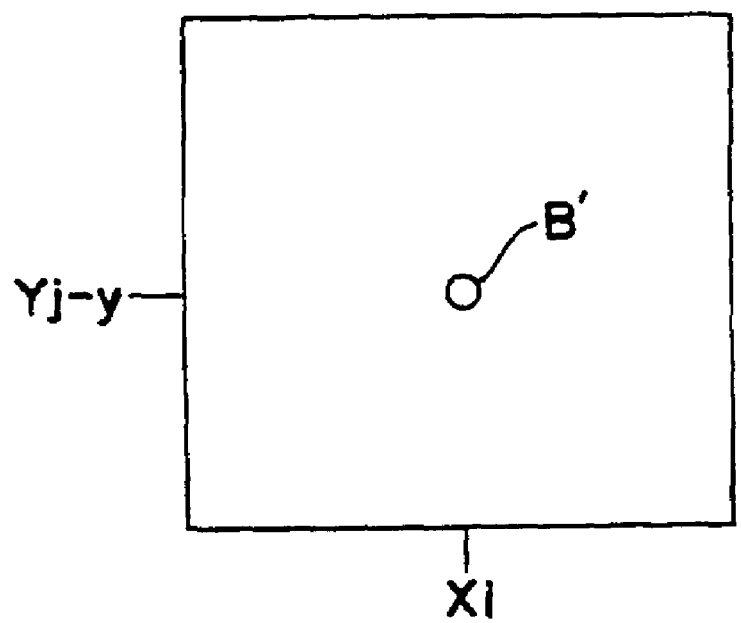
FIG. 33 is an explanatory view schematically showing a state in which only a B-layer is extracted from the image and stored.
Figure 34:
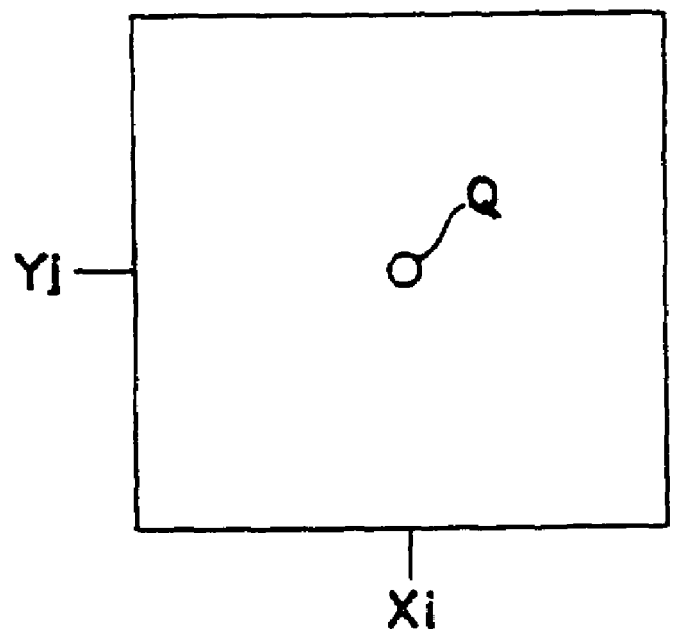
FIG. 34 is an explanatory view schematically showing a state in which superimposition of the respective layers of the image is displayed.

Next, each of the fundus images related to the right and the left is separated into R, G, and B layers by the analyzing unit 643 (Step S72) and pixel addresses of the point images R', G', and B' on the respective layers are stored in the memory device (see the first embodiment) (Step S73). For example, as shown in FIGS. 31 to 33, when an address on the G layer serving as a reference is given by (Xi, Yj), an address on the R layer becomes (Xi, Yj+y) and an address on the B layer becomes (Xi, Yj−y). Those addresses a restored in the memory device. Here, "y(=0, 1, 2, . . . )" indicates a displacement of the address of each of the point image R' on the R layer and the point image B' on the B layer from the address of the point image G' on the G layer, which is caused by chromatic aberration.

Next, the computing unit 642 compares among the pixel addresses on the respective layers to determine whether or not the pixel addresses are equal to one another (Step S74). When the addresses on the three layers are equal to one another without causing the separation of the point image Q by chromatic aberration (when y=0), the chromatic aberration correction processing is completed (Step S78).

When the addresses are not equal to one another, the control unit 641 computes the axial angle (base direction) and the amount of correction of the variable prisms 70A and 70B in which the addresses on the respective layers are made equal to one another (Step S75). In the above-mentioned example, the control unit 641 computes the axial angle and the amount of correction which are used to shift the point image R' on the R layer in the Y-direction by −y address and shift the point image B' on the B layer in the Y-direction by +y address. It is needless to say that such computing processing may be performed using as a reference the point image R' on the R layer or the point image B' on the B layer. For example, the computation of the control unit 641 can be executed with reference to the axial angle and the amount of correction which are required to shift the point image in each of the X-direction and the Y-direction by one address and stored in advance in the above-mentioned memory device or the like.

Further, the control unit 641 transmits control signals for rotating the variable prisms 70A and 70B of each of the left and right observation optical systems 13a and 13b to the variable prism rotating drive units 85L and 85R based on the computed result to rotate variable prisms 70A and 70B (Steps S76 and S77). Then, the chromatic aberration correction processing of this use mode is completed (Step S78). Note that the control unit 641, the computing unit 642, and the analyzing unit 643 according to this embodiment compose a chromatic aberration correcting unit in the present invention.

Here, when the chromatic aberration is not completely canceled, the chromatic aberration may be corrected by rotating the variable prisms 70A and 70B on the left and right using the control panel 100.

According to this use mode in which the above-mentioned processings are executed, the chromatic aberration is automatically corrected without performing setting operation and input operation, so that the operability can be improved. In particular, the automatic correction is performed without depending on the apex angle θ and the fitting angle of the contact prism 60, the observation magnification, and the like, so that the convenience becomes higher. The fundus images observed through the left and right observation optical systems 13a and 13b can be separately corrected for the left and the right, adequate stereoscopic viewing is possible.

MODIFIED EXAMPLE

Figure 36:
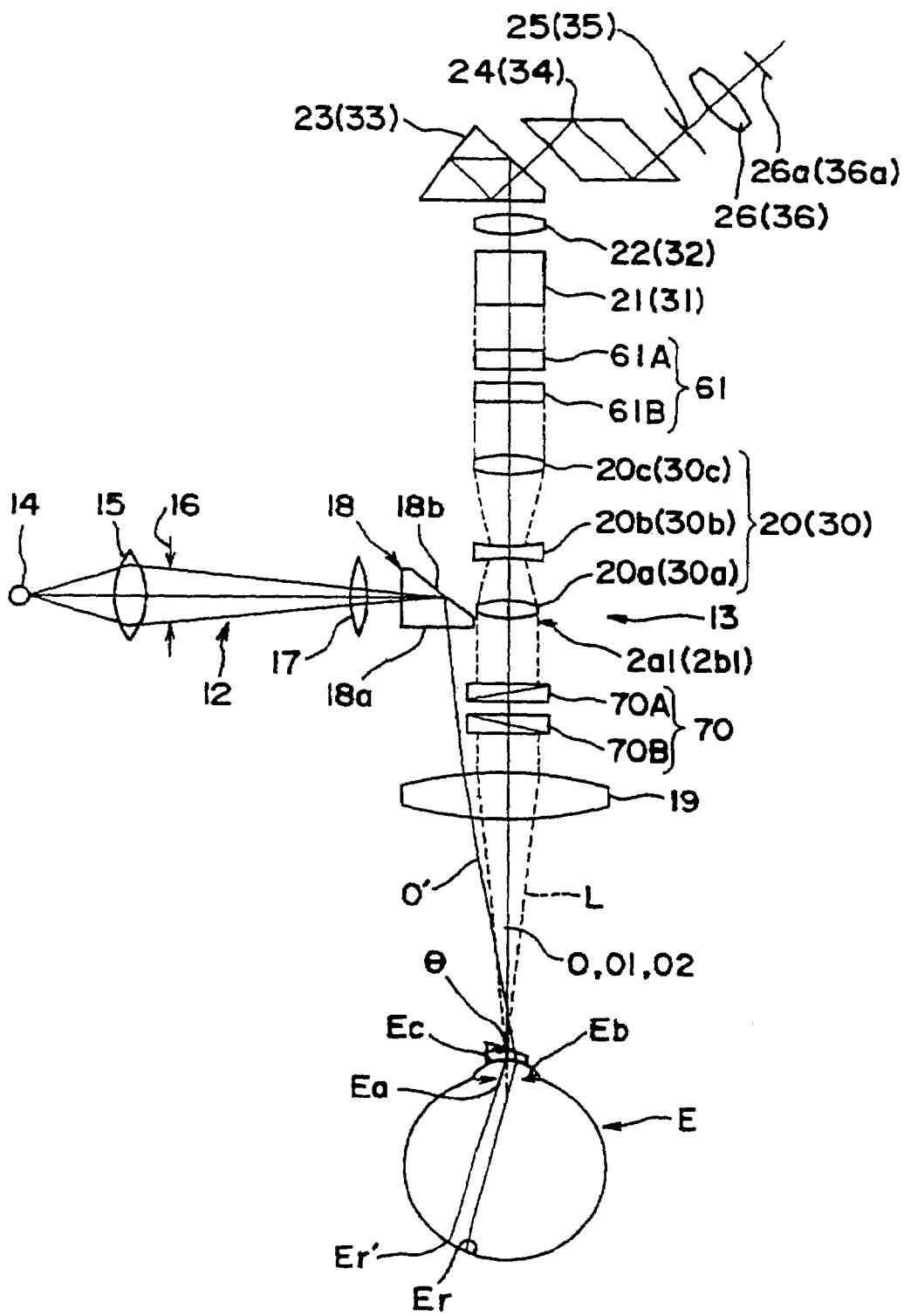
FIG. 36 is a side view showing a structure of an optical system of the observation apparatus as a modified example of the third embodiment of the present invention.

FIG. 36 shows a structure of an optical system of an observation apparatus as a modified example of this embodiment. In the observation apparatus, the astigmatism canceling optical element 61 described in the first embodiment is disposed between the variable lens system 20 (30) and the eyepiece 26 (36). In addition, the chromatic aberration canceling optical element 70 is disposed between the objective lens 19 and the variable lens system 20 (30). Further, although not shown, the variable cross cylinder lens rotating drive units 65L and 65R and the variable prism rotating drive units 85L and 85R are provided so as to be separately controlled for the right and the left. According to the observation apparatus, it is possible to cancel both the astigmatism and the chromatic aberration which are caused when the contact prism 60 is put to the eye to be operated E.

Fourth Embodiment

Figure 37:
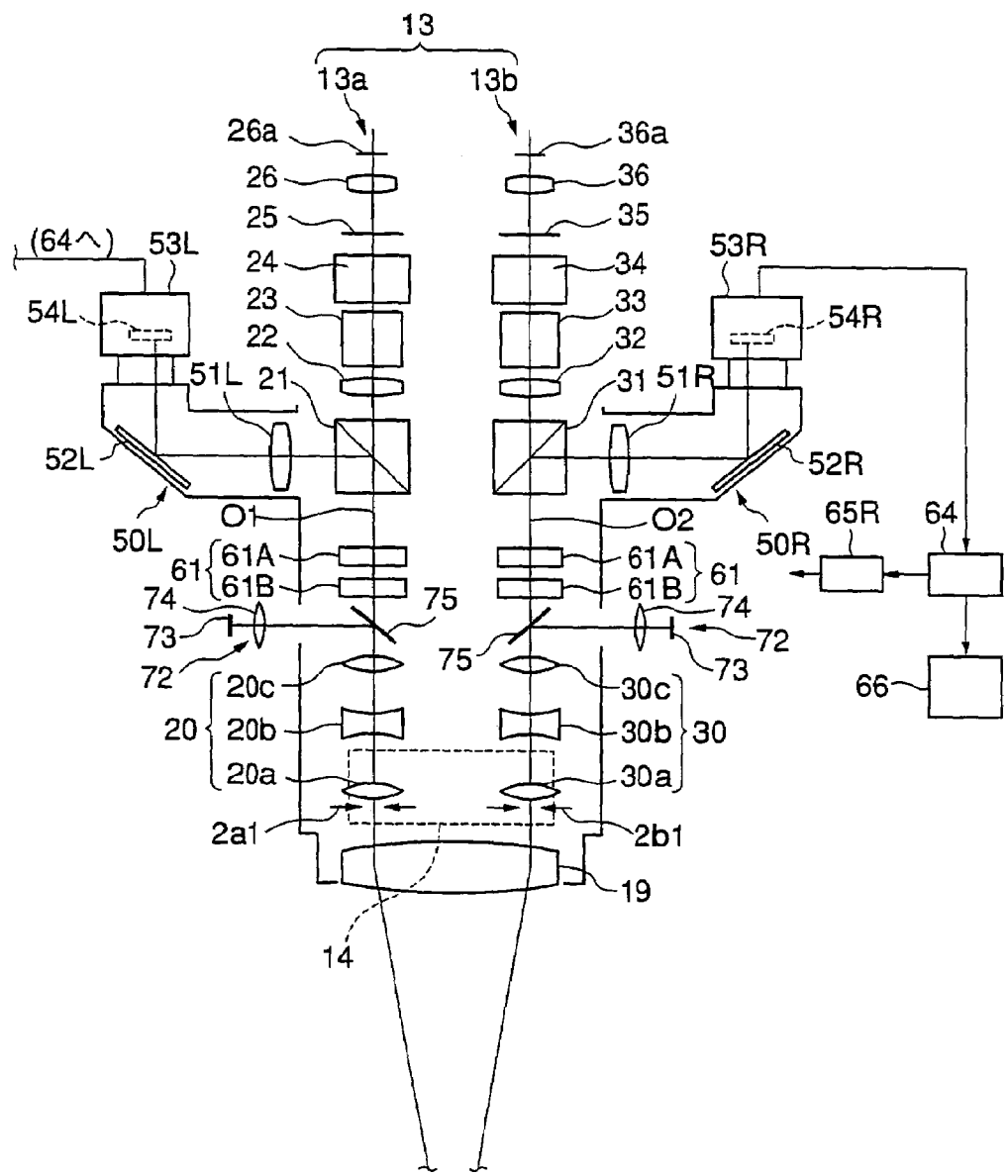
FIG. 37 is a front view showing a part of an optical system of an observation apparatus according to a fourth embodiment of the present invention.

Hereinafter, an observation apparatus according to a fourth embodiment of the present invention will be described. FIG. 37 shows schematic structures of an optical system and control system in the observation apparatus according to this embodiment. The observation apparatus includes the same control system as shown in FIG. 12. The description will be made with reference to FIG. 37 as appropriate. Note that the same references are provided to the same structural elements as described above.

Structure

In the observation apparatus according to this embodiment, a projection optical system 72 for projecting a pattern image to the fundus Er of the eye to be operated E, which is not shown here, is provided between the variable lens system 20 (30) and the astigmatism canceling optical element 61 in each of the left and right observation optical systems 13a and 13b. The projection optical system 72 includes a ring-shaped pattern plate 73 for forming a ring-shaped pattern (ring pattern), a projection lens 74, and a half mirror 75 for merging the optical axis of the projection optical system 72 with the observation axis O1 or O2.

Although not shown in FIG. 37, an image taken by the TV image pickup system 50L on the left observation optical system 13a side is also transmitted to the image processing apparatus 64. The astigmatism canceling optical element 61 of the left observation optical system 13a is driven by the variable cross cylinder lens rotating drive unit 65L.

The ring pattern formed by the ring-shaped pattern plate 73 on the left observation optical system 13a side travels through the projection lens 74 and the half mirror 75 and is guided to the contact prism 60 which is not shown through the variable lens system 20 and the objective lens 19. Then, the ring pattern is refracted by the contact prism 60 and projected to the fundus surroundings Er'. Similarly, the ring pattern formed by the ring-shaped pattern plate 73 on the right observation optical system 13b side travels through the projection lens 74 and the half mirror 75 and is guided to the contact prism 60 which is not shown through the variable lens system 30 and the objective lens 19. Then, the ring pattern is refracted by the contact prism 60 and projected to the fundus surroundings Er'.

Figure 38:
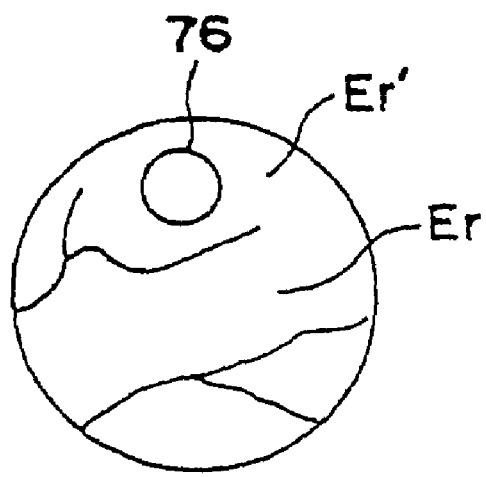
FIG. 38 is an explanatory view showing a ring pattern projected to fundus surroundings by a projection optical system included in the optical system of the observation apparatus according to the fourth embodiment of the present invention.
Figure 39:
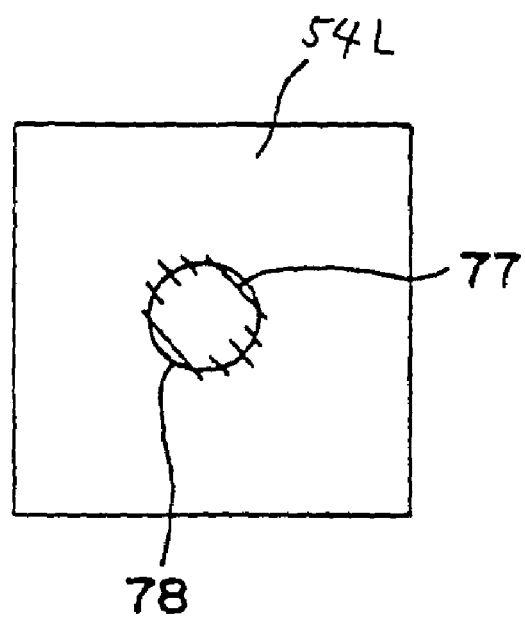
FIG. 39 is an explanatory view showing a state in which a flow of image resulting from astigmatism occurs on a ring pattern image obtained by an image receiving element through a contact prism.

At this time, a ring pattern image 76 as shown in FIG. 38 is formed on the fundus surroundings Er'. Note that only the ring pattern image projected through the left observation optical system 13a is shown in FIG. 38. When the CCD image pickup element 54L receives the ring pattern image 76 with a state in which the power of the astigmatism canceling optical element 61 is set to 0 diopter, a ring pattern image 78 having a flow 77 resulting from the astigmatism caused by the contact prism 60 is obtained as shown in FIG. 39.

Use Mode

Figure 40:
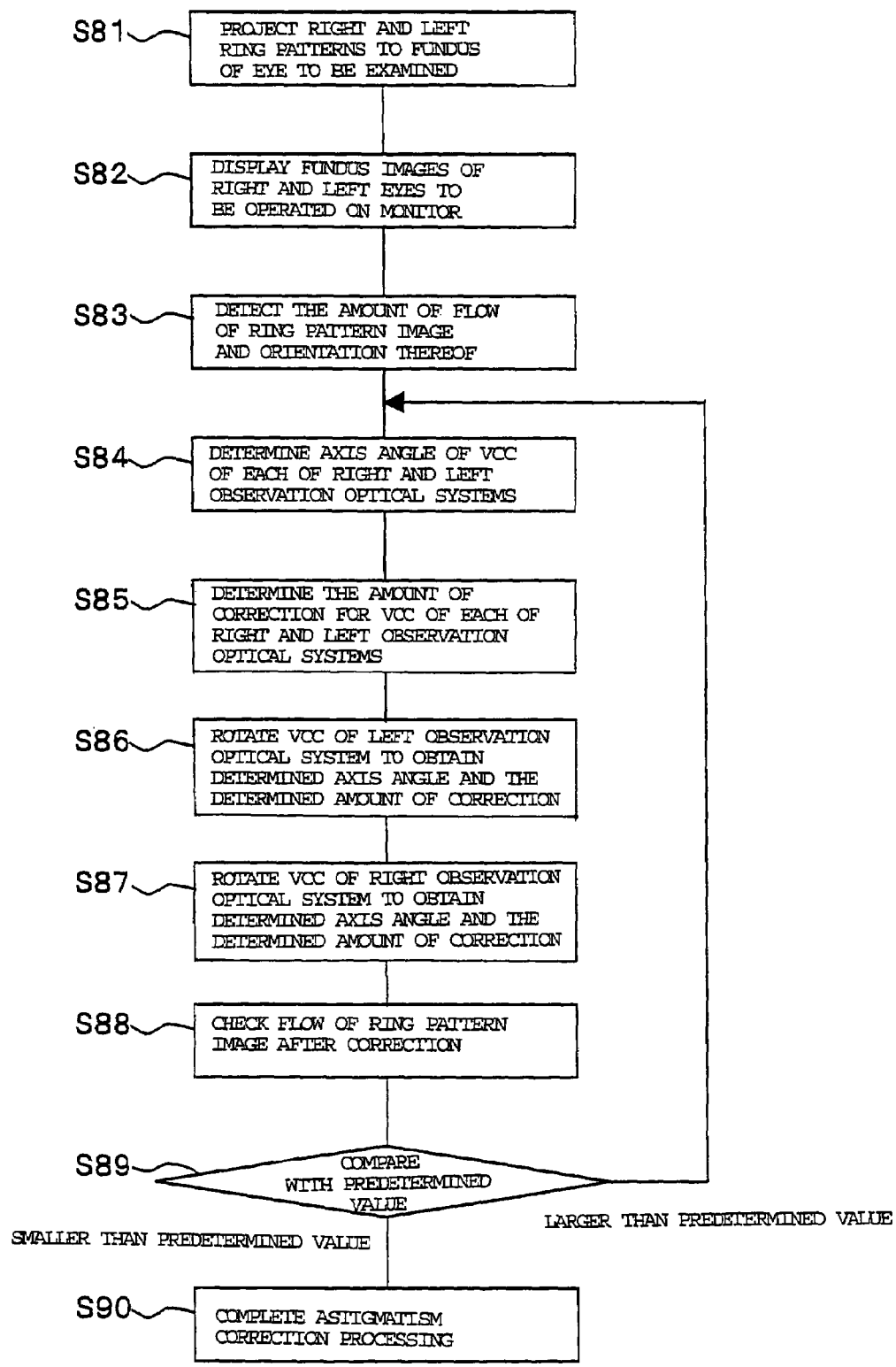
FIG. 40 is a flow chart showing an example of a use mode of the observation apparatus according to the fourth embodiment of the present invention.

Hereinafter, an example of a use mode of the observation apparatus having the above-mentioned structure according to this embodiment will be described with reference to a flow chart shown in FIG. 40. First, the ring patterns are projected to the fundus Er (fundus surroundings Er') of the eye to be examined E by the right and left projection optical systems 72 (Step S81). The fundus images Er" obtained through the left and right observation optical systems 13a and 13b are displayed on the display monitor 66 (Step S82).

Next, the analyzing unit 643 extracts the flow 77 of the taken ring pattern image 78 from each of the fundus images and analyzes the flow 77 to detect a direction of the flow and the amount of flow (Step S83).

Then, the computing unit 642 determines the axial angle and the power (the amount of correction) of the cylinder lenses 61A and 61B for each of the left observation optical systems 13a and the right observation optical systems 13b based on the detected direction of the flow 77 of the ring pattern image 78 and the detected amount of the flow thereof (Steps S84 and S85). Here, the analyzing unit 643 and the computing unit 642 according to this embodiment compose a second correction amount computing unit in the present invention.

The control unit 641 generates control signals for rotating the cylinder lenses 61A and 61B with respect to the determined axial angle and the determined amount of correction and transmits the control signals to the variable cross cylinder lens rotating drive units 65L and 65R. The variable cross cylinder lens rotating drive units 65L and 65R rotate the cylinder lenses 61A and 61B of each of the left and right observation optical systems 13a and 13b based on the received control signals (Steps S86 and S87). According to such processings, the flow 77 of the ring pattern image 78 on each of the fundus images is corrected.

Next, the remaining amount of flow 77 of the ring pattern image 78 on each of the fundus images after the correction is checked (Step S88). In other words, the analyzing unit 643 again analyzes the remaining amount of flow 77 (and the direction thereof). The computing unit 642 calculates the amount of flow 77 (and the direction thereof). The control unit 641 compares the calculated amount of flow 77 with a predetermined value which is preset (Step S89). Note that the predetermined value is set as a threshold value for making the fundus image sufficiently clear.

When the remaining amount of flow 77 is larger than the predetermined value, the same correction is performed.

Then, the remaining amount of flow 77 is checked again and the comparison with the predetermined value is performed. Such processings are repeated until the remaining amount of flow 77 becomes smaller than the predetermined value. When the amount of flow 77 becomes smaller than the predetermined value, the astigmatism correction processing is completed (Step S90).

Although not shown in the drawing, a correction lens (group) for correcting a positive or negative spherical power error caused by the cylinder lenses 61A and 61B may be provided in each of the left and right observation optical systems 13a and 13b to generate the power for reducing the remaining amount of flow 77.

The positive or negative spherical power error caused by the cylinder lenses 61A and 61B may be corrected by using the control panel 100 described in the first embodiment.

According to the observation apparatus in this embodiment in which the above-mentioned processings are executed, the astigmatism is automatically corrected without performing setting operation and input operation, so that the operability can be improved. The amount of correction is computed using the known ring pattern, so that the amount of correction can be accurately obtained. In addition, the amount of correction can be separately obtained for each of the left and the right based on the ring pattern images projected through the left and right observation optical systems 13a and 13b, adequate stereoscopic viewing is possible.

Note that in order to separately use the ring pattern images projected through the left and right observation optical systems 13a and 13b, ring patterns having different colors may be projected.

Fifth Embodiment

An observation apparatus according to a fifth embodiment of the present invention will be described with reference to the drawings.

Structure

The observation apparatus according to this embodiment has a structure which can be applied to the case where the TV image pickup system cannot be provided in each of the left and right observation optical systems, which is different from the structures of the observation apparatuses according to the first to fourth embodiments.

Figure 3:
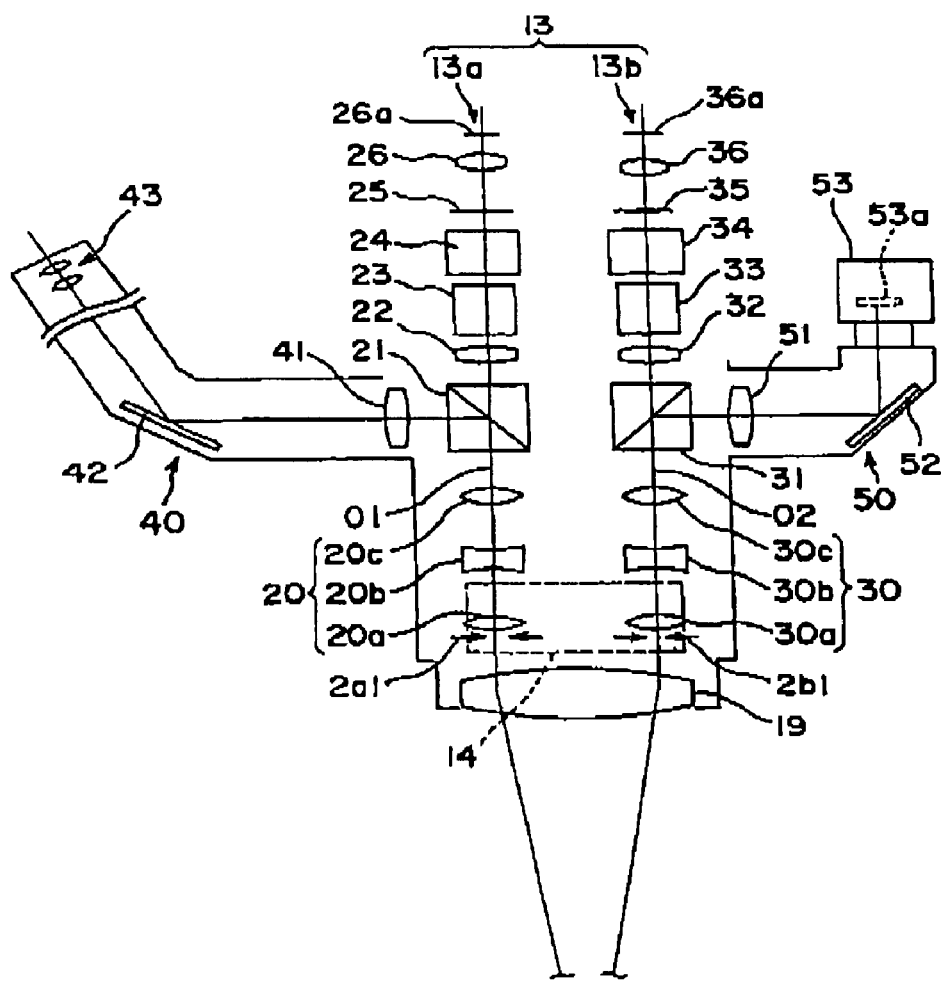
FIG. 3 is a front view showing the schematic structure of the conventional optical system of the operation microscope apparatus.
Figure 4:
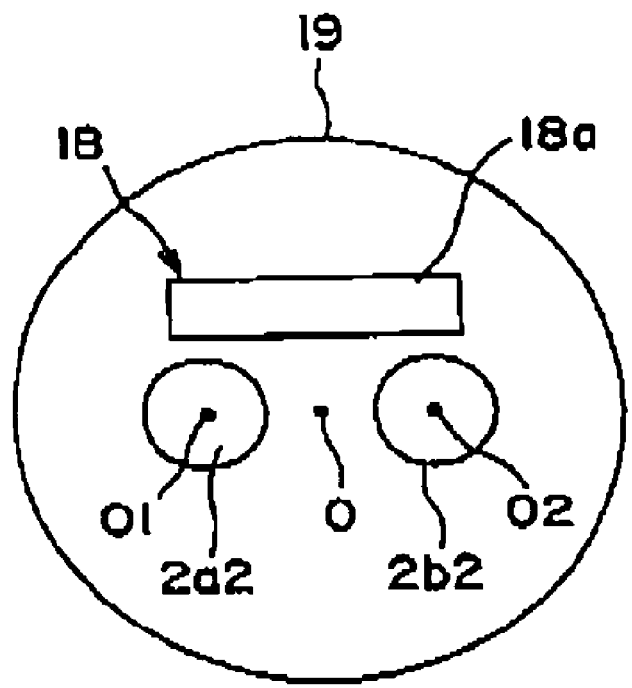
FIG. 4 is a plan view for explaining a positional relationship between an objective lens and observation optical paths.

The observation apparatus according to this embodiment includes the same optical systems as a conventional observation apparatus (see FIG. 3). That is, as in the conventional observation apparatus, a single TV image pickup system 50 and an auxiliary observation optical system 40 for assistance are provided. A structure according to this embodiment as described below can be obtained by adding the astigmatism canceling optical element (variable cross cylinder lens) 61 and/or the chromatic aberration canceling optical element (variable prism) 70 to each of the right and left observation optical systems of the conventional observation apparatus. Here, a control manner in the case of controlling the astigmatism canceling optical element is similar to a control manner in the case of controlling the chromatic aberration canceling optical element. Therefore, the case where the astigmatism canceling optical element is used will be described. Note that, when the astigmatism correction processing is performed, the computing unit 642 acts as a fourth correction amount computing unit in the present invention.

Figure 41:
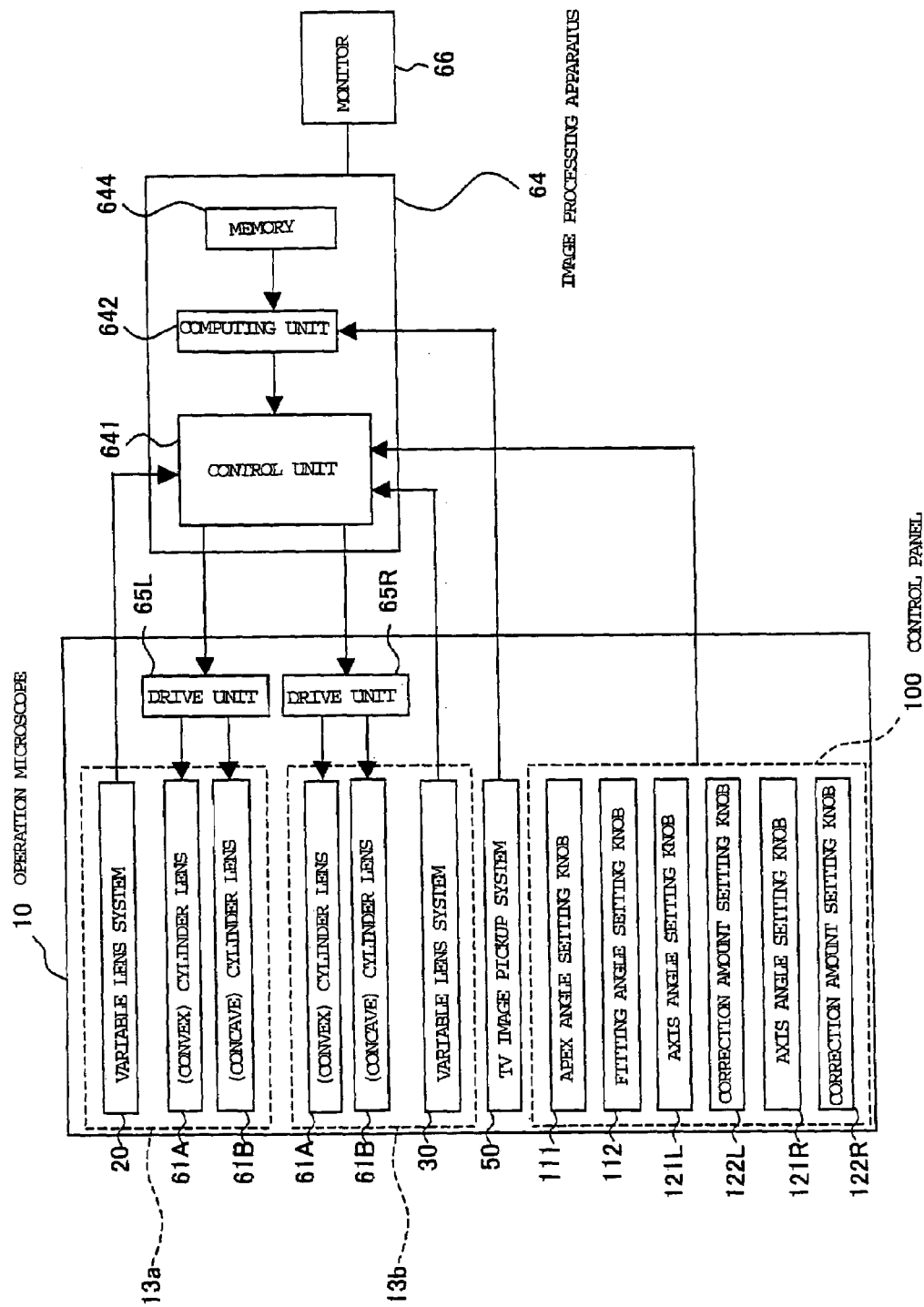
FIG. 41 is a block diagram showing a control system of an observation apparatus according to a fifth embodiment of the present invention.

FIG. 41 shows a structure of a control system of an observation apparatus according to this embodiment. The image processing apparatus 64 shown in FIG. 41 includes the control unit 641, the computing unit 642 serving as a third correction amount computing unit in the present invention, and the memory 644 serving as the memory device. The computing unit 642 computes the amount of drive (the amount of correction for astigmatism) of the cylinder lenses 61A and 61B of each of the left and right observation optical systems 13a and 13b based on data stored in the memory 644.

An observation image of the eye to be operated E, which is taken by the TV image pickup system 50 is stored in the memory 644. Determination data for determining the amount of correction for the astigmatism of each of the left and right observation optical systems 13a and 13b according to the apex angle θ of the contact lens 60 and the fitting angle thereof to the eye to be operated E are stored in advance in the memory 644. The determination data related to the right observation optical system 13b used for taking the image by the TV image pickup system 50 are data for determining the amount of correction for the astigmatism based on the observation image of the eye to be operated E, which are described in the first and second embodiments. The determination data related to the left observation optical system 13a in which the amount of correction for the astigmatism cannot be directly obtained from the observation image are data for determining the amount of correction for the astigmatism based on the amount of correction for the astigmatism of the right observation optical system 13b which is determined by analyzing the observation image and the apex angle of the contact prism 60 and the fitting angle thereof which are inputted from the control panel 100.

Use Mode

Hereinafter, a use mode of the observation apparatus having the above-mentioned structure according to this embodiment will be described with reference to a flow chart shown in FIG. 42. First, the apex angle and the fitting angle of the contact prism 60 which is put to the eye to be operated E are inputted by operating the control panel 100 (Steps S91 and S92). Next, the observation image is taken by the TV image pickup system 50 through the right observation optical system 13b and displayed as the fundus image of the eye to be operated E on the monitor 66 (Step S93).

Then, the computing unit 642 analyzes the fundus image displayed on the monitor 66 using data stored in advance in the memory 644 and computes the amount of correction for the astigmatism of the right observation optical system 13b (Step S94). In this time, the axial angle of the cylinder lenses 61A and 61B of the right observation optical system 13b is set based on the fitting angle of the contact prism 60 which is inputted in Step S92. Note that a method of analyzing the fundus image based on a detected flow of image as described above, a method of analyzing the fundus image using a projected ring pattern, or the like can be used as appropriate as a method of analyzing the fundus image.

Then, the computing unit 642 computes the amount of correction for the astigmatism of the left observation optical system 13a from the amount of correction for the astigmatism of the right observation optical system 13b which is computed in Step S94 using the apex angle of the contact prism 60 which is inputted in Step S91 and the fitting angle thereof which is inputted in Step S92 (Step S95). Here, the axial angle of the cylinder lenses 61A and 61B of the left observation optical system 13a is set to be equal to the axial angle of the cylinder lenses 61A and 61B of the right observation optical system 13b.

Next, the control unit 641 (adjusts the amount of correction for the astigmatism according to the observation magnification based on each of the variable lens systems 20 and 30 if necessary), generates control signals related to the amount of correction for the astigmatism, and transmits the control signals to the variable cross cylinder lens rotating drive units 65L and 65R, so that the cylinder lenses 61A and 61B of the left observation optical system 13a and the cylinder lenses 61A and 61B of the right observation optical system 13b are separately rotated to produce the computed amount of correction of the astigmatism in each of the right and the left (Steps S96 and S97).

In the observation apparatus that operates as described above according to this embodiment, even when the structure in which the TV image pickup system 50 is provided in only one of the right and the left is used, the astigmatism of the left observation optical system 13a and the astigmatism of the right observation optical system 13b can be separately corrected. Therefore, a structure of the apparatus can be simplified and a cost thereof can be reduced.

Figure 42:
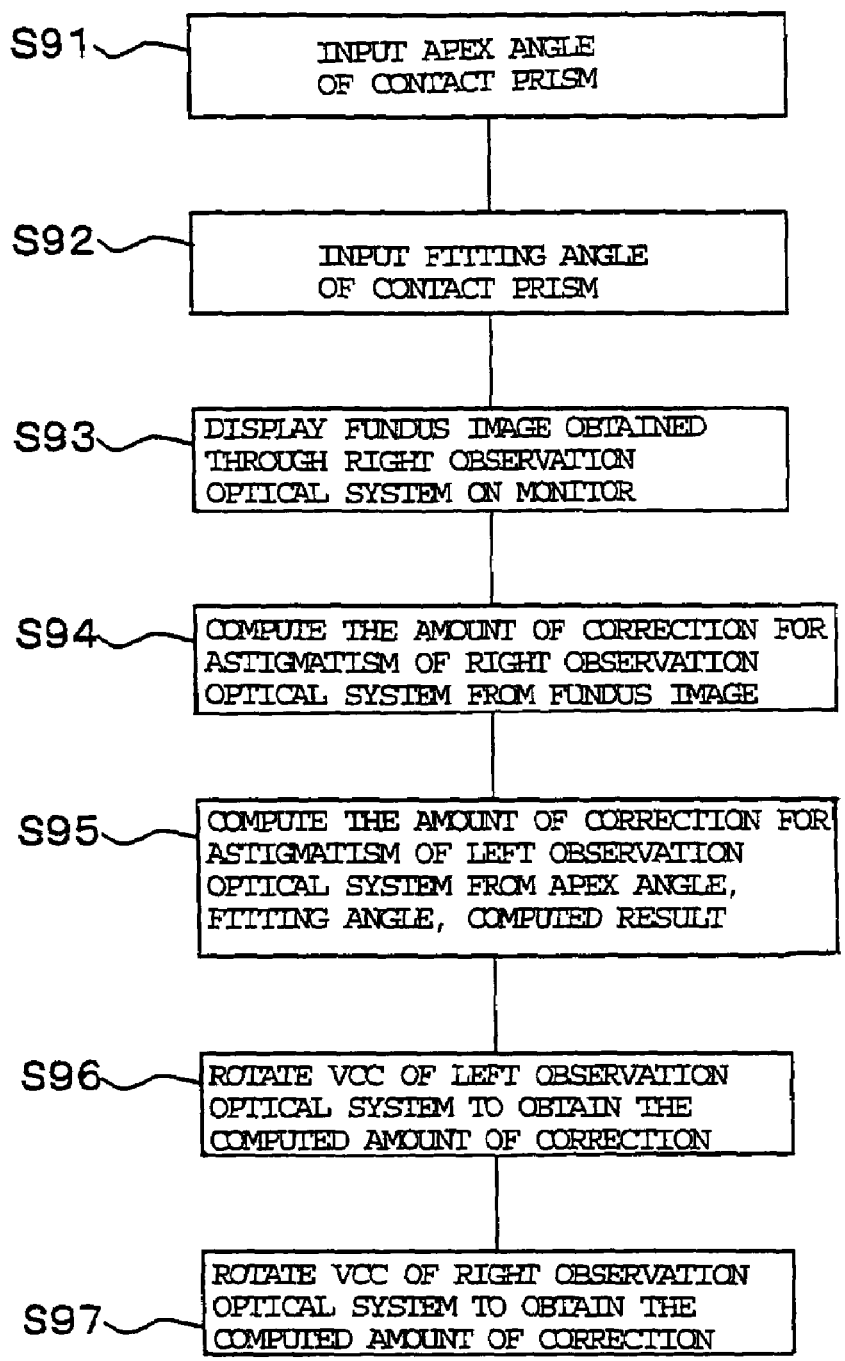
FIG. 42 is a flow chart showing an example of a use mode of the observation apparatus according to the fifth embodiment of the present invention.

Note that the chromatic aberration of the left observation optical system 13a and the chromatic aberration of the right observation optical system 13b can be separately corrected by the same process as the flow chart shown in FIG. 42.

MODIFIED EXAMPLE

In a modified example of the observation apparatus according to this embodiment, the amount of correction of each of the left and right observation optical systems 13a and 13b may be computed in advance based on the apex angle and the fitting angle of the contact prism 60 which are inputted and the analyzed result of the taken fundus image to store a computed result in the memory 644. When such a structure is used, the amount of correction for the astigmatism (chromatic aberration) of each of the left and right observation optical systems 13a and 13b is directly determined from the inputted apex angle, the inputted fitting angle, and the taken fundus image. Thus, it is unnecessary to perform computing processing during eye operation, so that speedy processing can be performed.

Sixth Embodiment

An observation apparatus according to a sixth embodiment of the present invention will be described with reference to the drawings. The observation apparatus according to this embodiment has a structure for focusing at an optimum position in the case where the astigmatism is corrected using the astigmatism canceling optical element (variable cross cylinder lens) 61.

The variable cross cylinder lens 61 acts to produce the same refracting power (spherical power) in directions in which axes are orthogonal to each other. Therefore, when the astigmatism is corrected with a state in which focusing is made at a position of the least circle of confusion, the front focal line and the rear focal line come close to the least circle of confusion, so that a preferable correction can be performed. In contrast to this, when the astigmatism is corrected with a state in which focusing is made at a position of the front focal line, a correction effect is caused but an observed fundus image blurs because of focusing on the front side (referred to as front side focusing in some cases). When the astigmatism is corrected with a state in which focusing is made at a position of the rear focal line, focusing is made on the rear side (referred to as rear side focusing in some cases). Thus, when the front side focusing or the rear side focusing is caused, it is necessary to perform focusing again, so that speedy correction cannot be performed.

In the observation apparatus according to this embodiment, the above-mentioned correction lens group (focal point correcting unit in the present invention) is used in order to prevent such situations. The correction lens group is composed of various lenses for correcting a positive or negative spherical power error caused by the cylinder lenses 61A and 61B. The various lenses of the correction lens group are selectively disposed on the observation optical paths by operating, for example, a foot switch which is not shown.

Assume that the amount of correction for the astigmatism which is produced by the cylinder lenses 61A and 61B is C diopters. In this time, the maximum amount of correction of necessary spherical power in each of states of the front side focusing and the rear side focusing becomes C/2 diopters. However, an initial focusing point before the correction performed by the correction lens group is not necessarily the position of the least circle of confusion, the front focal line, or the rear focal line. Therefore, the spherical power is changed within a range of C diopters as the amount of correction for the astigmatism. Correction lenses having respective diopters of +C, +C/2, 0, –C/2, and –C (referred to as focal correction lenses) are provided in advance in the correction lens group, corresponding to the amount of correction of C diopters.

An operator, while observing the eye to be operated E, operates the above-mentioned foot switch to exchange among the five correction lenses, and selects the one with an optimal focal state. Therefore, a displacement of the focusing position which is caused by the cylinder lenses 61A and 61B can be corrected. Alternately, the following may be performed. The five focal correction lenses are automatically exchanged for one another in succession. When a suitable focal correction lens is disposed, the operator operates the foot switch or the like to determine the focal correction lens.

The focal correction processing is manually performed by the operator. A focal displacement may be detected to perform automatic correction.

In order to correct a focal displacement, the operation microscope 10 itself may be moved forward and backward with respect to the eye to be operated E to correct the focusing position. Even in this case, with respect to a correction range, it is preferable that the amount of correction for the astigmatism which is produced by the cylinder lenses 61A and 61B is set to C diopters.

Seventh Embodiment

The operation microscope apparatus serving as the observation apparatus is described in each of the embodiments. However, the present invention is not limited to this and can be also applied to a slit lamp microscope and other observation apparatuses, in particular, ophthalmologic observation apparatuses.

Figure 43:
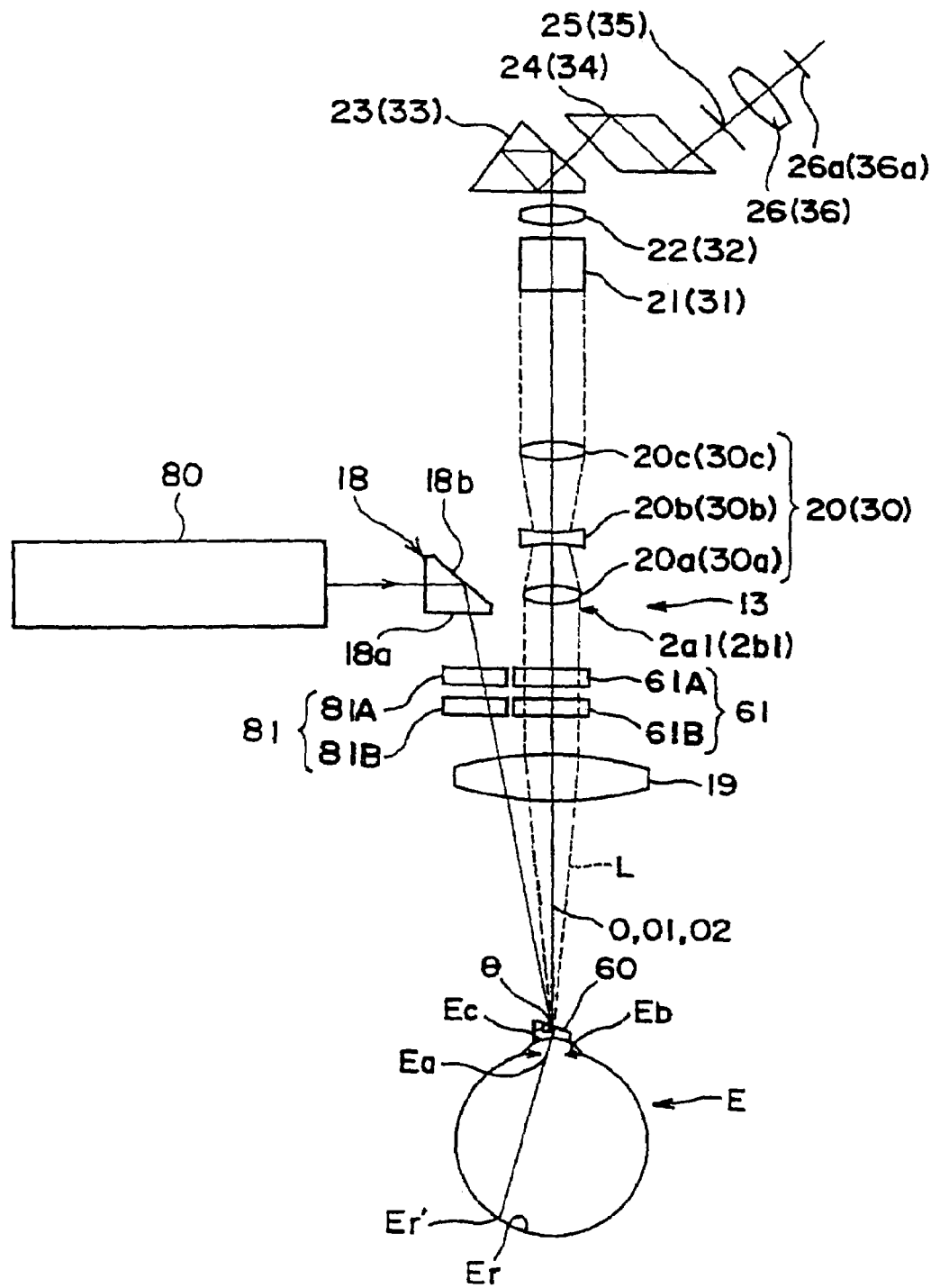
FIG. 43 is a side view showing a structure of an optical system of a laser therapy apparatus including an observation apparatus according to a seventh embodiment of the present invention.

FIG. 43 shows a structure of an optical system of an example of a laser therapy apparatus having the structure of the observation apparatus of the present invention. Note that the same references are provided to the same structural elements as described above and the description will be made. The laser therapy apparatus includes a known irradiation optical system 80 capable of irradiating the fundus Er of the eye to be operated E with therapy laser light. The therapy laser light from the irradiation optical system 80 is relayed as a parallel light flux by a collimating lens which is not shown and reflected on the prism 18 to be guided to the objective lens 19.

An astigmatism canceling optical element 81 for canceling the astigmatism caused when the contact prism 60 is put to the eye to be operated E and the fundus Er is irradiated with the therapy laser light through the contact prism 60 is provided between the prism 18 and the objective lens 19. The astigmatism canceling optical element 81 is composed of a set of cylinder lenses 81A and 81B as in the first embodiment. The amount of correction for the astigmatism which is produced by the cylinder lenses 81A and 81B can be automatically corrected by software processing with respect to the amount of correction for astigmatism caused in each of right and left observation images based on image data detected through each of the left and right observation optical systems 13a and 13b (collectively expressed by "13" in FIG. 43). A correction lens (group) capable of arbitrarily correcting a direction and a strength of power produced by the astigmatism canceling optical element 81, which is not shown, is provided.

According to the above-mentioned laser therapy apparatus, it is possible to remove the astigmatism caused when laser therapy is performed on the fundus Er with a state in which the contact prism 60 is put to the eye to be operated E. Even when the irradiation optical system 80 does not share the objective lens, it is possible to perform the irradiation in which the astigmatism is removed by suitably setting an irradiation angle of the therapy laser light.

OTHER APPLICATION EXAMPLE OF THE PRESENT INVENTION

The purpose of the observation apparatuses described above is to remove the astigmatism and the chromatic aberration which are caused when the contact prism is put to the eye to be observed (eye to be operated). According to the present invention, an astigmatism and a chromatic aberration which are caused when an optical member other than the contact prism is put to the eye can be removed in the same manner.

Figure 44:
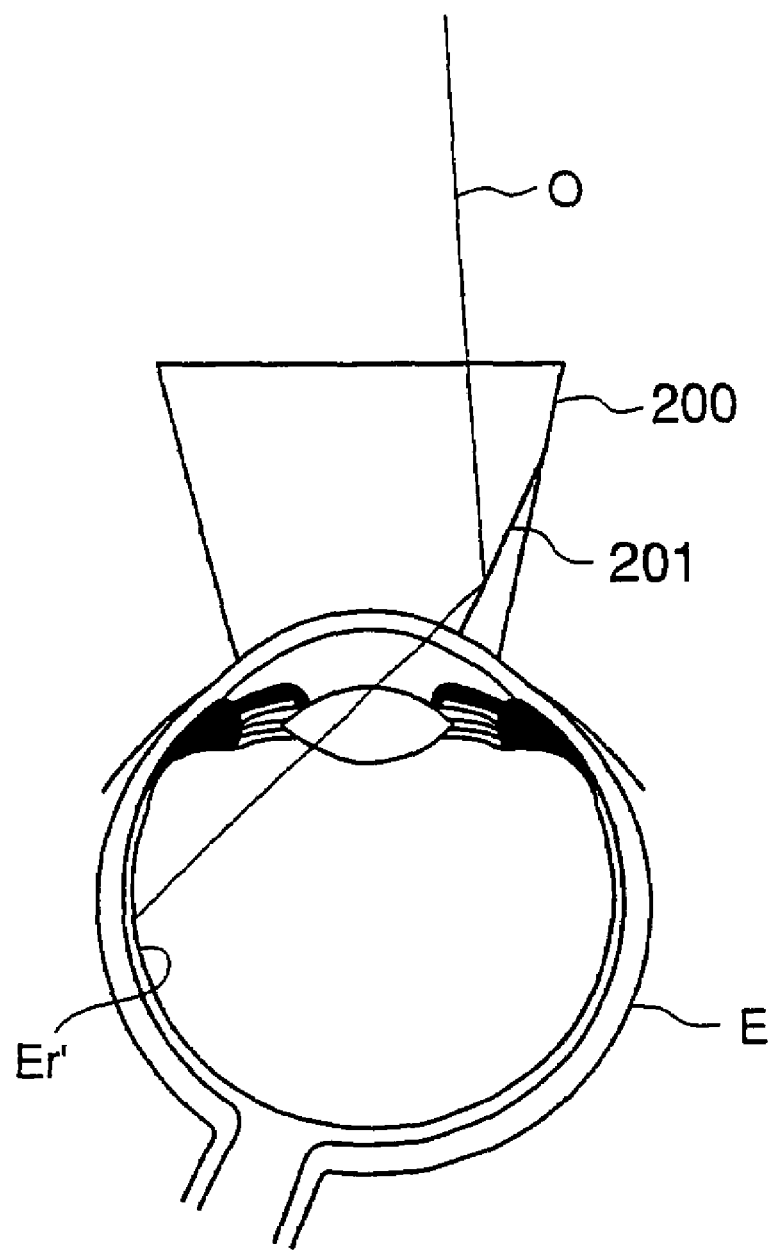
FIG. 44 is an explanatory view showing a state in which a contact lens is put to an eye to be observed.

As such an optical member, there is, for example, a contact lens (triple mirror) 200 as shown in FIG. 44. The contact lens 200 has a reflective surface 201 provided in an inner portion thereof. The fundus surroundings Er' of the eye to be observed E can be observed by deflecting light parallel to the observation optical axis O (at least one of the left and right observation optical axes O1 and O2) on the reflective surface 201. Even when the contact lens 200 is put to the eye to be observed E, the astigmatism and the chromatic aberration which are caused in the observation image. However, the astigmatism and the chromatic aberration can be cancelled by using the above-mentioned structure of the present invention.

Figure 45:
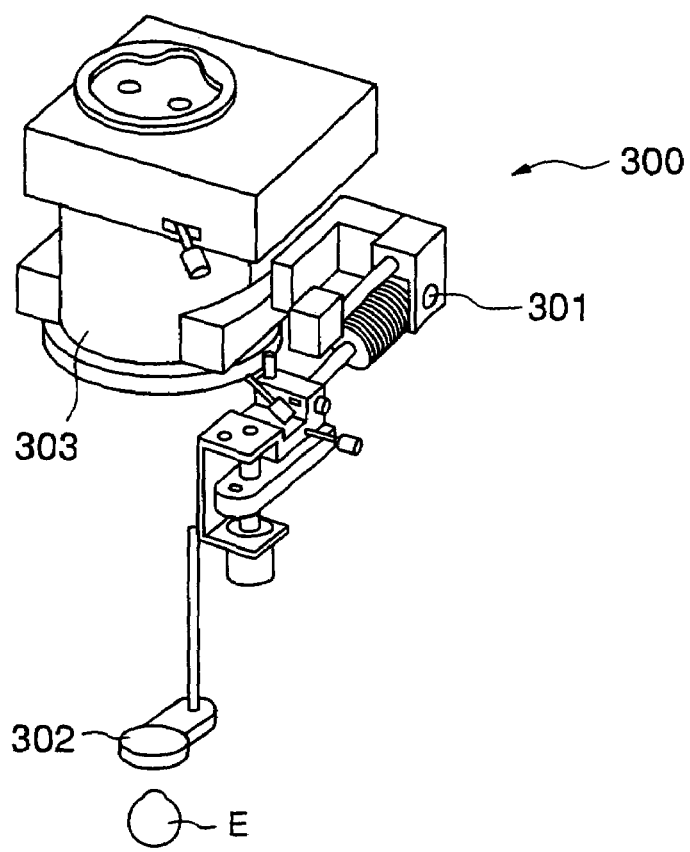
FIG. 45 is a perspective view showing an external structure of an example of an operation microscope apparatus including a front lens.

When the structure of the present invention is used for an operation microscope 300 as shown in FIG. 45, a preferable effect can be obtained. The operation microscope 300 includes a front lens 302 provided to be pivotable about a pivoting shaft 301. Therefore, the front lens 302 can be inserted between the eye to be operated E and a lens barrel 303 that stores an observation optical system including an objective lens. Even when the front lens 302 is placed between the objective lens and the eye to be operated E, the astigmatism and the chromatic aberration are caused in the observation image. However, when the structure of the present invention is applied to (right and left) observation optical systems in the lens barrel 303, the influences of the astigmatism and the chromatic aberration can be removed.

Figure 46:
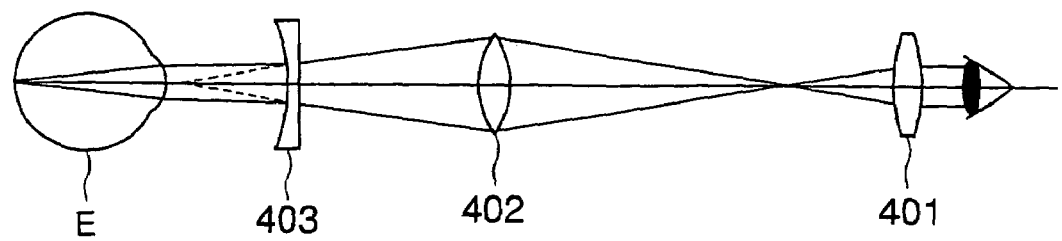
FIG. 46 shows an example of a structure of an optical system of a slip lamp microscope including a ruby lens.

The structure of the present invention can be also applied to a slit lamp microscope including a Hruby lens. FIG. 46 shows a schematic structure of an optical system of the slit lamp microscope. Reference numeral 401 denotes an eyepiece, 402 denotes an objective lens, and 403 denotes a Hruby lens. The Hruby lens 403 is a concave front lens for irradiating the eye to be observed E with narrow slit light as shown in FIG. 46, which is used to observe the posterior vitreous body of the eye to be observed E and the fundus thereof. Even when the Hruby lens 403 is placed between the eye to be observed E and the objective lens 402, the astigmatism and the chromatic aberration are caused in the observation image. However, when the structure of the present invention is used, the astigmatism and the chromatic aberration can be corrected.

Note that the structure of the present invention can be applied to aberration correction using various lenses placed between the objective lens and the eye to be observed with a non-contact state to the eye to be observed, other than the front lens described here. The structure of the present invention can be also applied to the correction of the aberration caused by various optical members placed in contact with the eye to be observed.

It is also possible to add a structure for correcting the astigmatism and the chromatic aberration (hereinafter collectively referred to as aberration) which are caused by the refracting power of each eyeball of an observer such as an operator. The refracting power of each eyeball of the observer is measured in advance and stored in, for example, the above-mentioned memory device of the image processing apparatus. A direction and the amount of aberration caused by the refracting power of each eyeball are calculated and the astigmatism canceling optical element and the chromatic aberration canceling optical element are operated according to a calculated result. In this time, when the aberration is caused by the contact prism or the like, the control for canceling both the aberration resulting from the contact prism and the aberration resulting from the eye balls is performed. A measurement optical system for measuring the refracting power of each eyeball of the observer may be provided in the observation apparatus and a measurement result obtained by the measurement optical system may be stored in the above-mentioned memory device or the like. When the observation apparatus includes such a structure for correcting the aberration caused by the refracting power of each eyeball of the observer, the adequate aberration correction can be performed for each observer.

The structure of the observation apparatus according to the present invention which is described above in detail is just an example as an embodiment. Therefore, various modifications, changes, additions, and the like can be made as appropriate without departing from the spirit of the present invention.

For example, the ring pattern is projected to the eye to be observed to take a ring pattern image. A distortion direction of the ring pattern image is detected to automatically detect the fitting angle of the contact prism which is put to the eye to be observed. The astigmatism canceling optical element and the chromatic aberration canceling optical element are operated according to the fitting angle. Therefore, a structure in which the fitting angle input unit in the present invention is not provided can be used.

It is possible to further provide a structure for removing the influence of the refracting power of each eye of the observer on the observation image. For example, spherical power, astigmatic power, and an astigmatism axis of each eye of the observer are stored in advance and the amount of correction for each of the astigmatism and the chromatic aberration and a direction of each correction are determined in view of the influence. A structure capable of setting the eye refracting power of the observer by the control panel or the like may be used.

According to the observation apparatus in first to fourteenth aspects of the present invention, the astigmatisms caused in right and left observation images at the time of observing fundus surroundings can be separately corrected, so that preferable aberration correction can be performed.

According to the observation apparatus in the second aspect of the present invention, effective aberration correction can be performed by the variable cross cylinder lens.

According to the observation apparatus in the third aspect of the present invention, a direction of correction and the amount of correction for each of the astigmatisms caused in right and left observation images can be set for each of right and left and the correction can be performed corresponding to a set content, so that operability can be improved.

According to the observation apparatus in the fourth aspect of the present invention, the astigmatisms caused in right and left observation images can be separately corrected by only inputting the apex angle and the fitting angle of the contact prism, so that it is convenient for the operation.

According to the observation apparatus in the fifth aspect of the present invention, the astigmatisms caused in right and left observation images can be automatically corrected separately based on the observation magnification, so that adequate correction is possible and operability can be improved.

According to the observation apparatus in the sixth aspect of the present invention, the astigmatisms caused in right and left observation images can be automatically corrected separately based on the received fundus image, so that operability can be improved.

According to the observation apparatus in the seventh aspect of the present invention, the astigmatisms caused in right and left observation images can be automatically corrected separately based on the received pattern image of a pattern projected to a fundus, so that operability can be improved. The pattern having a known shape is used, so that correction can be accurately performed.

According to the observation apparatus in the eighth and ninth aspects of the present invention, the astigmatisms caused in both right and left observation images can be corrected based on the observation image obtained through only one of the right and left observation optical systems. Therefore, a structure of the observation apparatus can be simplified and a cost of the observation apparatus can be reduced.

In particular, according to the observation apparatus in the ninth aspect of the present invention, a processing time for correcting the astigmatism is shortened, so that it is conveniently used.

According to the observation apparatus in the tenth aspect of the present invention, even when a contact prism having an apex angle different from a reference apex angle is put to the eye to be observed, the astigmatisms caused in right and left observation images can be automatically and speedily corrected separately.

According to the observation apparatus in the eleventh aspect of the present invention, more adequate aberration correction can be performed by operating the correction lens.

According to the observation apparatus in the twelfth and thirteenth aspects of the present invention, the displacement of the focusing position caused by the variable cross cylinder lens can be corrected, so that the convenience in use can be improved.

In particular, according to the observation apparatus in the thirteenth aspect of the present invention, the displacement of the focusing position can be easily corrected using the plurality of correction lenses having different spherical powers.

According to the observation apparatus in the fourteenth aspect of the present invention, the astigmatism and the chromatic aberration can be separately corrected for each of right and left.

According to the observation apparatus in fifteenth to twenty-first aspects of the present invention, the chromatic aberrations caused in right and left images at the time of observing fundus surroundings can be separately corrected, so that preferable aberration correction can be performed.

According to the observation apparatus in the sixteenth aspect of the present invention, a direction of correction and the amount of correction for each of the chromatic aberrations caused in right and left observation images can be set for each of right and left and the correction can be performed corresponding to a set content, so that operability can be improved.

According to the observation apparatus in the seventeenth aspect of the present invention, the chromatic aberrations caused in right and left observation images can be separately corrected by only inputting the apex angle and the fitting angle of the contact prism, so that it is convenient for the operation.

According to the observation apparatus in the eighteenth aspect of the present invention, the chromatic aberrations caused in right and left observation images can be automatically corrected separately based on the observation magnification, so that adequate correction is possible and operability can be improved.

According to the observation apparatus in the nineteenth and twentieth aspects of the present invention, the chromatic aberrations caused in both right and left observation images can be corrected based on the observation image obtained through only one of the right and left observation optical systems. Therefore, a structure of the observation apparatus can be simplified and a cost of the observation apparatus can be reduced.

In particular, according to the observation apparatus in the twentieth aspect of the present invention, a processing time for correcting the chromatic aberrations is shortened, so that it is conveniently used.

According to the observation apparatus in the twenty-first aspect of the present invention, the chromatic aberration can be automatically corrected for each of right and left by performing digital processing on the received fundus image. Therefore, it is unnecessary to provide a chromatic aberration canceling optical element on each observation optical path. Such a structure is convenient because it can be applied without changing, for example, a structure of a known optical path.

What is claimed is:

1. An observation apparatus, comprising: a variable lens system for changing an observation magnification for observing an eye to be observed, which is an observation object; and an imaging lens for imaging a light flux passing through the variable lens system, the variable lens system and the imaging lens being disposed on one or more observation optical paths between an objective lens opposed to the eye to be observed and eyepieces, an observation optical path which is for relaying a reflection light flux on the eye to be observed as a parallel light flux to the variable lens system, being formed between the objective lens and the variable lens system in the observation optical paths, an observation optical path, which is for relaying the reflection light flux obtained through the variable lens system as a parallel light flux to the imaging lens, being formed between the variable lens system and the imaging lens in the observation optical paths, wherein an astigmatism canceling optical element for canceling power of astigmatism that occurs when a predetermined optical member is placed between the eye to be observed and the objective lens, is provided on the observation optical paths, wherein the astigmatism canceling optical element comprises a variable cross cylinder lens composed of a pair of concave cylinder lens and a convex cylinder lens, which are provided to be relatively rotatable about an observation optical axis of the observation optical path, wherein the predetermined optical member placed between the eye to be observed and the objective lens includes a prism fit in contact with a cornea of the eye to be observed, wherein the observation apparatus further comprises:

apex angle input means for inputting an apex angle of the prism;

fitting angle input means for inputting a fitting angle of the prism to the cornea;

drive means for independently rotating right and left respectively the variable cross cylinder lenses; and control means for independently controlling rotation of the right and left variable cross cylinder lenses by the drive means based on the apex angle inputted by the apex angle input means and the fitting angle inputted by the fitting angle input means.

2. An observation apparatus according to claim 1, wherein the variable cross cylinder lens comprises:

aberration direction setting means for setting a direction of the power of the astigmatism; and correction amount setting means for setting an amount of correction for canceling the power of the astigmatism.

3. An observation apparatus according to claim 1, wherein the control means controls rotation of the variable cross cylinder lenses by the drive means based on the observation magnification changed by the variable lens system.

4. An observation apparatus according to claim 1, further comprising:

image receiving means for receiving observation images of the eye to be observed from the reflection light fluxes on the eye to be observed, which are guided through the observation optical paths; and correction amount computing means for computing an amount of correction for canceling the power of the astigmatism by performing predetermined analyzing processing on the observation images received by the image receiving means, wherein the control means controls rotation of the variable cross cylinder lenses respectively by the drive means based on the correction amount computed by the correction amount computing means.

5. An observation apparatus according to claim 1, further comprising:

a projection optical system for projecting a pattern image to the eye to be observed;

image receiving means for receiving reflection images of the pattern image projected to the eye to be observed by the projection optical system, which are guided through the observation optical paths; and correction amount computing means for computing the amount of correction for canceling the power of the astigmatism by performing predetermined analyzing processing on the reflection images of the pattern image which are received by the image receiving means, wherein the control means controls rotation of the variable cross cylinder lenses respectively by the drive means based on the amount of correction computed by the correction amount computing means.

6. An observation apparatus according to claim 1, wherein right and left observation optical paths are disposed between an objective lens opposed to the eye to be observed and eyepieces for right and left eyes, wherein the astigmatism canceling optical element which is right and left independently operable, is provided on each of the right and left observation optical paths, the observation apparatus further comprising:

image receiving means for receiving an observation image of the eye to be observed from the reflection light flux on the eye to be observed, which is guided through one of the right and left observation optical paths; and correction amount computing means for computing an amount of correction for canceling the power of the astigmatism that occurs in the one of the right and left observation optical paths by performing predetermined analyzing processing on the observation image received by the image receiving means and then computing an amount of correction for canceling the power of the astigmatism that occurs in the other of the right and left observation optical paths based on the computed correction amount, wherein the astigmatism canceling optical elements are independently operated right and left respectively based on the amount of correction for the astigmatism in each of the right and left observation optical paths, which is computed by the third correction amount computing means.

7. An observation apparatus according to claim 1, wherein right and left observation optical paths are disposed between an objective lens opposed to the eye to be observed and eyepieces for right and left eyes, wherein the astigmatism canceling optical element which is right and left independently operable, is provided on each of the right and left observation optical paths, the observation apparatus further comprising:

memory means for storing an amount of correction for canceling the power of the astigmatism, corresponding to the apex angle of the prism and the fitting angle of the prism;

image receiving means for receiving an observation image of the eye to be observed from the reflection light flux on the eye to be observed, which is guided through one of the right and left observation optical paths; and correction amount computing means for computing an amount of correction for canceling the power of the astigmatism that occurs in the one of the right and left observation optical paths by performing predetermined analyzing processing on the observation image received by the image receiving means and then computing an amount of correction for canceling the power of the astigmatism that occurs in the other of the right and left observation optical paths based on the computed correction amount and the amount of correction for canceling the power of the astigmatism, corresponding to the apex angle and the fitting angle, which is stored in the memory means, wherein the control means independently controls rotation of the right and left variable cross cylinder lenses respectively by the drive means based on the amount of correction for the astigmatism in each of the right and left observation optical paths, which is computed by the correction amount computing means.

8. An observation apparatus according to claim 1, further comprising:

memory means for storing an amount of correction for canceling power of an astigmatism caused by a prism having a predetermined apex angle in association with an observation magnification changed by the variable lens system; and correction amount calculating means for calculating an amount of correction for a prism having an apex angle different from the predetermined apex angle at an observation magnification different from a specific observation magnification based on the amount of correction which is stored in the memory means in association with the observation magnification and the amount of correction for the prism having the apex angle different from the predetermined apex angle at the specific observation magnification, which is obtained in advance, wherein the control means controls rotation of the variable cross cylinder lenses respectively by the drive means based on the amount of correction for the astigmatism in the observation optical paths, which is calculated by the correction amount calculating means.

9. An observation apparatus according to claim 1, further comprising a correction lens for changing a direction of positive or negative power produced by the variable cross cylinder lens to a direction of positive or negative power of the astigmatism.

10. An observation apparatus according to claim 1, further comprising focusing position correction means for correcting displacement of a focusing position which occurs when the astigmatism is canceled by the variable cross cylinder lens.

11. An observation apparatus according to claim 10, wherein the focusing position correction means comprises a correction lens group for changing a direction of positive or negative power produced by the variable cross cylinder lens to a direction of positive or negative power of the astigmatism, the group being composed of a plurality of correction lenses different from each other in spherical power.

12. An observation apparatus according to claim 1, further comprising a chromatic aberration canceling optical element for canceling chromatic aberration that occurs when the predetermined optical member is placed between the eye to be observed and the objective lens, the chromatic aberration canceling optical element being respectively operable and provided between the variable lens system and the imaging lens on the observation optical paths.

13. An observation apparatus, comprising: a variable lens system for changing an observation magnification for observing an eye to be observed, which is an observation object; and an imaging lens for imaging a light flux passing through the variable lens system, the variable lens system and the imaging lens being disposed on each of right and left observation optical paths between an objective lens opposed to the eye to be observed and eyepieces for right and left eyes, an observation optical path, which is for relaying a reflection light flux on the eye to be observed as a parallel light flux to the variable lens system, being formed between the objective lens and the variable lens system in each of the right and left observation optical paths, an observation optical path, which is for relaying the reflection light flux obtained through the variable lens system as a parallel light flux to the imaging lens, being formed between the variable lens system and the imaging lens in each of the right and left observation optical paths, wherein a chromatic aberration canceling optical element for canceling chromatic aberration that occurs when a predetermined optical member is placed between the eye to be observed and the objective lens, which is right and left independently operable, is provided on each of the right and left observation optical paths.

14. An observation apparatus according to claim 13, wherein the chromatic aberration canceling optical element comprises:

aberration direction setting means for setting a direction of the power of the chromatic aberration; and correction amount setting means for setting an amount of correction for canceling the power of the chromatic aberration.

15. An observation apparatus according to claim 13, wherein the predetermined optical member placed between the eye to be observed and the objective lens includes a prism fit in contact with a cornea of the eye to be observed, wherein the observation apparatus further comprises:

apex angle input means for inputting an apex angle of the prism;

fitting angle input means for inputting a fitting angle of the prism to the cornea; and control means for controlling operation of the chromatic aberration canceling optical element based on the apex angle inputted by the apex angle input means and the fitting angle inputted by the fitting angle input means.

16. An observation apparatus according to claim 15, wherein the control means controls operation of the chromatic aberration canceling optical element based on the observation magnification changed by the variable lens system.

17. An observation apparatus according to claim 15, further comprising:

memory means for storing an amount of correction for canceling the chromatic aberration, corresponding to the apex angle of the prism and the fitting angle of the prism;

image receiving means for receiving an observation image of the eye to be observed from the reflection light flux on the eye to be observed, which is guided through one of the right and left observation optical paths; and fourth correction amount computing means for computing an amount of correction for canceling the chromatic aberration that occurs in the one of the right and left observation optical paths by performing predetermined analyzing processing on the observation image received by the image receiving means and then computing an amount of correction for canceling the chromatic aberration that occurs in the other of the right and left observation optical paths based on the computed correction amount and the amount of correction for canceling the chromatic aberration, corresponding to the apex angle and the fitting angle, which is stored in the memory means, wherein the control means right and left independently controls the chromatic aberration canceling optical elements based on the amount of correction for the chromatic aberration in each of the right and left observation optical paths, which is computed by the fourth correction amount computing means.

18. An observation apparatus according to claim 13, further comprising:
image receiving means for receiving an observation image of the eye to be observed from the reflection light flux on the eye to be observed, which is guided through one of the right and left observation optical paths; and
correction amount computing means for computing an amount of correction for canceling the chromatic aberration that occurs in the one of the right and left observation optical paths by performing predetermined analyzing processing on the observation image received by the image receiving means and then computing an amount of correction for canceling the chromatic aberration that occurs in the other of the right and left observation optical paths based on the computed correction amount,
wherein the chromatic aberration canceling optical elements are right and left independently operated based on the amount of correction for the chromatic aberration in each of the right and left observation optical paths, which is computed by the correction amount computing means.

19. An observation apparatus, comprising:
a variable lens system for changing an observation magnification for observing an eye to be observed, which is an observation object;
an imaging lens for imaging a light flux passing through the variable lens system, the variable lens system and the imaging lens being disposed on one or more observation optical paths between an objective lens opposed to the eye to be observed and eyepieces;
an observation optical path, which is for relaying a reflection light flux on the eye to be observed as a parallel light flux to the variable lens system, being formed between the objective lens and the variable lens system in the observation optical paths, an observation optical path, which is for relaying the reflection light flux obtained through the variable lens system as a parallel light flux to the imaging lens, being formed between the variable lens system and the imaging lens in the observation optical paths;
image receiving means for receiving observation images of the eye to be observed from the reflection light fluxes on the eye to be observed, which are guided through the observation optical paths;
display means for displaying the observation images received by the image receiving means; and
chromatic aberration correcting means for correcting chromatic aberration in the observation images by performing digital processing in which positions of point images of R, G, and B of the observation images received by the image receiving means are aligned with one another on the display means, the point images being separated by the chromatic aberration that occurs when a predetermined optical member is placed between the eye to be observed and the objective lens,
wherein the predetermined optical member placed between the eye to be observed and the objective lens includes a prism fit in contact with a cornea of the eye to be observed,
wherein the observation apparatus further comprises:
apex angle input means for inputting an apex angle of the prism;
fitting angle input means for inputting a fitting angle of the prism to the cornea; and
a control means for controlling operation of the chromatic aberration canceling optical element based on the apex angle inputted by the apex angle input means and the fitting angle inputted by the fitting angle input means.

20. The observation apparatus according to claim 1, wherein the variable lens system and the imaging lens are disposed on each of right and left observation optical paths between an objective lens opposed to the eye to be observed and eyepieces for right and left eyes,
wherein an astigmatism canceling optical element which is right and left independently operable, is provided on each of the right and left observation optical paths.

* * * * *